US008143287B2

(12) United States Patent
Spencer et al.

(10) Patent No.: US 8,143,287 B2
(45) Date of Patent: *Mar. 27, 2012

(54) THROMBOPOIETIN MIMETICS

(75) Inventors: Jeffrey R. Spencer, South San Francisco, CA (US); Juha Punnonen, Belmont, CA (US)

(73) Assignee: Stategics, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/853,800

(22) Filed: Aug. 10, 2010

(65) Prior Publication Data

US 2010/0323965 A1 Dec. 23, 2010

Related U.S. Application Data

(63) Continuation of application No. 11/948,955, filed on Nov. 30, 2007, now Pat. No. 7,786,159.

(60) Provisional application No. 60/861,963, filed on Dec. 1, 2006.

(51) Int. Cl.
*A61K 31/454* (2006.01)
*A61K 31/4152* (2006.01)
*C07D 401/02* (2006.01)
*C07D 231/46* (2006.01)
(52) U.S. Cl. ...... 514/326; 514/404; 546/211; 548/367.4
(58) Field of Classification Search .................. 514/326, 514/404; 546/211; 548/367.7
See application file for complete search history.

(56) References Cited

U.S. PATENT DOCUMENTS

| 3,141,772 | A | 7/1964 | Green |
| 3,666,746 | A | 5/1972 | Stanley et al. |
| 7,160,870 | B2 | 1/2007 | Duffy |
| 7,414,040 | B2 | 8/2008 | Heerding |
| 7,786,159 | B2 | 8/2010 | Spencer et al. |
| 2004/0019190 | A1 | 1/2004 | Erickson-Miller et al. |
| 2006/0116417 | A1 | 6/2006 | Chen et al. |

FOREIGN PATENT DOCUMENTS

| BE | 621 310 A | 2/1963 |
| DE | 11 82 432 B | 11/1964 |
| DE | 20 30 783 A1 | 1/1971 |
| DE | 40 28 184 A1 | 3/1991 |
| EP | 1 125 990 A1 | 8/2001 |
| JP | 4-128767 A | 4/1992 |
| WO | WO 01/17349 A1 | 3/2001 |
| WO | WO 01/89457 A2 | 11/2001 |
| WO | WO 03/103686 A1 | 12/2003 |
| WO | WO 2005/118551 A2 | 12/2005 |
| WO | WO 2007/062078 A2 | 5/2007 |
| WO | WO 2007/087068 A2 | 8/2007 |
| WO | WO 2008/070583 A2 | 6/2008 |

OTHER PUBLICATIONS

Abdou, Ibrahim M. et al., "Synthesis and Antitumor Activity of 5-Trifluoromethyl-2, 4-dihydropyrazol-3-one Nicleosides," *Molecules*, vol. 9, No. 3, 109-116 (2004).

Ashry, El Sayed H. et al., "Assignment of the location of the isopropylidene ring in 1-C-substituted-threo-glycerols by 13C-n.m.r. spectroscopy," *Carbohydrate Research*, vol. 163, 262-264 (1987).

Badham, N. F., et al., "Rearrangement of Epoxynitriles: A Convenient Homologation of Acyclic and Cyclic Ketones to Carboxylic Acids," *J. Org. Chem.*, 67:5440-5443 (2002).

Detsi, A., et al., "Synthesis of N-alkoxycarbonyl-3-substitute tetramic acids and functionalized enols via C-acylaton reactions of active methylene compounds with N-hydroxysuccinimide esters of N-alkoxycarbonyl-α-amino acids," *J. Chem. Soc., Perkin Trans*, pp. 2443-2449 (1998).

Etman H. A. et al., "Behaviour of 4-Arylhydrazono-3-methyl-2-pyrazolin-5-one s towards Acetylation, Hdroxymethylation, Mannich Reaciton and Chlorosulphonation," *Journal of the Indian Chemical Society*, vol. 67, 213-15 (1990).

Feese, et al., "Structure of the receptor-binding domain of human thrombopoietin determined by complexation with a neutralizing antibody fragment," *Proceedings in the National Academy of Science*, 101:1816-1821; pp. 1817-1818 (2004).

Gonzalez-Bobes, et al., "Amino Alcohols as Ligands for Nickel-Catalyzed Suzuki Reactions of Unactivated Alkyl Halides, Including Secondary Alkyl Chlorides, with Arylboronic Acids," *J. Am. Chem. Soc.*, 128:5360-5361 (2006).

Gordon, et al., "A Phase I Trial of Recombinant Human Interleukin-11 (Neumega rhIL-11 Growth Factor) in Women with Breast Cancer Receiving Chemotherapy," *Blood*, 87(9):3615-3623 (1996).

Hayashi, et al., "(R)-3-Phenylcyclohexanone," *Organic Syntheses*, Coll. 10:609 (2004); 79:84 (2002).

Itooka, R., et al., "Rhodium-Catalyzed 1,4-Addition of Arylboronic Acids to α,β-Unsaturated Carbonyl Compounds: Large Accelerating Effects of Bases and Ligands," *J. Org. Chem.*, 68:6000-6004 (2003).

Jenkins, J .M., et al., "Phase 1 clinical study of eltrombopag, an oral, nonpeptide thrombopoietin receptor agonist." *Blood*, 109(11):4739-4741 (2007).

(Continued)

*Primary Examiner* — Kamal Saeed
*Assistant Examiner* — Kristin Bianchi
(74) *Attorney, Agent, or Firm* — Morgan, Lewis & Bockius LLP; Jeffry S. Mann; Todd W. Esker

(57) ABSTRACT

The invention relates to compounds and their use in the treatment of thrombocytopenia resulting from diseases or conditions such as immune thrombocytopenic purpura, cancer chemotherapy, surgery, bone marrow or stem cell transplantation, radiation injury or treatment, chronic viral infection, and pancytopenia. The invention further relates to pharmaceutical compositions containing the compounds and compositions of the invention as well as methods for treating such diseases or conditions in a mammal, including a human, by administering to such mammal an effective amount of a selected thrombopoietin receptor agonist.

46 Claims, No Drawings

OTHER PUBLICATIONS

Kuter, D. J., Begley, C. G., "Recombinant human thrombopoietin: basic biology and evaluation of clinical studies," *Blood*, 100(10):3457-3469 (2002).

Oldenziel, O. H., et al., "A General One-Step Synthesis of Nitriles from Ketones Using Tosylmethyl Isocyanide, Introduction of a One-Carbon Unit," *J. Org. Chem.*, 42(19):3114-3118 (1977).

Poschenrieder, H., et al., "5-Arylidene-3-aryl-pyrrolidine-2,4-diones with Affinity to the N-Methyl-D-aspartate (Glycine Site)Receptor, Part I," *Arch. Pharm. Med. Chem.*, 331:389-394 (1998).

Sakai, M., et al., "Rhodium-Catalyzed Conjugate Addition of Aryl- or 1-Alkenylboronic Acids to Enones," *Organometallics*, 16(20):4229-4231 (2007).

Sekhon, S. S., Roy, V., "Thrombocytopenia in Adults: A Practical Approach to Evaluation and Management," *South. Med. J.*, 99(5):491-498 (2006).

Shukula, P.R. et al., "Some Transition Metal Complexes Derived from the Heterocyclic Ligands 3-Methyl-4-Arylazopyrazole-5-Ones," *Journal of the Indian Chemical Society*, vol. 58, 937-939 (1981).

Vippagunta et al., "Crystalline solids," *Advanced Drug Delivery Reviews*, 48, pp. 3 and 18 (2001).

THROMBOPOIETIN MIMETICS

This application is a continuation of U.S. patent application No. 11/948,955; filed on Nov. 30, 2007 now U.S. Pat. No. 7,786,159, which claims priority to U.S. Provisional Patent Application Ser. No. 60/861,963 filed on Dec. 1, 2006, which are herein incorporated by reference in their entirety for all purposes.

FIELD OF THE INVENTION

The present invention is directed to novel thrombopoietin mimetics that are useful as promoters of stem cell growth, thrombopoiesis and megakaryopoiesis.

BACKGROUND OF THE INVENTION

Thrombopoietin (TPO) is the primary physiological regulator of thrombopoiesis, which is the formation of blood platelets. The first evidence for a humoral substance responsible for stimulating the production of platelets in thrombocytopenic rats was provided in 1958 (Keleman, E., et al., Acta Haematol. (1958) 20: 350-355). Since then, the purification and characterization of TPO, also referred to as megakaryocyte growth and development factor (MGDF) and c-Mpl ligand, have been achieved (de Sauvage, F. J., et al., Nature, (1994) 369: 533; Kuter, D., et al., Proc. Natl. Acad. Sci. USA (1994) 91: 11104; Sohma, Y., et al., FEBS Lett. (1994) 353: 57-61). The cloning and expression of TPO by standard techniques was also accomplished at approximately the same time (Bartley, T. D., et al., Cell (1994) 77: 1117; Lok, S., et al., Nature (1994) 369: 565), which later enabled the production of recombinant protein preparations for human clinical trials.

TPO is also one of the key cytokines driving the growth of stem cells and early hematopoietic progenitor cells. TPO alone stimulates clonal growth from single primitive CD34+ CD38− human bone marrow cells, and it strongly synergizes with c-kit ligand (KL), flt3 ligand (FL) and IL-3 to enhance clonogenic growth (Borge, O. J., et al., Blood (1997) 90: 2282; Muench, M. O. and Barcena, A., Pediatr. Res. (2004) 55: 1050. TPO also enhanced clonogenic growth in response to KL+FL+IL-3+IL-6+EPO by as much as 80% and resulted in 40-fold expansion of multipotent progenitors following a 14-day incubation, further implicating a key role for this cytokine in stem cell growth and early hemopoiesis (Borge, O. J., et al., Blood (1997) 90: 2282). TPO enhances the growth and differentiation of human embryonic stem cells (Srivastava, A. S. et al. Stem Cells (2007) 25:1456). Stem cell-based approaches have demonstrated promising results in the treatment of several diseases, such as myocardial infarction, soft-tissue injury, heart failure, repair of atherosclerotic vessels and diseases of the central nervous system (Urbich, C., and S. Dimmeler (2004). Circ. Res. 95:343; Sylvester, K. G., and M. T. Longaker (2004) Arch. Surg. 139:93; Yoon, Y. S. et al. (2005) Biol Cell. 97:253; Martino, G., and S. Pluchino. (2006) Nat. Rev. Neurosci. 7:395).

Platelets are essential to the blood clotting process. If platelet production is inhibited or platelet levels become lower than levels that are considered to be normal, then the patient can develop thrombocytopenia, a potentially serious condition for which a TPO mimetic could provide significant relief. Serious consequences of thrombocytopenia include fatigue, bleeding, bruising, hemorrhage, and increased mortality as a result of related conditions. Thrombocytopenia can result from reduced production of platelets or increased breakdown of platelets via multiple different mechanisms. The leading causes of thrombocytopenia are cancer chemotherapy, surgery, bone marrow or stem cell transplantation, radiation injury or treatment, severe bacterial infections, chronic viral infection, systemic lupus erythematosus, rheumatoid arthritis, treatment with other drugs causing thrombocytopenia and a disorder known as immune thrombocytopenic purpura (also known as idiopathic thrombocytopenic purpura) (ITP) where the body's ability to produce and maintain an adequate supply of platelets is reduced for various reasons. Common drugs causing thrombocytopenia include heparin, quinidine, quinine, sulfa-containing antibiotics, some oral diabetes drugs, gold salts, rifampin and interferon-alpha.

The preferred acute treatment for severe thrombocytopenia, for example due to liver transplantation, is platelet transfusion, which can be costly, difficult, and associated with risks (Kuter, D. J., et al., Blood (2002) 100: 3457). Various therapeutics for thrombocytopenia that have either direct or indirect effects on platelet production are also known. For example, the first line of treatment for patients with ITP generally is the corticosteroid prednisone (Louwes, H. et al., Ann. Hematol. (2001) 80: 728). Prednisone is effective in approximately one-third of patients and is thought to reduce the amount of platelet-associated autoantibodies, which can participate in the clearing of platelets (Fujisama, et al., Blood (1993), 81: 2872), although this mechanism is not completely understood. Another therapeutic for ITP is intravenous immunoglobulin (IVIg), which is thought to modulate the production of antibodies and the activity of macrophages in removing platelets (Siragam, V. et al., Nat. Med. (2006) 12: 688-692), although the pharmacological mechanism of action of IVIg is also poorly understood. Patients who are refractory to the above treatments, such as prednisone and IVIg, may be considered for surgical removal of the spleen, which is a primary site of platelet sequestration. However, this procedure may have serious associated adverse events and is not considered as a cure for ITP. The cytokine growth factor, interleukin-11 (IL-11), is also approved for treating thrombocytopenia and has been shown to significantly increase platelet levels in adults following myelosuppressive chemotherapy. However, unlike TPO, IL-11 has pleiotropic effects and may be associated with serious adverse events such as peripheral edema and atrial arrhythmia (Gordon, M. S., et al., Blood (1996) 87: 3615).

Recombinant TPO preparations were available recently for clinical evaluation in certain indications, such as cancer chemotherapy. Two such products, PEG-rHu-MGDF (Basser, R. L. et al., Lancet (1996) 348: 1279) and rhTPO (Vadhan-Raj, S. et al., Ann. Intern. Med. (1997) 126: 673), act to promote platelet production directly by binding to the cell-surface TPO receptor. Certain cancer therapeutic regimens, including agents such as platinum drugs, paclitaxel, cyclophosphamide, doxorubicin, and ifosfamide, are associated with thrombocytopenia and frequently require dose modification and/or platelet transfusions to manage complications such as bleeding. The TPO products, PEG-rHu-MGDF and rh-TPO, both showed positive results in clinical trials by reducing chemotherapy-induced thrombocytopenia and in some cases reduced the need for platelet transfusions. However, PEG-rHu-MGDF was associated with production of neutralizing antibodies, which resulted in serious, treatment-resistant thrombocytopenia, thus raising concerns over safety in long-term administration. Both of the recombinant TPO products have been discontinued.

Recombinant TPO was also shown to be useful in the treatment of thrombocytopenia associated with human immunodeficiency virus (HIV) infection (Sundell, I. B., and Koka, P. S., Curr. HIV Res. (2006) 4: 107). During HIV infection, megakaryopoiesis, which is the process by which hematopoietic stem cells in the bone marrow differentiate into mature megakaryocytes, may become inhibited and the megakaryocytes may become infected with the virus, thus lowering the production of platelets. It is in this lowered state of platelet production that a TPO mimetic may be of therapeutic utility.

It is also known that healthy apheresis donors may require supportive treatment to increase platelet levels either prior to or after such procedures (Kuter, D. J. et al., Blood (2001) 96: 1339). A single injection of PEG-rHu-MGDF to healthy volunteers resulted in a dose-dependent increase in platelet counts and a correspondingly higher platelet yield from apheresis. This also suggests a potential use of a TPO mimetic compound.

It is known that thrombocytopenia can result from a disease or condition that results in reduced numbers of CD34+ human primary cells and further that such cells are responsive to recombinant TPO and TPO mimetics in animals, including humans, and in culture. This responsiveness results from the expression of TPO receptor on the surface of the cells and the intracellular signaling, including activation of STATS, that is caused by binding of TPO or a mimetic to the receptor. Therefore, assays using these human primary cells in culture are particularly useful in evaluating the utility of novel TPO mimetics in animals, including human (Erickson-Miller, C. L., et al., Exp. Hematology (2005) 33:85-93). CD34+ cells are also known to differentiate into megakaryocytes in vitro and in vivo in response to recombinant TPO and TPO mimetics (de Sauvage, F. J., et al., Nature, (1994) 369: 533; Kuter, D., et al., Proc. Natl. Acad. Sci. USA (1994) 91: 11104; Erickson-Miller, C. L., et al., Exp. Hematol., (2005) 33:85). Recently, the International Application Publication Number WO2001/089457 disclosed synthetic TPO mimetic compounds for the treatment of thrombocytopenia. Such TPO mimetics have been shown to enhance platelet levels in humans in Phase I clinical trials, as described in the reference, Jenkins, J. M., et al., Blood (2007) 109:4739-4741, which illustrates that the utility of a TPO mimetic can be determined at an early stage compared to certain human therapeutics.

The present invention describes TPO mimetics that fulfill current needs and are useful as promoters of thrombopoiesis and megakaryopoiesis.

SUMMARY OF THE INVENTION

In a first aspect, the invention provides a compound described herein. In an exemplary embodiment, the compound has a structure according to a formula described herein. In another aspect, the invention is directed to a compound of Formula (I) and/or a pharmaceutically acceptable salt, solvate, and/or ester thereof:

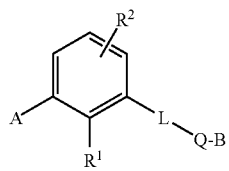

I or pharmaceutically acceptable salts, solvates and/or esters thereof, where:

A is selected from the group consisting of substituted or unsubstituted alkyl, alkenyl, aryl, cycloalkyl, heteroaryl, or a saturated or partially unsaturated heterocycloalkyl;

B is hydrogen, or substituted or unsubstituted alkyl, aryl, aralkyl, heteroaryl, cycloalkyl, heterocycloalkyl, cycloalkylalkyl, or heterocycloalkylalkyl;

Q is a five- or six-membered saturated, unsaturated, or partially unsaturated heterocycle substituted with 1 to 4 substituents $R^3$;

$R^1$ is hydrogen, hydroxy, alkoxy, carboxy, alkoxycarbonyl, aminocarbonyl, alkylaminocarbonyl, dialkylaminocarbonyl, silyloxy, acyloxy, alkylsulfonyloxy, alkylphosphonyloxy, alkoxycarbonyloxy, alkylaminocarbonyloxy, dialkylaminocarbonyloxy, —S(O)$_n$R$^4$, or —C(CF$_3$)OH (where n is 0, 1, or 2, and $R^4$ is alkyl, haloalkyl, aryl, aralkyl, heteroaryl, heteraralkyl, cycloalkyl, cycloalkylalkyl, or heterocyclyl);

$R^2$ is hydrogen, halo, cycloalkyl, (C$_{1-4}$)alkyl, alkoxy, alkenyl, carboxyalkyl, amino, acylamino, alkylamino, dialkylamino, aminoalkyl, alkylaminoalkyl, dialkylaminoalkyl, haloalkyl, cyano, or alkoxycarbonyl;

each $R^3$ is independently selected from the group consisting of hydrogen, hydroxy, alkyl, alkoxy, halo, haloalkyl, hydroxyalkyl, aminoalkyl, alkylaminoalkyl, dialkylaminoalkyl, carboxy, alkoxycarbonyl, alkoxyalkyloxy, heterocycloalkyl, heterocycloalkylalkyl, cycloalkyl, cycloalkylalkyl, cycloalkyloxy, aminocarbonylamino, alkylaminocarbonylamino, dialkylaminocarbonylamino, alkylsulfonylamino, aminocarbonyloxy, alkoxycarbonylamino cyano, alkylthio, alkylsulfonyl, cycloalkylaminoalkyl, haloalkylaminoalkyl, alkoxyalkyl, and oxo, where at least one substituent R$^3$ is oxo; and L is selected from the group consisting of azo and haloalkyleneamino;

provided that when A is substituted or unsubstituted alkyl, alkenyl, aryl, or heteroaryl, L is azo, and B is aryl or cycloalkyl, B is substituted with one or more $R^5$; where each $R^5$ is independently selected from the group consisting of acyl, alkenyl, alkoxyalkyl, alkoxyalkylamino, alkoxyalkylaminocarbonyl, alkoxyalkyloxy, alkoxyalkyloxyalkyl, alkoxyalkyloxycarbonyl, alkoxyalkyloxycarbonylalkyl, alkoxyalkylaminocarbonyl, alkoxycarbonyl, alkoxycarbonylamino, alkylamino, alkylaminoalkyl, alkylaminoalkyloxyalkyl, alkylcarbonyl, alkylcarbonylamino, alkylcarbonyloxy, alkylsulfinyl, alkyl sulfonyl, alkylsulfonylamino, alkylsulfonylaminoalkyl, alkylsulfonylaminocarbonyl, alkylthio, alkynyl, amino, aminoalkyl, aminoalkyloxy, aminocarbonyl, aminocarbonylamino, aminocarbonyloxy, aralkynyl, aralkenyl, aralkyl, aralkyloxy, aralkyloxycarbonylalkyl, aralkyloxycarbonylamino, aryl, arylaminoalkyl, arylaminocarbonyl, aryloxy, aryloxyalkyl, arylthioalkyl, carboxy, carboxyalkyl, carboxyalkylaminoalkyl, carboxyalkylaminocarbonyl, carboxyalkyloxyalkyl, cyano, cyanoalkyl, cycloalkyl, cycloalkylalkyl, cycloalkylaminocarbonyl, cycloalkylcarbonylaminoalkyl, cycloalkylcarbonyloxyalkyl, cycloalkyloxy, dialkylamino, dialkylaminoalkyl, dialkylaminoalkylamino, dialkylaminoalkyloxy, dialkylaminoalkyloxycarbonyl, dialkylaminocarbonyl, dialkylaminocarbonylalkyloxy, haloalkenyl, haloalkoxyalkyl, haloalkoxycarbonyl, haloalkylamino, haloalkylaminoalkyl, haloalkylaminocarbonyl, heteroaralkynyl, heteroaralkenyl, heteroaralkyl, heteroaralkyloxy, heteroaryl, heteroarylaminocarbonyl, heteroarylaminocarbonylalkyl, heteroaryloxyalkyl, heterocycloalkyl, heterocycloalkylalkyl, heterocycloalkylalkyloxy, heterocycloalkylalkyloxycarbonyl, heterocycloalkylaminocarbonyl, heterocycloalkyloxy, heterocycloalkyloxyalkyl, hydroxy, hydroxyalkyl, hydroxyalkylamino, hydroxyalkyloxy, hydroxyalkyloxyalkyl, and trialkylsilyl.

In a second aspect, this invention is directed to a pharmaceutical composition comprising a pharmaceutically acceptable excipient and a therapeutically effective amount of a compound described herein and/or a pharmaceutically acceptable salt, solvate, and/or ester thereof. In an exemplary embodiment, the compound has a structure according to a formula described herein. In an exemplary embodiment, the compound has a structure of Formula (I).

In a third aspect, this invention is directed to a method of treating a disease, disorder, or syndrome responsive to a TPO mimetic compound in an animal suffering from said disease, disorder, or syndrome, comprising administering to said animal a compound and/or pharmaceutical composition described herein. In another exemplary embodiment, the compound in the pharmaceutical composition is described herein and/or is a pharmaceutically acceptable salt, solvate, and/or ester thereof. In an exemplary embodiment, the compound has a structure according to a formula described herein. In an exemplary embodiment, the compound has a structure of Formula (I) and/or a pharmaceutically acceptable salt, solvate, and/or ester thereof. In an exemplary embodiment, the animal is a human.

In a fourth aspect, this invention is directed to a method of treating a disease (or disorder or condition) in an animal in need of such treatment, wherein the physiological disorder, symptom, or disease is thrombocytopenia resulting from causative factors selected from the group consisting of immune thrombocytopenic purpura, cancer chemotherapy, surgery, bone marrow or stem cell transplantation, radiation injury or treatment, severe bacterial infections, chronic viral infection, systemic lupus erythematosus, rheumatoid arthritis, and treatment with other drugs causing thrombocytopenia, which method comprises administering to said animal a compound and/or pharmaceutical composition described herein. In another exemplary embodiment, the compound in the pharmaceutical composition is described herein and/or is a pharmaceutically acceptable salt, solvate, and/or ester thereof. In an exemplary embodiment, the compound has a structure according to a formula described herein. In an exemplary embodiment, the compound has a structure of Formula (I) and/or a pharmaceutically acceptable salt, solvate, and/or ester thereof. In an exemplary embodiment, the animal is a human.

In a fifth aspect, this invention is directed to a method of treating a disease (or disorder or condition) in an animal in need of such treatment, wherein the physiological disorder, symptom, or disease is thrombocytopenia resulting from causative factors selected from the group consisting of immune thrombocytopenic purpura, cancer chemotherapy, radiation injury or treatment, bone marrow or stem cell transplantation, hepatitis C viral infection, human immunodeficiency virus infection, treatments with drugs known to cause thrombocytopenia, such as interferon-alpha, which method comprises administering to said animal a compound and/or pharmaceutical composition described herein in combination with one or more compound(s) independently selected from the group consisting of other TPO mimetics, corticosteroids, intravenous immunoglobulin, hematopoietic growth factors, cell-cycle initiators, and chemotherapeutic agents. In another exemplary embodiment, the compound in the pharmaceutical composition is described herein and/or is a pharmaceutically acceptable salt, solvate, and/or ester thereof. In an exemplary embodiment, the compound has a structure according to a formula described herein. In an exemplary embodiment, the compound has a structure of Formula (I) and/or a pharmaceutically acceptable salt, solvate, and/or ester thereof. In an exemplary embodiment, the animal is a human.

In a sixth aspect, this invention is directed to a method of treating thrombocytopenia by administering a compound and/or pharmaceutical composition described herein, in combination with other treatments such as radiation. In another exemplary embodiment, the compound in the pharmaceutical composition is described herein and/or is a pharmaceutically acceptable salt, solvate, and/or ester thereof. In an exemplary embodiment, the compound has a structure according to a formula described herein. In an exemplary embodiment, the compound has a structure of Formula (I) and/or a pharmaceutically acceptable salt, solvate, and/or ester thereof. In an exemplary embodiment, the animal is a human.

In a seventh aspect, this invention is directed to a method of treating thrombocytopenia by administering a compound and/or pharmaceutical composition described herein, in combination with surgical procedures such as splenectomy or platelet transfusion. In another exemplary embodiment, the compound in the pharmaceutical composition is described herein and/or is a pharmaceutically acceptable salt, solvate, and/or ester thereof. In an exemplary embodiment, the compound has a structure according to a formula described herein. In an exemplary embodiment, the compound has a structure of Formula (I) and/or a pharmaceutically acceptable salt, solvate, and/or ester thereof. In an exemplary embodiment, the animal is a human.

In an eighth aspect, this invention is directed to novel processes and novel intermediates that are useful in preparing a compound described herein. In an exemplary embodiment, the compound has a structure according to a formula described herein. In an exemplary embodiment, the compound has a structure according to Formula (I). In an exemplary embodiment, the animal is a human.

In a ninth aspect, this invention is directed to a method of treating a disease (or disorder or condition) in an animal in need of such treatment, wherein the physiological disorder, symptom, or disease is pancytopenia resulting from causative factors selected from the group consisting of cancer chemotherapy, radiation injury or treatment, bone marrow or stem cell transplantation, hepatitis C viral infection, human immunodeficiency virus infection, or treatments with drugs known to cause pancytopenia, which method comprises administering to said animal a compound and/or pharmaceutical composition described herein. In an exemplary embodiment, the compound has a structure according to a formula described herein. In an exemplary embodiment, the invention provides a method comprising a therapeutically effective amount of a compound of Formula (I), a pharmaceutically acceptable salt, solvate and/or ester thereof, and a pharmaceutically acceptable excipient. In an exemplary embodiment, the animal is a human.

In a tenth aspect, this invention is directed to a method of expanding stem cells and hematopoietic progenitor cells by subjecting stem cells and hematopoietic progenitor cells to a compound and/or pharmaceutical composition described herein, in an effective amount in culture or in an animal, to thereby induce the growth of the stem cells and hematopoietic progenitor cells in culture or in an animal in need of such stem cells or hematopoietic progenitor cells. In an exemplary embodiment, the compound has a structure according to a formula described herein. In an exemplary embodiment, the compound has a structure according to Formula (I). In an exemplary embodiment, the animal is a human.

Other features and advantages of the invention will be apparent from the following detailed description and from the claims.

DETAILED DESCRIPTION OF THE INVENTION

Definitions

Unless otherwise stated, the following terms used in the specification and claims are defined for the purposes of this Application and have the following meanings. When any variable occurs more than one time in any moiety, its definition on each occurrence is independent of its definition at every occurrence. A moiety (e.g., "alkyl," "aryl," "heteroaryl," etc.) described as substituted with one or more substituents (e.g., alkyl substituted with one or more hydroxyl groups), includes substitution with one, two, three, etc., substituents, provided that the resulting substituted moiety results in a stable compound (where the term "stable" has the meaning provided herein). Likewise, moieties (e.g., aryl or heteroaryl) which are described as substituted with "0 to 3" substituents include unsubstituted moieties (i.e., "0" substituents), and moieties substituted with one, two, or three such substituents, provided that the resulting substituted moiety results in a stable compound. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

"Administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., corticosteroids such as prednisone and dexamethasone, G-CSF receptor agonists, erythropoietin receptor agonists, HIV protease inhibitors, HCV protease inhibitors, intravenous immunoglobulin, cisplatin, paclitaxel, cyclophosphamide, doxorubicin, ifosfamide, etc.) "administration" and its variants are each understood to include concurrent and sequential introduction of the compound or prodrug thereof and other agents.

"Acyl" means a —C(O)R radical where R is alkyl, cyanoalkyl, haloalkyl, alkoxyalkyl, cycloalkyl, cycloalkylalkyl, aryl, aralkyl, heteroaryl, heteroaralkyl, optionally substituted heterocycloalkyl, or optionally substituted heterocycloalkylalkyl, as defined herein, e.g., acetyl, benzoyl, and the like.

"Alkenyl" means a linear monovalent hydrocarbon radical of two to six carbon atoms or a branched monovalent hydrocarbon radical of three to six carbon atoms containing one or two double bonds, e.g., ethenyl, propenyl (including all isomeric forms), 1-methylpropenyl, butenyl (including all isomeric forms), or pentenyl (including all isomeric forms) and the like. The term "alkenyl" includes substituted alkenyl which means that the alkenyl group may be substituted by one or more substituents which may be the same or different, each substituent being independently selected from the group consisting of halo, alkyl, aryl, cycloalkyl, heterocycloalkyl, heteroaryl, cyano, alkoxy, and —S(alkyl).

Alkenylene means a linear divalent hydrocarbon radical of two to six carbon atoms or a branched divalent hydrocarbon radical of three to six carbon atoms containing at least one preferably one or two, double bonds, e.g., ethen-1,2-diyl, propen-1,2-diyl, propen-1,3-diyl, or 2-methyl-but-2-en-1,4-diyl, and the like.

"Alkoxy" means a radical —OR where R is alkyl as defined herein, e.g., methoxy, ethoxy, propoxy, or 2-propoxy, n-, iso-, or tert-butoxy, and the like.

"Alkoxyalkyl" means an alkyl radical, as defined herein, substituted with at least one, preferably one or two, alkoxy group(s), as defined herein, e.g., 2-methoxyethyl, 1-, 2-, or 3-methoxypropyl, 2-ethoxyethyl, or 3,4-dimethoxybutyl, and the like.

"Alkoxyalkylamino" means a radical —NR$^a$R$^b$ where R$^a$ is hydrogen, alkyl, or alkoxyalkyl, as defined herein, and R$^b$ is alkoxyalkyl, as defined herein.

"Alkoxyalkylaminocarbonyl" means the radical —C(O)R where R is alkoxyalkylamino, as defined herein.

"Alkoxyalkylcarbonyl" means a —C(O)R radical where R is alkoxyalkyl as defined herein.

"Alkoxyalkyloxy" means a —OR radical where R is alkoxyalkyl, as defined herein.

"Alkoxyalkyloxyalkyl" means an alkyl radical substituted with at least one, preferably one or two, alkoxyalkyloxy group(s), as defined herein.

"Alkoxyalkyloxycarbonyl" means a —C(O)OR radical where R is alkoxyalkyl as defined herein.

"Alkoxyalkyloxycarbonylalkyl" means an alkyl radical substituted with at least one, preferably one or two, alkoxyalkyloxycarbonyl group(s), as defined herein.

"Alkoxyaminocarbonyl" means a —C(O)NHR radical where R is alkoxy, as defined herein, e.g. methoxyaminocarbonyl, and the like.

"Alkoxycarbonyl" means a radical —C(O)OR where R is alkyl as defined herein, e.g., methoxycarbonyl, ethoxycarbonyl, n-propyloxycarbonyl, or 2-propoxycarbonyl, n-, iso-, or tert-butoxycarbonyl, and the like.

"Alkoxycarbonylalkyl" means an alkyl radical, as defined herein, substituted with at least one, preferably one or two, alkoxycarbonyl group(s), as defined herein, e.g., methoxycarbonylmethyl, methoxycarbonylethyl, and the like.

"Alkoxycarbonylamino" means a radical —NR$^a$C(O)OR$^b$ where R$^a$ is hydrogen or alkyl, as defined herein, and R$^b$ is alkyl, as defined herein, e.g., methoxycarbonylamino, methoxycarbonyl-N-methylamino, or isopropoxycarbonylamino, and the like.

"Alkoxycarbonyloxy" means a radical —OC(O)OR where R is alkyl, as defined herein, e.g., methoxycarbonyloxy, ethoxycarbonyloxy, n-propyloxycarbonyloxy, or 2-propoxycarbonyloxy, n-, iso-, or tert-butoxycarbonyloxy, and the like.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), or pentyl (including all isomeric forms), and the like. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy, and —C(O)O-alkyl, as defined herein.

"Alkylamino" means an —NHR radical where R is alkyl as defined herein, or an N-oxide derivative, or a protected derivative thereof, e.g., methylamino, ethylamino, n-, isopropylamino, n-, iso-, tert-butylamino, or methylamino-N-oxide, and the like.

"Alkylaminoalkyl" means an alkyl radical, as defined herein, substituted with at least one, preferably one or two, alkylamino group(s), as defined herein.

"Alkylaminoalkyloxy" means an —OR radical, as defined herein, substituted with at least one, preferably one or two, alkylaminoalkyl group(s), as defined herein.

"Alkylaminoalkyloxyalkyl" means an alkyl radical, as defined herein, substituted with at 15 least one, preferably one or two, alkylaminoalkyloxy group(s), as defined herein.

"Alkylaminocarbonyl" means an —C(O)R radical where R is alkylamino as defined herein, e.g., methylaminocarbonyl or ethylaminocarbonyl, and the like.

"Alkylcarbonylamino" means a —NRR' radical, where R is hydrogen or alkyl, as defined herein, and R' is alkylcarbonyl as defined herein, e.g., methylcarbonylamino or ethylcarbonylamino, and the like.

"Alkylcarbonyloxy" means an —OR radical where R is alkyl carbonyl, as defined herein, e.g., methylcarbonyloxy, ethylcarbonyloxy, or n-propylcarbonyloxy, and the like.

"Alkylaminosulfonyl" means an —S(O)$_2$NHR radical where R is alkyl as defined herein.

"Alkylaminocarbonyloxy" means an —OR radical where R is alkylaminocarbonyl as defined herein, e.g., methylaminocarbonyloxy or ethylaminocarbonyloxy, and the like.

"Alkylene" means a linear saturated divalent hydrocarbon radical of one to six carbon atoms or as otherwise indicated or a branched saturated divalent hydrocarbon radical of two to six carbon atoms or as otherwise indicated, e.g., methylene, prop-2,2-diyl, eth-1,2-diyl, prop-1,3-diyl, 1-methylprop-1,3-diyl, 2-methylprop-1,3-diyl, but-1,4-diyl (including all isomeric forms), or pent-1,5-diyl (including all isomeric forms), and the like. Alkylene may contain the number of carbon atoms indicated. For example, the term (alkylene)$_{1-3}$ means alkylene containing from 1 carbon atom. i.e., methylene, to 3 carbon atoms, i.e., eth-1,2-diyl, eth-1,1-diyl, prop-1,3-diyl, 1-methyleth-1,2-diyl, 2-methyl-1,2-diyl, prop-1,1-diyl, and prop-2,2-diyl. The term (alkylene)$_0$ means that a bond is intended.

"Alkylphosphonyl" means an —OPO(OR)$_2$ radical where R is alkyl, as defined herein.

"Alkylsulfinyl" means an —S(O)R radical where R is alkyl as defined herein, e.g., methylsulfinyl, ethylsulfinyl, propylsulfinyl, and the like.

"Alkylsulfonyl" means an —SO$_2$R radical where R is alkyl as defined herein, e.g., methylsulfonyl, ethylsulfonyl, and the like.

"Alkylsulfonylamino" means an —NHR radical where R is an alkylsulfonyl, as defined herein, e.g., methylsulfonylamino, and the like.

"Alkylsulfonylaminoalkyl" means an alkyl radical, as defined herein, substituted with at least one, preferably one or two alkylsulfonylamino group(s), as defined herein.

"Alkylsulfonylaminocarbonyl" means a —C(O)R radical where R is alkylsulfonylamino, as defined herein.

"Alkylthio" means an —SR radical where R is alkyl, as defined herein, e.g., methylthio, ethylthio, propylthio, butylthio, and the like.

"Alkynyl" means a linear monovalent hydrocarbon radical of two to six carbon atoms or a branched monovalent hydrocarbon radical of three to six carbon atoms containing at least one, preferably one or two triple bond(s), e.g., ethynyl, propynyl (including all isomeric forms), and butynyl (including all isomeric forms), and the like. The term "substituted alkynyl" means that the alkynyl group may be substituted by one or more substituents which may be the same or different, each substituent being independently selected from the group consisting of alkyl, aryl, and cycloalkyl, as defined herein.

"Amino" means an —NH$_2$ radical or an N-oxide derivative, or a protected derivative thereof such as —NH→O, —NHBoc, or —NHCbz, and the like.

"Aminoalkyl" means an alkyl radical, as defined herein, substituted with at least one, preferably one or two, —NH$_2$ group(s), e.g., aminomethyl, aminoethyl, or 1,4-diamino-2-methylpentyl, and the like.

"Aminoalkyloxy" means an —OR radical where R is aminoalkyl as defined herein.

"Aminocarbonyl" means a —C(O)NH$_2$ radical or an N-oxide derivative, or a protected derivative thereof.

"Aminocarbonyloxy" means an —OR radical where R is aminocarbonyl as defined herein.

"Aminocarbonylamino" means an —NRC(O)NH$_2$ radical where R is hydrogen or alkyl, as defined herein.

"Animal" means a living thing such as a human, mouse, rat, cattle, deer, reindeer, goat, pig, sheep, horse, cow, bull, dog, guinea pig, gerbil, rabbit, cat, camel, yak, elephant, ostrich, otter, chicken, duck, goose, guinea fowl, pigeon, swan, and turkey. In an exemplary embodiment, the animal is a human.

"Aralkynyl" means an alkynyl radical, as defined herein, substituted with at least one, preferably, one or two, aryl group(s), as defined herein.

"Aralkyl" means an alkyl radical, as defined herein, substituted with at least one, preferably once or two, aryl group(s) as defined herein, e.g., benzyl, phenethyl, and the like.

"Aralkyloxy" means an —OR radical where R is aralkyl as defined herein, e.g., benzyloxy, 1- or 2-naphthalenemethoxy and the like.

"Aralkoxycarbonyl" means a —C(O)R radical where R is aralkoxy as defined herein.

"Aralkyloxycarbonylalkyl" means an alkyl radical, as defined herein, substituted with at least one, preferably one or two, aralkyloxycarbonyl group(s), as defined herein.

"Aralkyloxycarbonylamino" means a —NHR radical where R is aralkyloxycarbonyl, as defined herein.

"Aryl" means a monovalent, monocyclic or fused bicyclic hydrocarbon radical of 6 to 12 ring atoms, wherein the ring comprising a monocyclic radical ring is aromatic and wherein at least one of the fused rings comprising a bicyclic radical is aromatic. Unless otherwise stated, the valency of the group may be located on any atom of any ring within the radical, valency rules permitting. More specifically the term aryl includes, but is not limited to, phenyl, naphthyl, indanyl (including, for example, indan-5-yl, or indan-2-yl, and the like) or tetrahydronaphthyl (including, for example, tetrahydronaphth-1-yl, tetrahydronaphth-2-yl, and the like), and the like. Unless indicated otherwise, aryl is unsubstituted or may be substituted with one or more "ring system substituents" which may be the same or different, and are as defined herein.

"Arylaminoalkyl" means an alkyl radical substituted with —NHR where R is aryl, as defined herein.

"Arylaminocarbonyl" means a —C(O)NHR radical where R is aryl, as defined herein.

"Aryloxy" means an —OR radical where R is aryl, as defined herein.

"Aryloxyalkyl" means an alkyl radical substituted with aryloxy, as defined herein.

"Arylthioalkyl" means an alkyl radical, as defined herein, substituted with at least one, preferably one or two, —S-aryl group(s).

"Azo" means a —N=N— radical.

"Carboxy" means a —C(O)OH radical.

"Carboxyalkyl" means an alkyl radical, as defined herein, substituted with at least one, preferably one or two, —C(O)OH group(s), e.g., carboxymethyl, carboxyethyl, 1-, 2-, or 3-carboxypropyl, and the like.

"Carboxyalkylaminoalkyl" means an alkyl radical substituted with —NHR where R is carboxyalkyl, as defined herein.

"Carboxyalkylaminocarbonyl" means a —C(O)NHR radical where R is carboxyalkyl as defined herein.

"Carboxyalkylcarbonylaminoalkyl" means an alkyl radical substituted with —NHC(O)R where R is carboxyalkyl, as defined herein.

"Composition" is intended to encompass a product comprising the specified ingredients in the specified amounts, as well as any product which results, directly or indirectly, from combination of the specified ingredients in the specified amounts.

"Cyanoalkyl" means an alkyl radical, as defined herein, substituted with at least one, preferably one or two, cyano group(s), e.g., cyanomethyl, 2-cyanoethyl, or 2-cyanopropyl, and the like.

"Cycloalkyl" means a monocyclic or fused bicyclic, saturated or partially unsaturated, monovalent hydrocarbon radical of three to ten carbon ring atoms. Unless otherwise stated, the valency of the group may be located on any atom of any ring within the radical, valency rules permitting. More specifically, the term cycloalkyl includes, but is not limited to, cyclopropyl, cyclobutyl, cyclopentyl, cyclohexyl, decahydronaphthyl (including, but not limited to decahydronaphth-1-yl, decahydronaphth-2-yl, and the like), norbornyl, adamantly, or cyclohexenyl, and the like. The cycloalkyl ring is unsubstituted or may be substituted with one or more "ring system substituents" which may be the same or different, and are as defined herein.

"Cycloalkylalkyl" means an alkyl radical as defined herein, substituted with at least one, preferably one or two, cycloalkyl group(s) as defined herein, e.g., cyclopropylmethyl, cyclobutylmethyl, cyclopentylmethyl, or cyclohexylmethyl, and the like.

"Cycloalkylamino" means a —NHR radical where R is cycloalkyl as defined herein, e.g., cyclopropylamine, cyclohexylamine, and the like.

"Cycloalkylaminoalkyl" means an alkyl radical, as defined herein, substituted with at least one, preferably one or two, cycloalkylamino group(s), as defined herein.

"Cycloalkylaminocarbonyl" means a —C(O)R radical where R is cycloalkylamino as defined herein.

"Cycloalkylcarbonyl" means a —C(O)R radical where R is cycloalkyl as defined herein.

"Cycloalkylcarbonylamino" means a —$NR^aR^b$ radical where $R^a$ is cycloalkylcarbonyl, as defined herein and $R^b$ is hydrogen or alkyl, as defined herein.

"Cycloalkylcarbonylaminoalkyl" means an alkyl radical, as defined herein, substituted with at least one, preferably one or two, cycloalkylcarbonylamino group(s), as defined herein.

"Cycloalkylcarbonyloxy" means a —OC(O)R, where R is cycloalkyl, as defined above, e.g., cyclohexylcarbonyloxy, and the like.

"Cycloalkylcarbonyloxyalkyl" means an alkyl radical, as defined herein, substituted with at least one, preferably one or two, cyc 10 alkylcarbonyloxy group(s), as defined herein.

"Cycloalkyloxy" means a —OR radical where R is cycloalkyl as defined herein.

"Cycloalkylsulfonyl" means an —$SO_2R$ radical where R is cycloalkyl as defined herein, e.g., cyclopropylsulfonyl, cyclopentylsulfonyl, and the like.

"Dialkylamino" means an —NRR' radical where R and R' are independently alkyl as defined herein, or an N-oxide derivative, or a protected derivative thereof, e.g., dimethylamino, diethylamino, N,N-methylpropylamino, or N,N-methylethylamino, and the like.

"Dialkylaminoalkyl" means an alkyl radical, as defined herein, substituted with at least one, preferably one or two, dialkylamino group(s) as defined herein.

"Dialkylaminoalkylamino" means a radical —NHR where R is dialkylaminoalkyl as defined herein.

"Dialkylaminoalkyloxy" means a radical —OR where R is dialkylaminoalkyl as defined herein.

"Dialkylaminoalkyloxyalkyl" means an alkyl radical, as defined herein, substituted with at least one, preferably one or two, dialkylaminoalkyloxy group(s), as defined herein.

"Dialkylaminoalkyloxycarbonyl" means a —C(O)R radical where R is dialkylaminoalkyloxy, as defined herein.

"Dialkylaminocarbonyl" means a —C(O)R radical where R is dialkylamino as defined herein, e.g., dimethylaminocarbonyl, or N-ethyl-N-methylaminocarbonyl, and the like.

"Dialkylaminocarbonylalkyl" means an alkyl radical, as defined herein, substituted with at least one, preferably one or two, dialkylaminocarbonyl group(s), as defined herein.

"Dialkylaminocarbonylalkyloxy" means an —OR radical where R is dialkylaminocarbonylalkyl, as defined herein.

"Dialkylaminosulfonyl" means a —$S(O)_2NR'R''$ radical where R' and R'' are alkyl, as defined herein.

"Haloalkenyl" means an alkenyl radical, as defined herein, substituted with at least one, preferably one to five, halogen atoms, preferably fluorine or chlorine, including those substituted with different halogens.

"Haloalkoxy" means an —OR radical where R is haloalkyl as defined herein, e.g., trifluoromethoxy, or 2,2,2-trifluoroethoxy, and the like.

"Haloalkoxyalkyl" means an alkyl radical, as defined herein, substituted with at least one, 5 preferably one or two haloalkoxy group(s), as defined herein.

"Haloalkoxycarbonyl" means the radical —C(O)R where R is haloalkyl, as defined herein.

"Haloalkyl" means an alkyl radical, as defined herein, substituted with at least one, preferably one to five halogen atoms, preferably chlorine or fluorine, including those substituted with different halogens, e.g., —$CH_2Cl$, —$CF_3$, —$CHF_2$, —$CF_2CF_3$, —$CF(CH_3)_3$, —CHFCl, and the like.

"Haloalkylamino" means an —$NR^aR^b$ radical where $R^a$ is haloalkyl, as defined herein, and $R^b$ is hydrogen, alkyl, or haloalkyl, as defined herein, e.g., N-(trifluoromethyl)-N-(2,2-difluoroethyl)amino.

"Haloalkylaminoalkyl" means an alkyl radical substituted with haloalkylamino, as defined herein.

"Haloalkylaminocarbonyl" means a —C(O)R radical where R is haloalkylamino, as defined herein.

"Haloalkylene" means an alkylene radical, as defined herein, substituted with at least one, preferably one to five halogen atoms, preferably chlorine or fluorine, including those substituted with different halogens, e.g., —CH(Cl)—, —$CH(CF_3)$—, —$CF(CH_3)$—, —$CH(CF_2CH_3)$—, and the like.

"Haloalkyleneamino" means a divalent —$NR^aR^b$ radical where $R^a$ is haloalkylene, as defined herein, and $R^b$ is hydrogen, alkyl, or haloalkyl, as defined herein. Unless otherwise stated, the valency of the divalent group may be located on any atom within the radical, valency rules permitting. More specifically, the term includes the non-limiting examples: —$NHCH(CH_2Cl)$—, —$NHCH(CF_3)$—, —$N(CH_3)CH(CH_2CH_2CF_3)$—, —$NHCH(CF_2CF_3)$—, and the like.

"Halogen" or "halo" means fluorine, chlorine, bromine, or iodine. Preferred halogens are fluorine, chlorine and bromine.

"Heteroalkyl" means an alkyl, alkenyl or alkynyl radical as defined herein where one or more carbon atoms are replaced by an oxygen, nitrogen, phosphorous or sulphur atom for example an alkoxy group, such as methoxy, ethoxy, propoxy, iso-propoxy, butoxy or tert-butoxy, an alkoxyalkyl group such as methoxymethyl, ethoxymethyl, 1-methoxyethyl, 1-ethoxyethyl, 2-methoxyethyl or 2-ethoxyethyl, an alkylamino group such as methylamino, ethylamino, propylamino, isopropylamino, dimethylamino or diethylamino, an alkylthio group such as methylthio, ethylthio or isopropylthio or a cyano group. It may also refer to one of the above groups containing a keto group. Any heteroalkyl group as defined herein may be substituted with one, two or more substituents, for example F, Cl, Br, I, $NH_2$, OH, SH or $NO_2$.

"Heteroaralkenyl" means an alkenyl radical, as defined herein, substituted with at least one, preferably one or two, heteroaryl group(s) as defined herein.

"Heteroaralkyl" means an alkyl radical, as defined herein, substituted with at least one, preferably one or two, heteroaryl group(s) as defined herein, e.g., pyridinylmethyl, furanylmethyl, or chloropyridinylmethyl, and the like.

"Heteroaralkyloxy" means an —OR radical where R is heteroaralkyl as defined herein e.g., furanylmethyloxy or pyridinylethyloxy, and the like.

"Heteroaralkynyl" means an alkynyl radical, as defined herein, substituted with at least one, preferably, one or two, heteroaryl group(s), as defined herein.

"Heteroaryl" means a monocyclic or fused bicyclic, monovalent radical of 5 to 12 ring atoms containing one or more, preferably one, two, three, or four ring heteroatoms independently selected from the group consisting of N, O, $P(O)_m$, —Si (where Si is substituted with alkyl and one additional group selected from alkyl, alkenyl, cycloalkylalkyl, aryl, aralkyl, heteroaralkyl, and optionally substituted heterocycloalkylalkyl), and $S(O)_n$, where m is 1 or 2 and n is 0, 1, or 2, the remaining ring atoms being carbon, wherein the ring comprising a monocyclic radical is aromatic and wherein at least one of the fused rings comprising the bicyclic radical is aromatic.

One or two ring carbon atoms can optionally be replaced by a —C(O)—, —C(S)—, or C(=NH)— group. Unless otherwise stated, the valency may be located on any atom of any ring of the heteroaryl group, valency rules permitting. More specifically, the term heteroaryl includes, but is not limited to, phthalimidyl, pyridinyl, pyrrolyl, pyrazolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), pyrazinyl, pyrimidinyl, pyridazinyl, oxazolyl, isoxazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, thiazolyl, methylenedioxyphenyl (including, for example, methylenedioxyphen-5-yl), and the derivatives thereof, or N-oxide or a protected derivative thereof. The heteroaryl ring is unsubstituted or may be substituted with one, two, or three "ring system substituents" which may be the same or different, and are as defined herein.

"Heteroarylaminocarbonyl" means —C(O)NR$^a$R$^b$ where R$^a$ is hydrogen or alkyl, as defined herein, and R$^b$ is heteroaryl as defined herein.

"Heteroarylaminocarbonylalkyl" means an alkyl radical, as defined herein, substituted with at least one, preferably one or two, heteroarylaminocarbonyl group(s), as defined herein.

"Heteroaryloxyalkyl" means an alkyl radical, as defined herein, substituted with at least one, preferably one or two, heteroaryloxy group(s) as defined herein, e.g., furanyloxymethyl or pyridinyloxyethyl, and the like.

"Heterocycloalkyl" means a saturated or partially unsaturated monovalent monocyclic group of 3 to 8 ring atoms or a saturated or partially unsaturated monovalent fused bicyclic group of 5 to 12 ring atoms in which one, two, or three ring atoms are heteroatoms independently selected from the group consisting of N, O, $P(O)_m$, Si (where Si is substituted with alkyl and one additional group selected from the group consisting of alkyl, alkenyl, cycloalkylalkyl, aryl, aralkyl, heteroaralkyl, and optionally substituted heterocycloalkylalkyl), and $S(O)_n$, where m is 1 or 2 and n is 0, 1, or 2, the remaining ring atoms being C. One or two ring carbon atoms can optionally be replaced by a —C(O)—, —C(S)—, or —C(=NH)— group. Unless otherwise stated, the valency of the group may be located on any atom of any ring within the radical, valency rules permitting. More specifically the term heterocycloalkyl includes, but is not limited to, pyrrolidinyl, piperidinyl, morpholinyl, piperazinyl, homopiperazinyl, tetrahydropyranyl, 2-oxopiperidinyl, 5-oxo-4H-[1,2,4]oxadiazol-3-yl, and thiomorpholinyl, and the derivatives thereof and N-oxide or a protected derivative thereof. Unless stated otherwise, the heterocyloalkyl ring is unsubstituted or may be substituted with one, two, or three "ring system substituents" which may be the same or different, and are as defined herein.

"Heterocycloalkylalkyl" means an alkyl radical, as defined herein, substituted with at least one, preferably one or two, optionally substituted heterocycloalkyl group(s) as defined herein, e.g., piperazinylmethyl or morpholinylethyl, and the like.

"Heterocycloalkylalkyloxy" means an —OR radical where R is optionally substituted heterocycloalkylalkyl as defined herein, e.g., tetrahydropyranylmethyloxy, and the like.

"Heterocycloalkylamino" means a —NHR radical where R is heterocycloalkyl as defined herein, or an N-oxide derivative, or a protected derivative thereof, e.g., piperin-4-ylamino, tetrahydropyran-4-yl-amino, pyrrolidin-3-yl-amino, or pyrrolidin-3-yl-amino-N-oxide, and the like.

"Heterocycloalkylaminocarbonyl" means a radical —C(O)R where R is heterocycloalkylamino as defined herein.

"Heterocycloalkylalkyloxycarbonyl" means a radical —C(O)R where R is heterocycloalkylalkyloxy as defined herein.

"Heterocycloalkyloxy" means a —OR radical where R is optionally substituted heterocycloalkyl as defined herein.

"Heterocycloalkyloxyalkyl" means an alkyl radical, as defined herein, substituted with at least one, preferably one or two, optionally substituted heterocycloalkyloxy group(s), as defined.

"Hydroxyalkyl" means an alkyl radical, as defined herein, substituted with at least one, preferably one or two, hydroxy group(s), provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, or 1-(hydroxymethyl)-2-hydroxyethyl, and the like.

"Hydroxyalkylamino" means a —NHR radical where R is hydroxyalkyl as defined herein.

"Hydroxyalkyloxy" means an —OR radical where R is hydroxyalkyl, as defined herein.

"Hydroxyalkyloxyalkyl" means a —OR radical where R is hydroxyalkyloxy, as defined herein.

"Isomer" or "isomers" means compounds of Formula I having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has 2n−1 enantiomeric pairs, where n is the number of chiral centers. Compounds with more than one chiral center may exist as ether an individual diastereomer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Calm, Ingold and Prelog. Conventions for stereochemical nomenclature, methods for the determination of stereochemistry and the separation of stereoisomers are well known in the art (e.g., see "Advanced Organic Chemistry," 4th edition, March, Jerry, John Wiley & Sons, New York, 1992). It is understood that the names and illustration used in this Application to describe compounds of Formula I are meant to be encompassed all possible stereoisomers and any mixture, racemic or otherwise, thereof.

"Methylene" means a radical -$CH_2$— and the term -(methylene)$_n$- wherein n means the number of methylenes indicated and when n is 0 then a bond is intended.

"Methylenedioxy" means a radical —O—$CH_2$—O—.

"Optional" or "optionally" means that the subsequently described event or circumstance may but need not occur, and that the description includes instances where the event or circumstance occurs and instances in which it does not. For example, "heterocycloalkyl group optionally mono- or disubstituted with an alkyl group" means that the alkyl may but need not be present, and the description includes situations where the heterocycloalkyl group is mono- or disubstituted with an alkyl group and situations where the heterocycloalkyl group is not substituted with the alkyl group.

"Optionally substituted" or "may be substituted," when modifying a particular group, means that the group the term modifies may, but does not have to, be substituted. Where the term "optionally substituted" or "may be substituted" is used to modify a particular group, this does not mean, unless otherwise stated, that any other groups not so modified cannot also be optionally substituted. Furthermore, where a group is defined as being substituted by one of a number of enumerated alternative substituents, it does not mean, unless otherwise stated, that the group cannot be substituted further with one or more substituents not enumerated.

"Oxo or keto" means a carbonyl radical (=O).

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

A "pharmaceutically acceptable salt" of a compound means a salt that is pharmaceutically acceptable and that possesses the desired pharmacological activity of the parent compound. Such salts include: acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethane sulfonic acid, 1,2-ethanedisulfonic acid, 2-hydroxyethanesulfonic acid, benzene sulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

In addition, when a compound of Formula I herein contains both a basic moiety and an acidic moiety, such as, but not limited to a pyridine or imidazole, and an acidic moiety, such as, but not limited to a carboxylic acid, zwitterions ("inner salts") may be formed and are included within the term "salt(s)" as used herein.

It is understood that the pharmaceutically acceptable salts are non-toxic. Additional information on suitable pharmaceutically acceptable salts can be found in *Remington's Pharmaceutical Sciences,* 17th ed., Mack Publishing Company, Easton, Pa., 1985, which is incorporated herein by reference.

"Ring system substituent" means a substituent attached to an aromatic or non-aromatic ring system, which, for example, replaces an available hydrogen on the ring system. Ring system substituents may be the same or different, each being independently selected from the group consisting of —C(=NH)($NH_2$), —NHC(=NH)($NH_2$), alkyl, alkenyl, alkynyl, alkoxy, acyl, alkylcarbonylamino, carboxy, carboxyalkyl, alkoxycarbonyl, alkoxycarbonylalkyl, cyano, nitro, alkylthio, halo, haloalkyl, haloalkoxy, amino, alkylamino, dialkylamino, aminocarbonyl, alkyl aminocarbonyl, dialkylaminocarbonyl, alkyl sulfonyl, cycloalkylsulfonyl, alkylsulfonylamino, alkylaminosulfonyl, haloalkylamino, oxo, hydroxy, hydroxyalkyl, hydroxyalkyloxy, hydroxyalkyloxyalkyl, alkoxyalkyloxyalkyl, aryl, heteroaryl, cycloalkyl, cycloalkylamino, cycloalkyloxy, heteroaralkyloxy, aminoalkyl, aminoalkyloxy, alkoxyalkyl, alkoxyalkylcarbonyl, alkoxyalkyloxy, haloalkoxyalkyl, aryloxyalkyl, heteroaryloxyalkyl, heterocycloalkyl, heterocycloalkyloxyalkyl, heterocycloalkylalkyl, heterocycloalkylalkyloxy, heterocycloalkyloxy, -alkylene-S(O)$_n$—$R_m$ (where n is 0 to 2 and $R_m$ is alkyl, haloalkyl, hydroxyalkyl, alkoxyalkyl, aryl, heteroaryl, or heteroaralkyl), -alkylene-$NHSO_2$—$R_w$ (where $R_w$ is alkyl, haloalkyl, aryl, heteroaryl, or heteroaralkyl), -alkylene-NHC(O)—$R_q$ (where $R_q$ is alkyl, halo alkyl, aryl, heteroaryl, or heteroaralkyl), and -(methylene)$_{nl}$-C(O)$NR_fR_g$ (where nl is 0 or 1, $R_f$ is hydrogen, alkyl, or hydroxyalkyl and $R_g$ is hydrogen, alkyl, hydroxyalkyl, alkoxyalkyl, aryl, heteroaryl, heteroaralkyl, or heterocycloalkylalkyl, or $R_f$ and $R_g$ together with the nitrogen atom to which they are attached from heterocycloalkyl), and -(alkylene)$_{1-3}$-$SiR_{1-3}$ (where R is alkyl). "Ring system substituent" may also mean a single moiety that simultaneously replaces two available hydrogens on two adjacent carbon atoms (one H on each carbon) on a ring system. Examples of such moieties are methylenedioxy, ethylenedioxy, —C($CH_3$)$_2$— and the like which form moieties such as, for example:

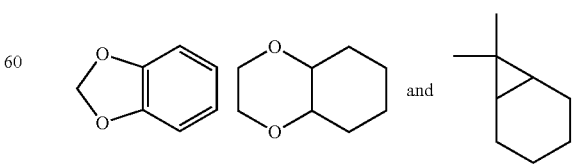

It should be noted that in hetero-atom containing ring systems of this invention, there are no hydroxyl groups on carbon atoms adjacent to a N, O, or S, as well as there are no N or S groups on carbon adjacent to another heteroatom. Thus, for example, in the ring:

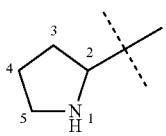

—OH is not attached directly to carbons marked 2 and 5.

It should also be noted that tautomeric forms such as, for example, the moieties:

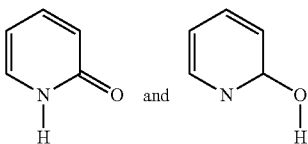

are considered equivalent in certain embodiments of this invention. Unless otherwise stated, tautomers may consist of a group of more than two equivalent forms, such as, for example, the following non-limiting moieties in certain embodiments of this invention:

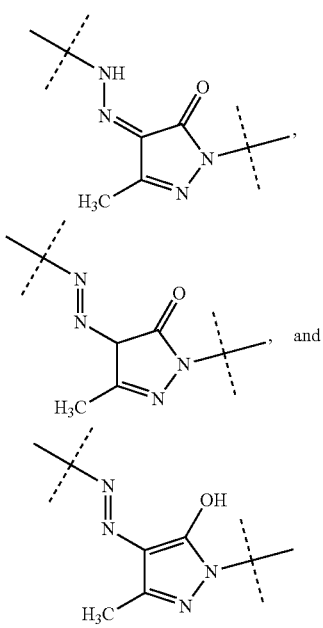

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. A "stable compound" or "stable structure" means a compound that is sufficiently robust to survive isolation to a useful degree of purity from a reaction mixture, and formulation into an efficacious therapeutic agent. "Substituted," when modifying a particular group, means that the group the term modifies must be substituted. Where the term "substituted" is used to modify a particular group, this does not mean, unless otherwise stated, that any other groups not so modified cannot be substituted. Furthermore, where a group is defined as being substituted by one of a number of enumerated alternative substituents, it does not mean, unless otherwise stated, that the group cannot be substituted further with one or more substituents not enumerated. For example, the phrase "substituted alkyl" means that the alkyl group referred to must be substituted with one or more of the substituents set forth in the definitions for "substituted alkyl."

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any heteroatom with unsatisfied valences in the text, schemes, examples, and Tables herein is assumed to have one or more hydrogen atoms to satisfy the valences.

When a ring system (e.g., cycloalkyl, heterocyclyl, aryl, or heteroaryl) is substituted with a number of substituents varying within an expressly defined range, it is understood that the total number of substituents does not exceed the normal available valencies under the existing conditions. Thus, for example, a phenyl ring substituted with "n" substituents (where "n" ranges from 0 to 5) can have 0 to 5 substituents, whereas it is understood that a pyridinyl ring substituted with "n" substituents has a number of substituents ranging from 0 to 4.

When any variable (e.g., aryl, heterocyclyl, $R^6$, etc.) occurs more than one time in any constituent or in Formula (I), its definition on each occurrence is independent of its definition at every other occurrence.

"Substituted alkenyl" means an alkenyl radical, as defined herein, substituted with one or more substituent(s), preferably one, two, or three substituents, independently selected from halo, haloalkoxy, amino, alkylamino, dialkylamino, alkoxy, hydroxy, carboxy, aminocarbonyl, alkylcarbonyl, alkylcarbonylamino-, alkylcarbonyloxy-, alkylaminocarbonyl, dialkylaminocarbonyl-, alkyl-$S(O)_n$—, alkoxycarbonyl-, alkylamino-$S(O)_n$—, dialkylamino-$S(O)_n$—, alkylaminocarbonyloxy, dialkylaminocarbonyloxy, alkoxycarbonylamino, alkylaminocarbonylamino, and dialkylaminocarbonylamino-, and where n is 0, 1, or 2.

"Substituted alkyl" means an alkyl radical, as defined herein, substituted with one or more substituent(s), preferably one, two, or three substituents, independently selected from halo, haloalkoxy, haloalkylcarbonyl, haloalkoxycarbonyl, amino, alkylamino, dialkylamino, alkoxy, hydroxy, hydroxyalkyloxy, carboxy, aminocarbonyl, alkylcarbonyl, alkylcarbonylamino, alkylcarbonyloxy, alkylaminocarbonyl, dialkylaminocarbonyl, alkyl-$S(O)_n$—, alkoxycarbonyl, alkylamino-$S(O)_n$—, dialkylamino-$S(O)_n$—, alkylaminocarbonyloxy, dialkylaminocarbonyloxy, alkylaminoalkyloxy, dialkylaminoalkyloxy, alkoxycarbonylamino, alkylaminocarbonylamino, alkoxyalkyloxy, and dialkylaminocarbonylamino, and where n is 0, 1, or 2.

"Sulfonylalkyl" means an alkyl radical, as defined herein, substituted with at least one, preferably one or two sulfonyl group(s).

A "therapeutically effective amount" means the amount of a compound of Formula I that, when administered to an animal for treating a disease, is sufficient to effect such treatment for the disease. The "therapeutically effective amount" will vary depending on the compound, the disease and its severity and the age, weight, etc., of the animal to be treated.

"Thrombocytopenia" and derivatives of as used herein means any disease or condition resulting in the decrease of blood platelets below what is considered to be normal for a healthy individual. There are several causative factors, e.g., autoimmunity, such as immune thrombocytopenic purpura; surgical procedures, such as liver or bone marrow transplantation; chronic viral infection, such as hepatitis C and human immunodeficiency virus; myelodysplastic syndrome; thrombopoietin receptor deficiency; and other potential causes as described in references such as: Kuter, D. J., Begley, C. G., *Blood,* 2002, 100, 3457 and Sekhon, S. S., Roy, V. *South. Med. J.* 2006, 99, 491. Additionally, cancer chemotherapy is known to cause thrombocytopenia, including for example, treatments with chemotherapeutics such as with vincristine, vinblastine, doxorubicin, ifosfamide, cyclophosphamide, paclitaxel, carboplatin, cisplatin, oxaliplatin, etoposide, adriamycin, gemcitabine, tamoxifen, sulindac, and the like. The pharmaceutically active compounds of this invention are also useful in treating thrombocytopenia when the causative factor or factors of the condition are unknown or have yet to be identified.

"Treating" or "treatment" of a disease, disorder, or syndrome includes:
(1) preventing the disease, disorder, or syndrome, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome;
(2) inhibiting the disease, disorder, or syndrome, i.e., arresting or reducing the development of the disease, disorder, or syndrome or its clinical symptoms; or
(3) relieving the disease, disorder, or syndrome, i.e., causing regression of the disease, disorder, or syndrome or its clinical symptoms.

"Trialkylsilyl" means a the radical —Si(R)$_3$ where R at each occurrence is independently an alkyl radical, as defined herein.

The present invention also includes the prodrugs of compounds of Formula 1. The term prodrug is intended to represent covalently bonded carriers, which are capable of releasing the active ingredient of Formula I when the prodrug is administered to an animal subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of Formula I include compounds wherein a hydroxy, amidino, guanidino, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula I), amides (e.g., trifluoroacetylamino, acetylamino, and the like), and the like. Prodrugs of compounds of Formula I are also within the scope of this invention. The present invention also includes N-oxide derivatives and protected derivatives of compounds of Formula 1. For example, when compounds of Formula I contain an oxidizable nitrogen atom, the nitrogen atom can be converted to an N-oxide by methods well known in the art. Also when compounds of Formula I contain groups such as hydroxy, carboxy, thiol or any group containing a nitrogen atom(s), these groups can be protected with a suitable protecting groups. A comprehensive list of suitable protective groups can be found in Greene, T. W., and Wuts, P. G. M. *Protecting Groups in Organic Synthesis,* John Wiley & Sons, Inc. 1999, the disclosure of which is incorporated herein by reference in its entirety. The protected derivatives of compounds of Formula I can be prepared by methods well known in the art.

The compounds of the present invention may have asymmetric centers. Compounds of the present invention containing an asymmetrically substituted atom may be isolated in optically active or racemic forms. It is well known in the art how to prepare optically active forms, such as by resolution of materials. All chiral, diastereomeric, racemic forms are within the scope of this invention, unless the specific stereochemistry or isomeric form is specifically indicated. Certain compounds of Formula I can exist as isomers. All possible isomers are within the scope of this invention. Additionally, as used herein the terms alkyl includes all the possible isomeric forms of said alkyl group albeit only a few examples are set forth. Furthermore, when the cyclic groups such as aryl, heteroaryl, heterocycloalkyl are substituted, they include all the positional isomers albeit only a few examples are set forth.

Solvates of the compounds of the invention are also contemplated herein. "Solvate" means a physical association of a compound of this invention with one or more solvent molecules. This physical association involves varying degrees of ionic and covalent bonding, including hydrogen bonding. In certain instances, the solvate will be capable of isolation, for example, when one or more solvent molecules are incorporated in the crystal lattice of the crystalline solid. "Solvate" encompasses both solution-phase and isolatable solvates. Non-limiting examples of suitable solvates include ethanolates, methanolates, and the like. A "hydrate" is a solvate wherein the solvent molecule is water.

One or more compounds of the present invention may also exist as, or optionally convert to, a solvate. Preparation of solvates is generally known. Thus, for example, M. Caira, et al., *J. Pharmaceutical Sci.,* 93(3), 601-611 (2004), describes the preparation of the solvates of the antifungal fluconazole in ethyl acetate as well as from water. Similar preparations of solvates, hemisolvate, hydrates, and the like are described by E. C. van Tonder, et al., *AAPS Pharm Sci Tech.,* 5(1), article 12 (2004); and A. L. Bingham, et al., Chem. Commun., 603-604 (2001). A typical, non-limiting process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example infrared spectroscopy, show the presence of the solvent (or water) in the crystals as a solvate (or hydrate).

Embodiments

In a first embodiment, the present invention is directed to a compound of Formula (I),

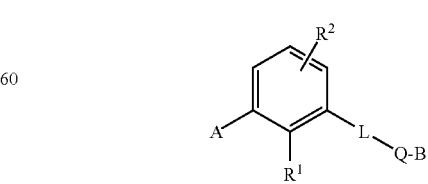

or pharmaceutically acceptable salts, solvates and/or esters thereof, where:
A is selected from the group consisting of substituted or unsubstituted alkyl, alkenyl, aryl, cycloalkyl, heteroaryl, or a saturated or partially unsaturated heterocycloalkyl;
B is hydrogen, or substituted or unsubstituted alkyl, aryl, aralkyl, heteroaryl, cycloalkyl, heterocycloalkyl, cycloalkylalkyl, or heterocycloalkylalkyl;
Q is a five- or six-membered saturated, unsaturated, or partially unsaturated heterocycle substituted with 1 to 4 substituents $R^3$;
$R^1$ is hydrogen, hydroxy, alkoxy, carboxy, alkoxycarbonyl, aminocarbonyl, alkylaminocarbonyl, dialkylaminocarbonyl, silyloxy, acyloxy, alkylsulfonyloxy, alkylphosphonyloxy, alkoxycarbonyloxy, alkylaminocarbonyloxy, dialkylaminocarbonyloxy, —S(O)$_n$R$^4$, or —C(CF$_3$)OH (where n is 0, 1, or 2, and $R^4$ is alkyl, haloalkyl, aryl, aralkyl, heteroaryl, heteraralkyl, cycloalkyl, cycloalkylalkyl, or heterocyclyl);
$R^2$ is hydrogen, halo, cycloalkyl, ($C_{1-4}$)alkyl, alkoxy, alkenyl, carboxyalkyl, amino, acylamino, alkylamino, dialkylamino, aminoalkyl, alkylaminoalkyl, dialkylaminoalkyl, haloalkyl, cyano, or alkoxycarbonyl;
each $R^3$ is independently selected from the group consisting of hydrogen, hydroxy, alkyl, alkoxy, halo, haloalkyl, hydroxyalkyl, aminoalkyl, alkylaminoalkyl, dialkylaminoalkyl, carboxy, alkoxycarbonyl, alkoxyalkyloxy, heterocycloalkyl, heterocycloalkylalkyl, cycloalkyl, cycloalkylalkyl, cycloalkyloxy, aminocarbonylamino, alkylaminocarbonylamino, dialkylaminocarbonylamino, alkylsulfonylamino, aminocarbonyloxy, alkoxycarbonylamino cyano, alkylthio, alkylsulfonyl, cycloalkylaminoalkyl, haloalkylaminoalkyl, alkoxyalkyl, and oxo, where at least one substituent $R^3$ is oxo; and
L is selected from the group consisting of azo and haloalkyleneamino;
provided that when A is substituted or unsubstituted alkyl, alkenyl, aryl, or heteroaryl, L is azo, and B is aryl or cycloalkyl, B is substituted with one or more $R^5$; where
each $R^5$ is independently selected from the group consisting of acyl, alkenyl, alkoxyalkyl, alkoxyalkylamino, alkoxyalkylaminocarbonyl, alkoxyalkyloxy, alkoxyalkyloxyalkyl, alkoxyalkyloxycarbonyl, alkoxyalkyloxycarbonylalkyl, alkoxyalkylaminocarbonyl, alkoxycarbonyl, alkoxycarbonylamino, alkylamino, alkylaminoalkyl, alkylaminoalkyloxyalkyl, alkylcarbonyl, alkylcarbonylamino, alkylcarbonyloxy, alkylsulfinyl, alkylsulfonyl, alkylsulfonylamino, alkylsulfonylaminoalkyl, alkylsulfonylaminocarbonyl, alkylthio, alkynyl, amino, aminoalkyl, aminoalkyloxy, aminocarbonyl, aminocarbonylamino, aminocarbonyloxy, aralkynyl, aralkenyl, aralkyl, aralkyloxy, aralkyloxycarbonylalkyl, aralkyloxycarbonylamino, aryl, arylaminoalkyl, arylaminocarbonyl, aryloxy, aryloxyalkyl, arylthioalkyl, carboxy, carboxyalkyl, carboxyalkylaminoalkyl, carboxyalkylaminocarbonyl, carboxyalkyloxyalkyl, cyano, cyanoalkyl, cycloalkyl, cycloalkylalkyl, cycloalkylaminocarbonyl, cycloalkylcarbonylaminoalkyl, cycloalkylcarbonyloxyalkyl, cycloalkyloxy, dialkylamino, dialkylaminoalkyl, dialkylaminoalkylamino, dialkylaminoalkyloxy, dialkylaminoalkyloxycarbonyl, dialkylaminocarbonyl, dialkylaminocarbonylalkyloxy, haloalkenyl, haloalkoxyalkyl, haloalkoxycarbonyl, haloalkylamino, haloalkylaminoalkyl, haloalkylaminocarbonyl, heteroaralkynyl, heteroaralkenyl, heteroaralkyl, heteroaralkyloxy, heteroaryl, heteroarylaminoalkyl, heteroarylaminocarbonyl, heteroarylaminocarbonylalkyl, heteroaryloxyalkyl, heterocycloalkyl, heterocycloalkylalkyl, heterocycloalkylalkyloxy, heterocycloalkyloxy-carbonyl, heterocycloalkylaminocarbonyl, heterocycloalkyloxy, heterocycloalkyloxyalkyl, hydroxy, hydroxyalkyl, hydroxyalkylamino, hydroxyalkyloxy, hydroxyalkyloxyalkyl, and trialkylsilyl.

Another embodiment of the compounds of Formula (I) is where:
Q is selected from the group consisting of

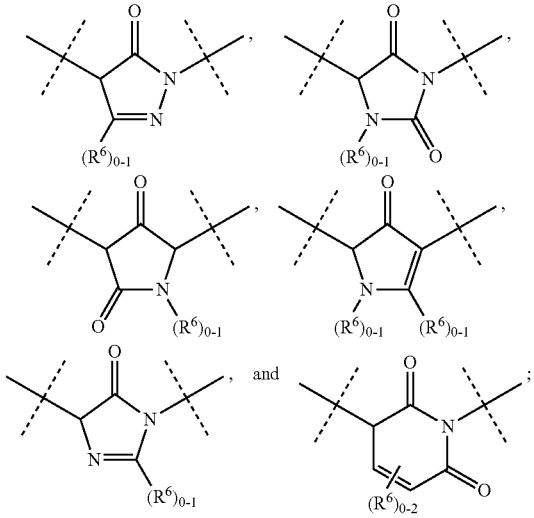

each $R^6$ is independently selected from the group consisting of hydrogen, hydroxy, alkyl, alkoxy, halo, haloalkyl, hydroxyalkyl, aminoalkyl, alkylaminoalkyl, dialkylaminoalkyl, carboxy, alkoxycarbonyl, alkoxyalkyloxy, heterocycloalkyl, heterocycloalkylalkyl, cycloalkyl, cycloalkylalkyl, cycloalkyloxy, aminocarbonylamino, alkylaminocarbonylamino, dialkylaminocarbonylamino, alkylsulfonylamino, aminocarbonyloxy, alkoxycarbonylamino cyano, alkylthio, alkylsulfonyl, cycloalkylaminoalkyl, haloalkylaminoalkyl, and alkoxyalkyl; and
L is —N═N— or —CH(R$^7$)—NH— where $R^7$ is haloalkyl optionally substituted with alkoxy and alkoxyalkyloxy;
provided that when A is substituted or unsubstituted alkyl, alkenyl, aryl, or heteroaryl, L is —N═N—, and B is aryl or cycloalkyl, and Q is the pyrazolone moiety:

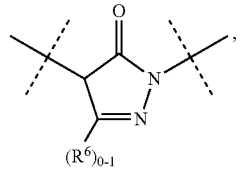

then B is substituted with one or more $R^5$; where
each $R^5$ is independently selected from the group consisting of acyl, alkenyl, alkoxyalkyl, alkoxyalkylamino, alkoxyalkylaminocarbonyl, alkoxyalkyloxy, alkoxyalkyloxyalkyl, alkoxyalkyloxycarbonyl, alkoxyalkyloxycarbonylalkyl, alkoxyalkylaminocarbonyl, alkoxycarbonyl, alkoxycarbonylamino, alkylamino, alkylaminoalkyl, alkylaminoalkyloxyalkyl, alkylcarbonyl, alkylcarbonylamino, alkylcarbonyloxy, alkylsulfinyl, alkylsulfonyl, alkylsulfonylamino, alkylsulfonylaminoalkyl, alkylsulfonylaminocarbonyl, alkylthio, alkynyl, amino, aminoalkyl, aminoalkyloxy, aminocarbonyl, aminocarbonylamino, aminocarbonyloxy, aralkynyl, aralkenyl, aralkyl, aralkyloxy, aralkyloxycarbonylalkyl, aralkyloxycarbonylamino, aryl, arylaminoalkyl, arylaminocarbonyl, aryloxy, aryloxyalkyl, arylthioalkyl, carboxy, carboxyalkyl, carboxyalkylaminoalkyl, carboxyalkylaminocarbonyl, carboxyalkyloxyalkyl, cyano, cyanoalkyl, cycloalkyl, cycloalkylalkyl, cycloalkylaminocarbonyl, cycloalkylcarbonylaminoalkyl, cycloalkylcarbonyloxyalkyl, cycloalkyloxy, dialkylamino, dialkylaminoalkyl, dialkylaminoalkylamino, dialkylaminoalkyloxy, dialkylaminoalkyloxycarbonyl, dialkylaminocarbonyl, dialkylaminocarbonylalkyloxy, haloalkenyl, haloalkoxyalkyl, haloalkoxycarbonyl, haloalkylamino, haloalkylaminoalkyl, haloalkylaminocarbonyl, heteroaralkynyl, heteroaralkenyl, heteroaralkyl, heteroaralkyloxy, heteroaryl, heteroarylaminocarbonyl, heteroarylaminocarbonylalkyl, heteroaryloxyalkyl, heterocycloalkyl, heterocycloalkylalkyl, heterocycloalkylalkyloxy, heterocycloalkylalkyloxycarbonyl, heterocycloalkylaminocarbonyl, heterocycloalkyloxy, heterocycloalkyloxyalkyl, hydroxy, hydroxyalkyl, hydroxyalkylamino, hydroxyalkyloxy, hydroxyalkyloxyalkyl, and trialkylsilyl.

Another embodiment of the compounds of Formula I is where

A is substituted or unsubstituted cycloalkyl, or a saturated or partially unsaturated heterocycloalkyl;

Q is selected from the group consisting of

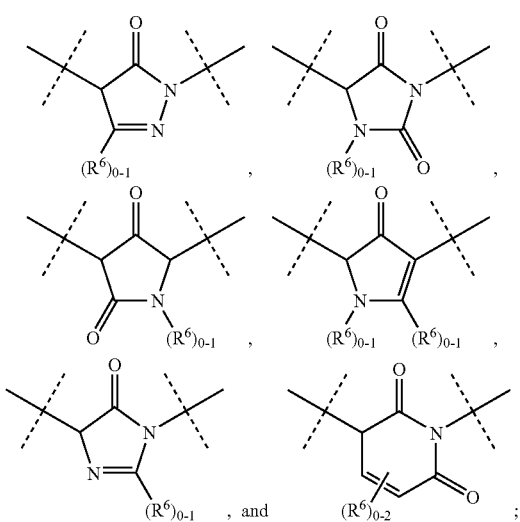

each $R^6$ is independently selected from the group consisting of hydrogen, hydroxy, alkyl, alkoxy, halo, haloalkyl, hydroxyalkyl, aminoalkyl, alkylaminoalkyl, dialkylaminoalkyl, carboxy, alkoxycarbonyl, alkoxyalkyloxy, heterocycloalkyl, heterocycloalkylalkyl, cycloalkyl, cycloalkylalkyl, cycloalkyloxy, aminocarbonylamino, alkylaminocarbonylamino, dialkylaminocarbonylamino, alkylsulfonylamino, aminocarbonyloxy, alkoxycarbonylamino cyano, alkylthio, alkylsulfonyl, cycloalkylaminoalkyl, haloalkylaminoalkyl, and alkoxyalkyl; and L is or —CH($R^7$)—NH— where $R^7$ is haloalkyl optionally substituted with alkoxy and alkoxyalkyloxy.

Another embodiment of the compounds of Formula (I) is where said compounds have a structure according to Formula II:

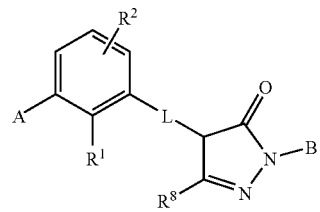

where $R^8$ is hydrogen, hydroxy, alkyl, alkoxy, hydroxyalkyl, aminoalkyl, alkylaminoalkyl, dialkylaminoalkyl, carboxy, alkoxycarbonyl, alkoxyalkyloxy, heterocycloalkyl, heterocycloalkylalkyl, cycloalkyl, cycloalkylalkyl, cycloalkyloxy, aminocarbonylamino, alkylaminocarbonylamino, dialkylaminocarbonylamino, alkylsulfonylamino, aminocarbonyloxy, alkoxycarbonylamino cyano, alkylthio, or alkylsulfonyl.

Another embodiment of the compounds of Formula (I) is where said compounds have a structure according to Formula III:

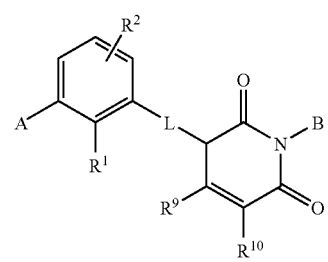

where $R^9$ and $R^{10}$ are each independently selected from the group consisting of hydrogen, hydroxy, alkyl, alkoxy, alkoxyalkyl, haloalkyl, hydroxyalkyl, aminoalkyl, alkylaminoalkyl, dialkylaminoalkyl, carboxy, alkoxycarbonyl, alkoxyalkyloxy, heterocycloalkyl, heterocycloalkylalkyl, cycloalkyl, cycloalkylalkyl, cycloalkyloxy, aminocarbonylamino, alkylaminocarbonylamino, dialkylaminocarbonylamino, alkylsulfonylamino, aminocarbonyloxy, alkoxycarbonylamino, cyano, alkylthio, cycloalkylaminoalkyl, haloalkylaminoalkyl, and alkylsulfonyl.

Another embodiment of the compounds of Formula (I) is where said compounds have a structure according to Formula IV:

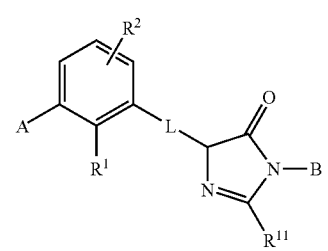

where $R^{11}$ is hydrogen, hydroxy, alkyl, alkoxy, alkoxyalkyl, haloalkyl, hydroxyalkyl, aminoalkyl, alkylaminoalkyl, dialkylaminoalkyl, carboxy, alkoxycarbonyl, alkoxyalkyloxy, heterocycloalkyl, heterocycloalkylalkyl, cycloalkyl, cycloalkylalkyl, cycloalkyloxy, aminocarbonylamino, alkylaminocarbonylamino, dialkylaminocarbonylamino, alkylsulfonylamino, aminocarbonyloxy, alkoxycarbonylamino cyano, alkylthio, cycloalkylaminoalkyl, haloalkylaminoalkyl, or alkylsulfonyl.

Another embodiment of the compounds of Formula (I) is where said compounds have a structure according to Formula V:

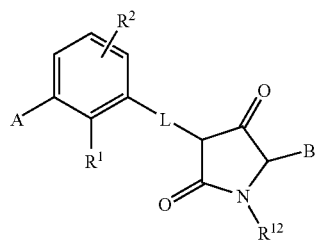

where

R$^{12}$ is hydrogen, alkyl, hydroxyalkyl, alkoxyalkyl, aminoalkyl, alkylaminoalkyl, dialkylaminoalkyl, alkoxycarbonyl, heterocycloalkyl, heterocycloalkylalkyl, cycloalkyl, cycloalkylalkyl, aminocarbonyl, alkylaminocarbonyl, dialkylaminocarbonyl, alkylsulfonyl, heteroaryl, haloalkyl, alkylsulfonyl, cycloalkylaminoalkyl, haloalkylaminoalkyl, or heterocycloalkyl.

Another embodiment of the compounds of Formula (I) is where R$^1$ is hydroxy and R$^2$ is hydrogen.

Another embodiment of the compounds of Formula (I) is where L is azo.

Another embodiment of the compounds of Formula (I) is where L is azo and where all tautomeric forms are incorporated herein, such as, for example, the following non-limiting moieties:

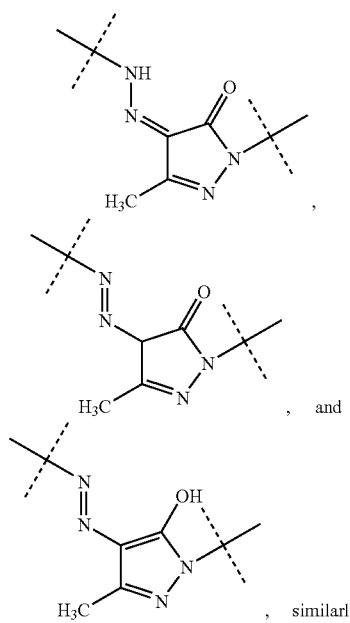

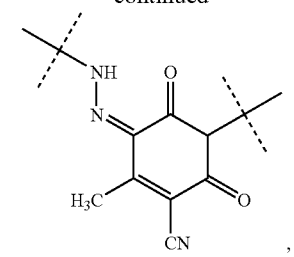

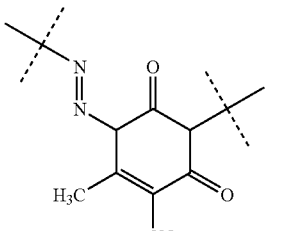

, and

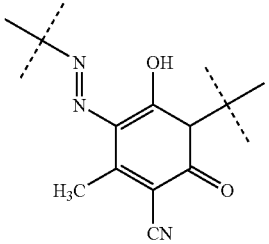

similarly,

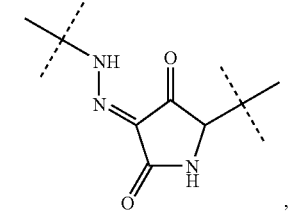

,

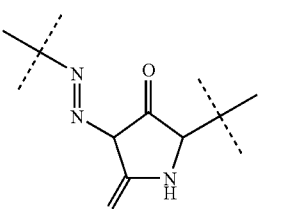

, and

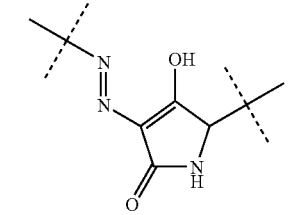

Another embodiment of the compounds of Formula (I) is where L is trifluoroethylamino.

Another embodiment of the compounds of Formula (I) is where L is trifluoroethylamino and where all isomeric forms are incorporated herein. It is intended that either the nitrogen atom may be attached to the phenyl group and the divalent carbon atom to Q as defined herein, or the divalent carbon atom may be attached to the phenyl group and the nitrogen atom to Q as defined herein, such as, for example, the following non-limiting moieties:

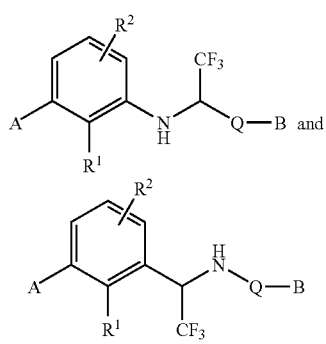

It is understood that such examples of L may exist as the R stereoisomer, the S stereoisomer, or a mixture of both, preferably, a mixture of both.

Another embodiment of the compounds of Formula (I) is where A is substituted cyclopentyl or cyclohexyl. Preferably, said cyclohexyl or cyclopentyl is substituted with one to three groups selected from the group consisting of: alkyl, alkenyl, alkynyl, alkoxy, acyl, alkylcarbonylamino, carboxy, carboxyalkyl, alkoxycarbonyl, alkoxycarbonylalkyl, cyano, nitro, alkylthio, halo, haloalkyl, haloalkoxy, amino, alkylamino, dialkylamino, aminocarbonyl, alkylaminocarbonyl, dialkylaminocarbonyl, hydroxy, hydroxyalkyl, hydroxyalkyloxy, hydroxyalkyloxyalkyl, alkoxyalkyloxyalkyl, aryl, heteroaryl, cycloalkyl, cycloalkyloxy, heteroaralkyloxy, aminoalkyl, aminoalkyloxy, alkoxyalkyl, alkoxyalkyloxy, haloalkoxyalkyl, aryloxyalkyl, heteroaryloxyalkyl, heterocycloalkyloxyalkyl, heterocycloalkylalkyl, heterocycloalkylalkyloxy, heterocycloalkyloxy, -alkylene-S(O)$_n$—R$_m$ (where n is 0 to 2 and R$_m$ is alkyl, haloalkyl, hydroxyalkyl, alkoxyalkyl, aryl, heteroaryl, or heteroaralkyl), -alkylene-NHSO$_2$—R$_w$ (where R$_w$ is alkyl, haloalkyl, aryl, heteroaryl, or heteroaralkyl), -alkylene-NHC(O)—R$_q$ (where R$_q$ is alkyl, halo alkyl, aryl, heteroaryl, or heteroaralkyl), and -(methylene)$_{nl}$-C(O)NR$_f$R$_g$ (where nl is 0 or 1, R$_f$ is hydrogen, alkyl, or hydroxyalkyl and R$_g$ is hydrogen, alkyl, hydroxyalkyl, alkoxyalkyl, aryl, heteroaryl, heteroaralkyl, or heterocycloalkylalkyl, or R$_f$ and R$_g$ together with the nitrogen atom to which they are attached from heterocycloalkyl), and -(alkylene)$_{1-3}$-SiR$_{1-3}$ (where R is alkyl). More preferably, A is substituted cyclohexyl. Even more preferably, A is cyclohexyl substituted with carboxy, ethoxycarbonyl, trifluoroethanol, tetrazole, or alkylsulfonamide. Particularly preferably, A is cyclohexyl substituted with carboxy.

Another embodiment of the compounds of Formula (I) is where A is substituted heterocycloalkyl. Preferably, said heterocycloalkyl is substituted with one to three, preferably one, group(s) selected from the group consisting of: alkyl, alkenyl, alkynyl, alkoxy, acyl, alkylcarbonylamino, carboxy, carboxyalkyl, alkoxycarbonyl, alkoxycarbonylalkyl, cyano, nitro, alkylthio, halo, haloalkyl, haloalkoxy, amino, alkylamino, dialkylamino, aminocarbonyl, alkylaminocarbonyl, dialkylaminocarbonyl, hydroxy, oxo, hydroxyalkyl, hydroxyalkyloxy, hydroxyalkyloxyalkyl, alkoxyalkyloxyalkyl, aryl, heteroaryl, cycloalkyl, cycloalkyloxy, heteroaralkyloxy, aminoalkyl, aminoalkyloxy, alkoxyalkyl, alkoxyalkyloxy, haloalkoxyalkyl, aryloxyalkyl, heteroaryloxyalkyl, heterocycloalkyloxyalkyl, heterocycloalkylalkyl, heterocycloalkylalkyloxy, heterocycloalkyloxy, -alkylene-S(O)$_n$—R$_m$ (where n is 0 to 2 and R$_m$ is alkyl, haloalkyl, hydroxyalkyl, alkoxyalkyl, aryl, heteroaryl, or heteroaralkyl), -alkylene-NHSO$_2$—R$_w$ (where R$_w$ is alkyl, haloalkyl, aryl, heteroaryl, or heteroaralkyl), -alkylene-NHC(O)—R$_q$ (where R$_q$ is alkyl, halo alkyl, aryl, heteroaryl, or heteroaralkyl), and -(methylene)$_{nl}$-C(O)NR$_f$R$_g$ (where nl is 0 or 1, R$_f$ is hydrogen, alkyl, or hydroxyalkyl and R$_g$ is hydrogen, alkyl, hydroxyalkyl, alkoxyalkyl, aryl, heteroaryl, heteroaralkyl, or heterocycloalkylalkyl, or R$_f$ and R$_g$ together with the nitrogen atom to which they are attached from heterocycloalkyl), and -(alkylene)$_{1-3}$-SiR$_{1-3}$ (where R is alkyl). More preferably, A is piperidino or 1-methyl-1-oxo-1λ$^5$-phosphinane. Even more preferably, A is piperidino substituted with carboxymethyl, ethoxycarbonylmethyl, cyclopropyl, or 2,2,2-trifluoroethyl. Particularly preferably, A is piperidino substituted with carboxymethyl.

Another embodiment of the compounds of Formula (I) is where A is substituted cycloalkyl or saturated or partially unsaturated heterocycloalkyl and B is aryl, cycloalkyl, or heterocycloalkyl. Preferably, B is substituted aryl or substituted heterocycloalkyl, and said aryl or heterocycloalkyl is substituted with one to three, preferably one or two, group(s) selected from the group consisting of: alkyl, alkenyl, alkynyl, alkoxy, acyl, alkylcarbonylamino, carboxy, carboxyalkyl, alkoxycarbonyl, alkoxycarbonylalkyl, cyano, nitro, alkylthio, halo, haloalkyl, haloalkoxy, amino, alkylamino, dialkylamino, aminocarbonyl, alkylaminocarbonyl, dialkylaminocarbonyl, hydroxy, hydroxyalkyl, hydroxyalkyloxy, hydroxyalkyloxyalkyl, alkoxyalkyloxyalkyl, aryl, heteroaryl, cycloalkyl, cycloalkyloxy, heteroaralkyloxy, aminoalkyl, aminoalkyloxy, alkoxyalkyl, alkoxyalkyloxy, haloalkoxyalkyl, aryloxyalkyl, heteroaryloxyalkyl, heterocycloalkyloxyalkyl, heterocycloalkylalkyl, heterocycloalkylalkyloxy, heterocycloalkyloxy, -alkylene-S(O)$_n$—R$_m$ (where n is 0 to 2 and R$_m$ is alkyl, haloalkyl, hydroxyalkyl, alkoxyalkyl, aryl, heteroaryl, or heteroaralkyl), -alkylene-NHSO$_2$—R$_w$ (where R$_w$ is alkyl, haloalkyl, aryl, heteroaryl, or heteroaralkyl), -alkylene-NHC(O)—R$_q$ (where R$_w$ is alkyl, halo alkyl, aryl, heteroaryl, or heteroaralkyl), and -(methylene)$_{nl}$-C(O)NR$_f$R$_g$ (where nl is 0 or 1, R$_f$ is hydrogen, alkyl, or hydroxyalkyl and R$_g$ is hydrogen, alkyl, hydroxyalkyl, alkoxyalkyl, aryl, heteroaryl, heteroaralkyl, or heterocycloalkylalkyl, or R$_f$ and R$_g$ together with the nitrogen atom to which they are attached from heterocycloalkyl), and -(alkylene)$_{1-3}$-SiR$_{1-3}$ (where R is alkyl). More preferably, B is 3,4-dimethylphenyl, 1-methyl-1-oxo-1λ$^5$-phosphinane, 1-(2,2,2-trifluoroethyl)piperidine, or 1-cyclopropylpiperidine. Even more preferably, B is 3,4-dimethylphenyl.

In another embodiment of the compounds of Formula (I), Q is pyrazolone.

In an exemplary embodiment, the compound has a structure which is a member selected from the following formulae:

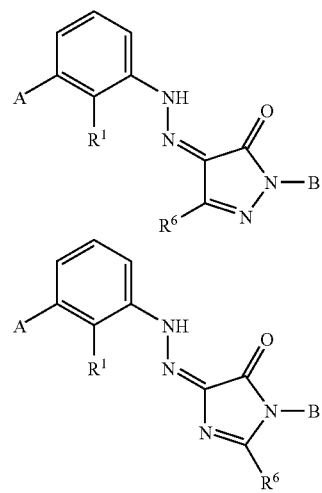

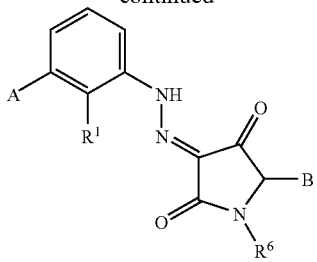

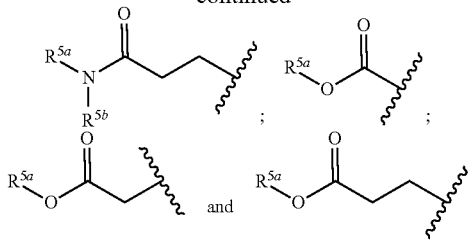

wherein A is a member selected from substituted or unsubstituted cycloalkyl and substituted or unsubstituted heterocycloalkyl, $R^1$ is a member selected from hydrogen, hydroxy, alkoxy, and carboxy, $R^6$ is a member selected from hydrogen, and substituted or unsubstituted alkyl, and B is a member selected from substituted or unsubstituted cycloalkyl, substituted or unsubstituted heterocycloalkyl, substituted or unsubstituted aryl and substituted or unsubstituted heteroaryl. In an exemplary embodiment, $R^1$ is a member selected from OH and $OR^{1a}$, wherein $R^{1a}$ is a member selected from a negative charge and a salt counterion. In an exemplary embodiment, $R^6$ is a member selected from substituted or unsubstituted alkyl. In an exemplary embodiment, $R^6$ is a member selected from substituted or unsubstituted methyl, substituted or unsubstituted ethyl, substituted or unsubstituted propyl, substituted or unsubstituted butyl, substituted or unsubstituted pentyl. In an exemplary embodiment, $R^6$ is a member selected from methyl, ethyl, propyl, butyl and pentyl. In an exemplary embodiment, $R^1$ is a member selected from OH and $OR^{1a}$, wherein $R^{1a}$ is a member selected from a negative charge and a salt counterion and $R^6$ is a member selected from substituted or unsubstituted alkyl.

In an exemplary embodiment, A is a member selected from substituted or unsubstituted cyclohexyl, substituted or unsubstituted piperidinyl, substituted or unsubstituted 1,2,3,6-tetrahydropyridinyl, substituted or unsubstituted pyrrolidinyl, substituted or unsubstituted 1-oxo phosphinanyl and substituted or unsubstituted 1,1 dioxo tetrahydrothiopyranyl. In an exemplary embodiment, A is a member selected from substituted cyclohexyl, substituted piperidinyl, substituted 1,2,3,6-tetrahydropyridinyl, substituted pyrrolidinyl, substituted 1-oxo phosphinanyl and substituted 1,1 dioxotetrahydrothiopyranyl. In an exemplary embodiment, A is substituted with a moiety which is a member selected from hydroxyl, substituted or unsubstituted cyclopropyl, substituted or unsubstituted alkyl,

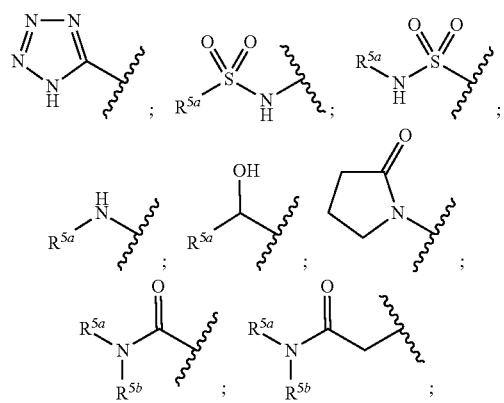

wherein each $R^{5a}$ and $R^{5b}$ is a member independently selected from H, substituted or unsubstituted alkyl and substituted or unsubstituted heteroalkyl, or $R^{5a}$ and $R^{5b}$ together with the nitrogen atom to which they are attached from are heterocycloalkyl.

In an exemplary embodiment, A is substituted with a moiety which is a member selected from hydroxyl, unsubstituted cyclopropyl, substituted or unsubstituted alkyl,

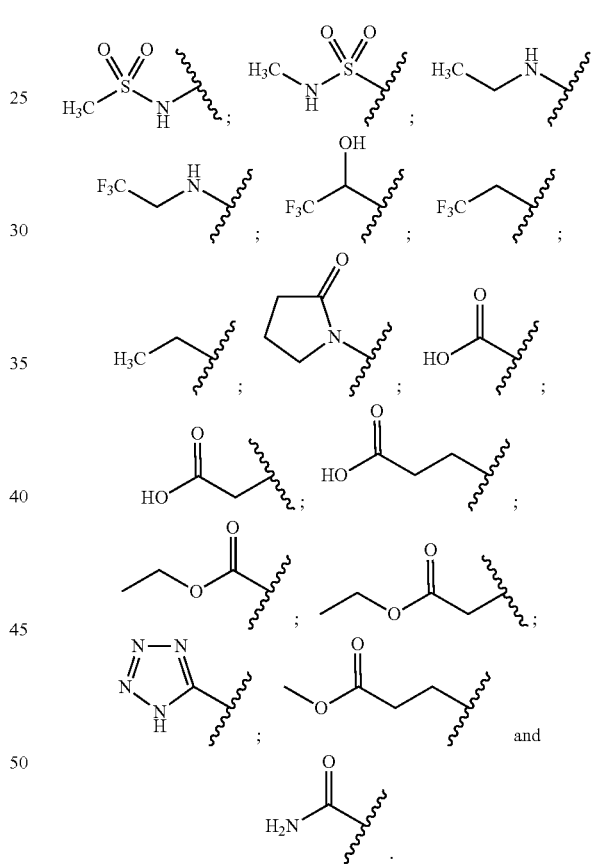

In another exemplary embodiment, B is a member selected from substituted or unsubstituted aryl, substituted or unsubstituted heteroaryl, substituted or unsubstituted cycloalkyl, substituted or unsubstituted heterocycloalkyl. In another exemplary embodiment, B is a member selected from substituted or unsubstituted phenyl, substituted or unsubstituted cyclohexyl, substituted or unsubstituted pyridinyl, substituted or unsubstituted azetidinyl, substituted or unsubstituted piperidinyl, substituted or unsubstituted 1,2,3,6-tetrahydropyridinyl, substituted or unsubstituted pyrrolidinyl, substituted or unsubstituted t-oxo phosphinanyl, substituted or unsubstituted 1,1 dioxotetrahydrothiopyranyl, substituted or unsubstituted tetrahydropyranyl, substituted or unsubstituted thiophenyl, substituted or unsubstituted cyclopentyl and substituted or unsubstituted cycloheptenyl.

In another exemplary embodiment, B is a member selected from unsubstituted 2-thiophenyl, unsubstituted 3-thiophenyl, unsubstituted pyridinyl, unsubstituted pyranyl, unsubstituted cyclopentyl, unsubstituted cyclohexyl and unsubstituted cycloheptyl. In another exemplary embodiment, B is a member selected from substituted phenyl, substituted pyridinyl, substituted azetidinyl, substituted piperidinyl, substituted 1,2,3,6-tetrahydropyridinyl, substituted pyrrolidinyl, substituted 1-oxo phosphinanyl, substituted 1,1 dioxotetrahydrothiopyranyl and substituted tetrahydropyranyl.

In an exemplary embodiment, B is monosubstituted with a moiety which is a member selected from hydroxyl, substituted or unsubstituted alkyl, substituted or unsubstituted dialkylamino, halogen, substituted or unsubstituted cycloalkyl, substituted or unsubstituted alkyloxy,

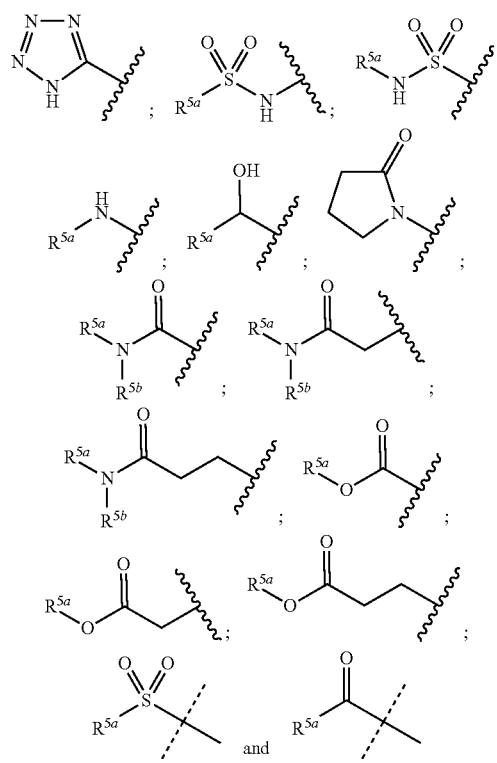

wherein each $R^{5a}$ and $R^{5b}$ is a member independently selected from H, substituted or unsubstituted alkyl, substituted or unsubstituted cycloalkyl and substituted or unsubstituted heteroalkyl, or $R^{5a}$ and $R^{5b}$ together with the nitrogen atom to which they are attached from heterocycloalkyl.

In an exemplary embodiment, B is disubstituted with moieties which are members independently selected from hydroxyl, substituted or unsubstituted alkyl, substituted or unsubstituted dialkylamino, halogen, substituted or unsubstituted cycloalkyl, substituted or unsubstituted alkyloxy,

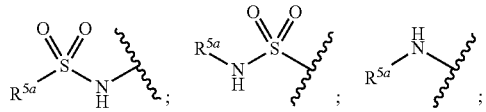

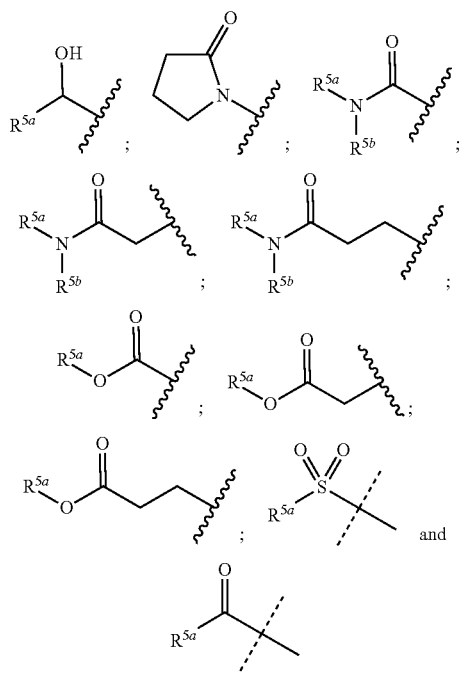

In an exemplary embodiment, B is a phenyl which is disubstituted with moieties which are members independently selected from substituted or unsubstituted alkyl and halogen. In an exemplary embodiment, B is a member selected from

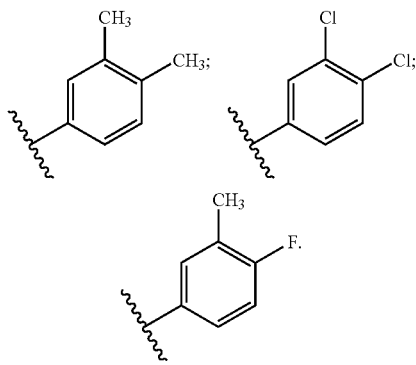

In an exemplary embodiment, B is a member selected from

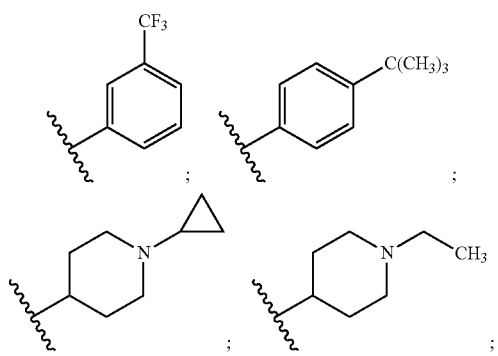

-continued

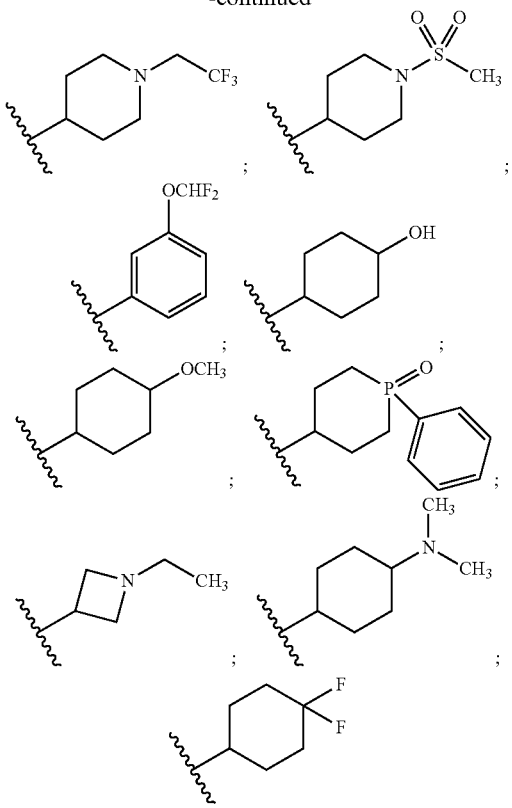

In an exemplary embodiment, the compound has a structure according to the following formula:

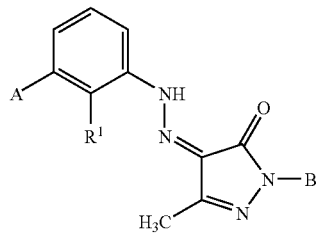

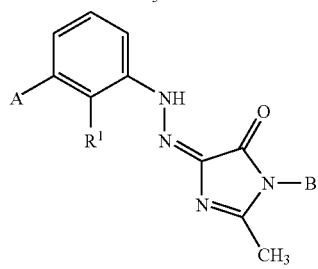

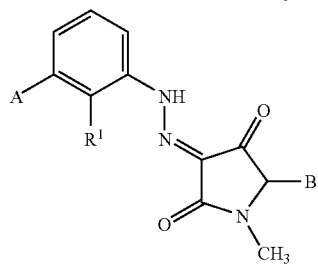

wherein $R^1$ is a member selected from OH and $OR^{1a}$, wherein $R^{1a}$ is a member selected from a negative charge and a salt counterion, and wherein A and B are as described herein. In an exemplary embodiment, A is a member selected from substituted or unsubstituted cyclohexyl, substituted or unsubstituted piperidinyl, substituted or unsubstituted 1,2,3,6-tetrahydropyridinyl, substituted or unsubstituted pyrrolidinyl, substituted or unsubstituted 1-oxo phosphinanyl and substituted or unsubstituted 1,1 dioxotetrahydrothiopyranyl. In another exemplary embodiment, B is a member selected from substituted or unsubstituted aryl, substituted or unsubstituted heteroaryl, substituted or unsubstituted cycloalkyl, substituted or unsubstituted heterocycloalkyl. In another exemplary embodiment, B is a member selected from substituted or unsubstituted phenyl, substituted or unsubstituted cyclohexyl, substituted or unsubstituted pyridinyl, substituted or unsubstituted azetidinyl, substituted or unsubstituted piperidinyl, substituted or unsubstituted 1,2,3,6-tetrahydropyridinyl, substituted or unsubstituted pyrrolidinyl, substituted or unsubstituted t-oxo phosphinanyl, substituted or unsubstituted 1,1 dioxotetrahydrothiopyranyl, substituted or unsubstituted tetrahydropyran, substituted or unsubstituted thiophenyl, substituted or unsubstituted cyclopentyl and substituted or unsubstituted cycloheptenyl.

In an exemplary embodiment, the compound has a structure according to the following formula:

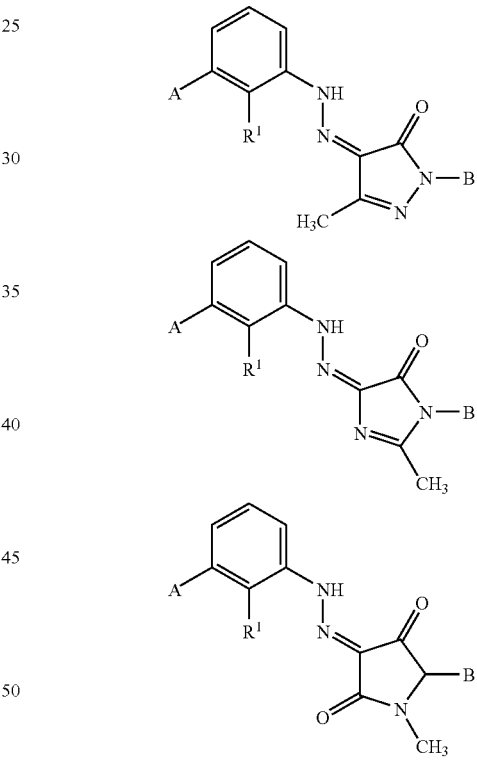

wherein $R^1$ is a member selected from OH and $OR^{1a}$, wherein $R^{1a}$ is a member selected from a negative charge and a salt counterion, and A and B are as defined herein. In an exemplary embodiment, A is a member selected from substituted or unsubstituted cyclohexyl and substituted or unsubstituted piperidinyl. In an exemplary embodiment, A is a member selected from unsubstituted cyclohexyl,

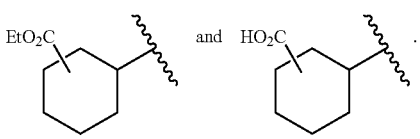

In an exemplary embodiment, A is a member selected from

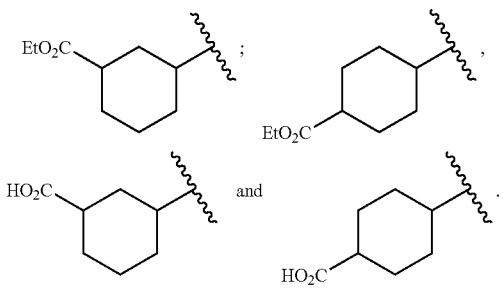

In an exemplary embodiment, B is a member selected from substituted and unsubstituted phenyl. In another exemplary embodiment, B is a substituted phenyl. In another exemplary embodiment, B is a member selected from

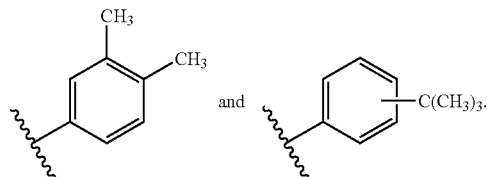

In an exemplary embodiment, the compound has a structure according to the following formula:

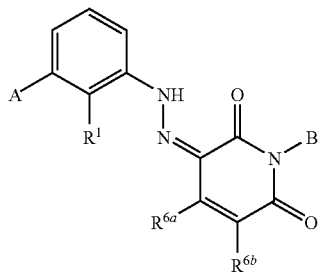

wherein A is a member selected from substituted or unsubstituted cycloalkyl and substituted or unsubstituted heterocycloalkyl, $R^1$ is a member selected from hydrogen, hydroxy, alkoxy, and carboxy, $R^{6a}$ is a member selected from hydrogen, hydroxy, substituted or unsubstituted alkyl, and alkoxy, and $R^{6b}$ is a member selected from hydrogen, hydroxy, substituted or unsubstituted alkyl, substituted or unsubstituted aryl, and cyano, and B is a member selected from substituted or unsubstituted cycloalkyl, substituted or unsubstituted heterocycloalkyl, substituted or unsubstituted aryl and substituted or unsubstituted heteroaryl. In an exemplary embodiment, $R^1$ is a member selected from OH and $OR^{1a}$, wherein $R^{1a}$ is a member selected from a negative charge and a salt counterion. In an exemplary embodiment, $R^{6a}$ is a member selected from substituted or unsubstituted alkyl. In an exemplary embodiment, $R^{6a}$ is a member selected from substituted and unsubstituted methyl, substituted and unsubstituted ethyl, substituted and unsubstituted propyl, substituted and unsubstituted butyl, substituted and unsubstituted pentyl. In an exemplary embodiment, $R^{6a}$ is a member selected from methyl, ethyl, propyl, butyl and pentyl. In an exemplary embodiment, $R^{6b}$ is a member selected from H, cyano, substituted or unsubstituted alkyl and substituted or unsubstituted heteroalkyl. In an exemplary embodiment, $R^{6b}$ has a structure which is a member selected from

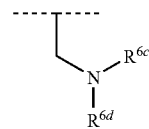

wherein $R^{6c}$ and $R^{6d}$ are each members independently selected from H, substituted or unsubstituted alkyl, substituted or unsubstituted cycloalkyl, substituted or unsubstituted heteroalkyl with the proviso that $R^{6c}$ and $R^{6d}$ are optionally joined together to form a 5-7 membered ring. In an exemplary embodiment, $R^{6b}$ is a member selected from

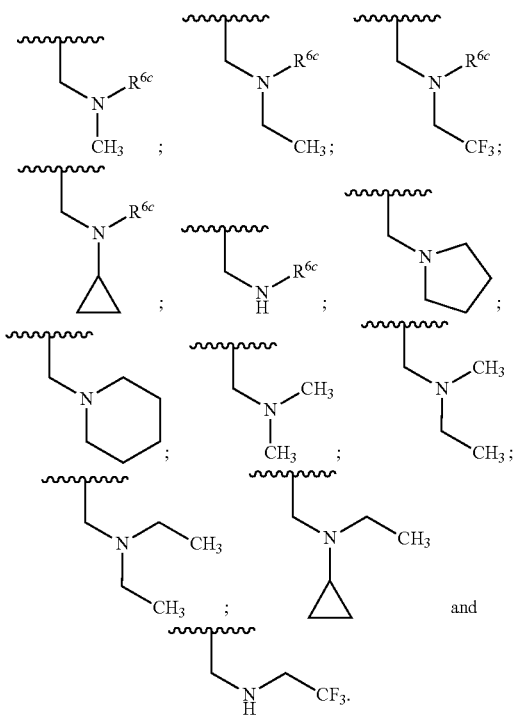

In an exemplary embodiment, the invention provides a compound having a structure according to the following formula:

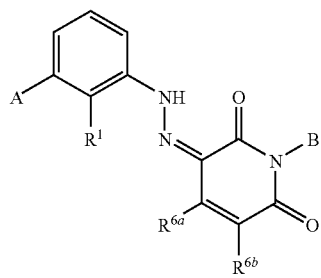

wherein $R^1$ is a member selected from OH and $OR^{1a}$, wherein $R^{1a}$ is a member selected from a negative charge and a salt counterion, and A, B and $R^{6b}$ are as defined herein. In an exemplary embodiment, $R^{6a}$ is a member selected from substituted or unsubstituted alkyl. In an exemplary embodiment, $R^{6a}$ is a member selected from substituted or unsubstituted methyl, substituted or unsubstituted ethyl, substituted or unsubstituted propyl, substituted or unsubstituted butyl, substituted or unsubstituted pentyl. In an exemplary embodiment, $R^{6a}$ is a member selected from methyl, ethyl, propyl, butyl and pentyl. In an exemplary embodiment, $R^{6a}$ is unsubstituted methyl. In an exemplary embodiment, $R^{6a}$ is unsubstituted methyl, and A is a member selected from substituted or unsubstituted cyclohexyl and substituted or unsubstituted piperidinyl. In an exemplary embodiment, $R^{ha}$ is unsubstituted methyl, and B is a member selected from substituted or unsubstituted aryl and substituted or unsubstituted cyclohexyl.

In an exemplary embodiment, the compound has a structure which is a member selected from the following formulae:

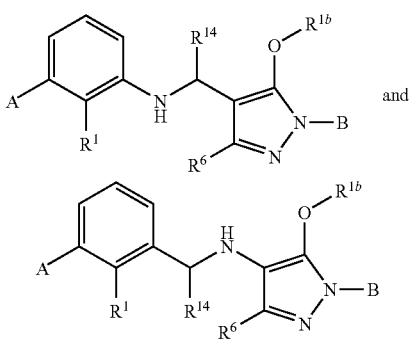

wherein A is a member selected from substituted or unsubstituted cycloalkyl and substituted or unsubstituted heterocycloalkyl, $R^1$ is a member selected from hydrogen, hydroxy, alkoxy, and carboxy, $R^6$ is a member selected from hydrogen and substituted or unsubstituted alkyl, B is a member selected from substituted or unsubstituted cycloalkyl, substituted or unsubstituted heterocycloalkyl, substituted or unsubstituted aryl and substituted or unsubstituted heteroaryl, $R^{14}$ is a member selected from substituted or unsubstituted alkyl and $R^{1b}$ is a member selected from H, a negative charge and a salt counterion. In an exemplary embodiment, $R^1$ is a member selected from OH and $OR^1$, wherein $R^{1a}$ is a member selected from a negative charge and a salt counterion. In an exemplary embodiment, $R^6$ is a member selected from substituted or unsubstituted alkyl. In an exemplary embodiment, $R^6$ is a member selected from substituted or unsubstituted methyl, substituted or unsubstituted ethyl, substituted or unsubstituted propyl, substituted or unsubstituted butyl, substituted or unsubstituted pentyl. In an exemplary embodiment, $R^6$ is a member selected from methyl, ethyl, propyl, butyl and pentyl. In an exemplary embodiment, $R^1$ is a member selected from OH and $OR^{1a}$, wherein $R^{1a}$ is a member selected from a negative charge and a salt counterion and $R^6$ is a member selected from substituted or unsubstituted alkyl. In an exemplary embodiment, $R^{14}$ is a substituted alkyl. In another exemplary embodiment, $R^{14}$ is an alkyl moiety which is substituted with at least one halogen. In another exemplary embodiment, $R^{14}$ is an alkyl moiety which is substituted with at least one fluorine or chlorine. In another exemplary embodiment, $R^{14}$ is an alkyl moiety which is substituted with at least two halogens. In another exemplary embodiment, $R^{14}$ is a member selected from:

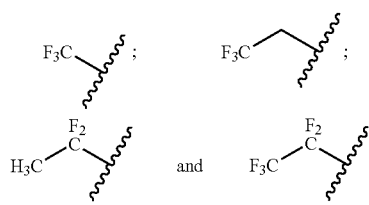

In an exemplary embodiment, the compound is a member described herein. In an exemplary embodiment, the compound has a structure according to a formula described herein. In an exemplary embodiment, the compound is a member selected from 4-[2-(3-cyclohexyl-2-hydroxyphenyl)hydrazin-1-ylidene]-1-(3,4-dimethylphenyl)-3-methyl-4,5-dihydro-1H-pyrazol-5-one; 4-[2-(3-cyclohexyl-2-hydroxyphenyl)hydrazin-1-ylidene]-1-(4-tert-butylphenyl)-3-methyl-4,5-dihydro-1H-pyrazol-5-one; 3-(3'-{2-[1-(3,4-dimethylphenyl)-3-methyl-5-oxo-4,5-dihydro-1H-pyrazol-4-ylidene]hydrazino}-2'-hydroxy-phenyl)cyclohexane-1-carboxylic acid; 3-(3'-{2-[1-(4-tert-butylphenyl)-3-methyl-5-oxo-4,5-dihydro-1H-pyrazol-4-ylidene]hydrazino}-2'-hydroxy-phenyl)cyclohexane-1-carboxylic acid; 3-(3'-{2-[1-(3,4-dimethylphenyl)-3-methyl-5-oxo-4,5-dihydro-1H-pyrazol-4-ylidene]hydrazino}-2'-hydroxy-phenyl)cyclohexane-1-carboxylic acid ethyl ester; 1-(3,4-dimethylphenyl)-4-{2-[2-hydroxy-3-(1-methylpiperidin-4-yl)phenyl]hydrazin-1-ylidene}-3-methyl-4,5-dihydro-1H-pyrazol-5-one.

In an additional embodiment, the compound is a member selected from: 3-(3'-{2-[1-(3,4-dimethylphenyl)-3-methyl-5-oxo-4,5-dihydro-1H-pyrazol-4-ylidene]hydrazino}-2'-hydroxy-phenyl)cyclohexane-1-carboxylic acid; 3-(3'-{2-[1-(3,4-dimethylphenyl)-3-methyl-5-oxo-4,5-dihydro-1H-pyrazol-4-ylidene]hydrazino}-2'-hydroxy-phenyl)cyclohexane-1-carboxylic acid ethyl ester; 3-(3'-{2-[1-(3,4-dimethylphenyl)-3-methyl-5-oxo-4,5-dihydro-1H-pyrazol-4-ylidene]hydrazino}-2'-hydroxy-phenyl)cyclopentane-1-carboxylic acid; 2-(3'-{2-[1-(3,4-dimethylphenyl)-3-methyl-5-oxo-4,5-dihydro-1H-pyrazol-4-ylidene]hydrazino}-2'-hydroxy-phenyl)cyclohexane-1-carboxylic acid; 3-(3'-{2-[1-(3,4-dimethylphenyl)-3-methyl-5-oxo-4,5-dihydro-1H-pyrazol-4-ylidene]hydrazino}-2'-hydroxy-phenyl)-1-(1H-tetrazol-5-yl)cyclohexane; 1-(3,4-dimethylphenyl)-4-(2-{2-hydroxy-3-[3-(2,2,2-trifluoro-1-hydroxyethyl)cyclohexyl]phenyl}hydrazin-1-ylidene)-3-methyl-4,5-dihydro-1H-pyrazol-5-one; 1-(3,4-dimethylphenyl)-4-{2-[2-hydroxy-3-(4-hydroxycyclohexyl)phenyl]hydrazin-1-ylidene}-3-methyl-4,5-dihydro-1H-pyrazol-5-one; 4-(3'-{2-[1-(3,4-dimethylphenyl)-3-methyl-5-oxo-4,5-dihydro-1H-pyrazol-4-ylidene]hydrazino}-2'-hydroxy-phenyl)cyclohexane-1-carboxylic acid; 4-(3'-{2-[1-(3,4-dimethylphenyl)-3-methyl-5-oxo-4,5-dihydro-1H-pyrazol-4-ylidene]hydrazino}-2'-hydroxy-phenyl)piperidin-1-yl-acetic acid; 4-(3'-{2-[1-(3,4-dimethylphenyl)-3-methyl-5-oxo-4,5-dihydro-1H-pyrazol-4-ylidene]hydrazino}-2'-hydroxy-phenyl)piperidin-1-yl-acetic acid ethyl ester; 4-(2-{3-[3-(cyclopropylamino)cyclohexyl]-2-hydroxyphenyl}hydrazin-1-ylidene)-1-(3,4-dimethylphenyl)-3-methyl-4,5-dihydro-1H-pyrazol-5-one; and 1-(3,4-dimethylphenyl)-4-(2-{2-hydroxy-3-[3-(2-oxopyrrolidin-1-yl)cyclohexyl]phenyl}hydrazin-1-ylidene)-3-methyl-4,5-dihydro-1H-pyrazol-5-one.

In an additional embodiment, the compound is a member selected from: N-[4-(3-{2-[1-(3,4-dimethylphenyl)-3-methyl-5-oxo-4,5-dihydro-1H-pyrazol-4-ylidene]hydrazin-1-yl}-2-hydroxyphenyl)cyclohexyl]methanesulfonamide;

4-(3-{2-[1-(3,4-dimethylphenyl)-3-methyl-5-oxo-4,5-dihydro-1H-pyrazol-4-ylidene]hydrazin-1-yl}-2-hydroxyphenyl)-N-methylcyclohexane-1-sulfonamide; 1-(3,4-dimethylphenyl)-4-[2-(2-hydroxy-3-{3-[(2,2,2-trifluoroethyl)amino]cyclohexyl}phenyl)hydrazin-1-ylidene]-3-methyl-4,5-dihydro-1H-pyrazol-5-one; 4-{2-[3-(1-cyclopropylpiperidin-3-yl)-2-hydroxyphenyl]hydrazin-1-ylidene}-1-(3,4-dimethylphenyl)-3-methyl-4,5-dihydro-1H-pyrazol-5-one; 2-[4-(3-{2-[1-(3,4-dimethylphenyl)-3-methyl-5-oxo-4,5-dihydro-1H-pyrazol-4-ylidene]hydrazin-1-yl}-2-hydroxyphenyl)-1,2,3,6-tetrahydropyridin-1-yl]acetic acid; 2-[4-(3-{2-[1-(3,4-dimethylphenyl)-3-methyl-5-oxo-4,5-dihydro-1H-pyrazol-4-ylidene]hydrazin-1-yl}-2-hydroxyphenyl)-1,2,3,6-tetrahydropyridin-1-yl]acetic acid ethyl ester; 3-(3-{2-[1-(3,4-dimethylphenyl)-3-methyl-5-oxo-4,5-dihydro-1H-pyrazol-4-ylidene]hydrazin-1-yl}-2-hydroxyphenyl)-1-hydroxycyclohexane-1-carboxylic acid; 3-(3-{2-[1-(3,4-dimethylphenyl)-3-methyl-5-oxo-4,5-dihydro-1H-pyrazol-4-ylidene]hydrazin-1-yl}-2-hydroxyphenyl)piperidine-1-carboxamide; 4-{2-[3-(1-cyclopropylpiperidin-4-yl)-2-hydroxyphenyl]hydrazin-1-ylidene}-1-(3,4-dimethylphenyl)-3-methyl-4,5-dihydro-1H-pyrazol-5-one; 1-(3,4-dimethylphenyl)-4-(2-{2-hydroxy-3-[1-(2,2,2-trifluoroethyl)piperidin-4-yl]phenyl}hydrazin-1-ylidene)-3-methyl-4,5-dihydro-1H-pyrazol-5-one; and 1-methyl-1-oxo-4-(3'-{2-[1-(3,4-dimethylphenyl)-3-methyl-5-oxo-4,5-dihydro-1H-pyrazol-4-ylidene]hydrazino}-2'-hydroxyphenyl)-1$\lambda^5$-phosphinane.

In an additional embodiment, the compound is a member selected from: 4-(3-{2-[1-(3,4-dimethylphenyl)-3-methyl-5-oxopyrazol-4-ylidene]hydrazin-1-yl}-2-hydroxyphenyl)-1$\lambda^6$-thiane-1,1-dione; 1-(3,4-dimethylphenyl)-4-(2-{2-hydroxy-3-[1-ethyl-piperidin-4-yl]phenyl}hydrazin-1-ylidene)-3-methyl-4,5-dihydro-1H-pyrazol-5-one; 4-(3-{2-[1-(3,4-dimethylphenyl)-3-methyl-5-oxopyrazol-4-ylidene]hydrazin-1-yl}-2-hydroxyphenyl)pyrrolidine-2-carboxylic acid; 3-(3'-{2-[1-(3-trifluoromethyl-phenyl)-3-methyl-5-oxo-4,5-dihydro-1H-pyrazol-4-ylidene]hydrazino}-2'-hydroxy-phenyl)cyclohexane-1-carboxylic acid; 3-(3'-{2-[1-(3,4-dichlorophenyl)-3-methyl-5-oxo-4,5-dihydro-1H-pyrazol-4-ylidene]hydrazino}-2'-hydroxy-phenyl)cyclohexane-1-carboxylic acid; 3-(3'-{2-[1-(4-tert-butylphenyl)-3-methyl-5-oxo-4,5-dihydro-1H-pyrazol-4-ylidene]hydrazino}-2'-hydroxy-phenyl)cyclohexane-1-carboxylic acid; 3-(3'-{2-[1-(4-fluoro-3-methylphenyl)-3-methyl-5-oxo-4,5-dihydro-1H-pyrazol-4-ylidene]hydrazino}-2'-hydroxy-phenyl)cyclohexane-1-carboxylic acid; and 3-{3'-[2-(1-cyclohexyl-3-methyl-5-oxo-4,5-dihydro-1H-pyrazol-4-ylidene)hydrazine]-2'-hydroxy-phenyl}cyclohexane-1-carboxylic acid.

In an additional embodiment, the compound is a member selected from: 3-(3'-{2-[1-(1-cyclopropylpiperidin-4-yl)-3-methyl-5-oxo-4,5-dihydro-1H-pyrazol-4-ylidene]hydrazino}-2'-hydroxy-phenyl)cyclohexane-1-carboxylic acid; 3-(3'-{2-[1-(1-methyl-1-oxo-1$\lambda^5$-phosphinan-4-yl)-3-methyl-5-oxo-4,5-dihydro-1H-pyrazol-4-ylidene]hydrazino}-2'-hydroxy-phenyl)cyclohexane-1-carboxylic acid; 3-(3'-{2-[1-(1-ethylazetidin-3-yl)-3-methyl-5-oxo-4,5-dihydro-1H-pyrazol-4-ylidene]hydrazino}-2'-hydroxy-phenyl)cyclohexane-1-carboxylic acid; 3-(3'-{2-[1-(pyridin-2-yl)-3-methyl-5-oxo-4,5-dihydro-1H-pyrazol-4-ylidene]hydrazino}-2'-hydroxy-phenyl)cyclohexane-1-carboxylic acid; 3-(3'-{2-[1-(pyridin-3-yl)-3-methyl-5-oxo-4,5-dihydro-1H-pyrazol-4-ylidene]hydrazino}-2'-hydroxy-phenyl)cyclohexane-1-carboxylic acid; 3-(3'-{2-[1-(pyridin-4-yl)-3-methyl-5-oxo-4,5-dihydro-1H-pyrazol-4-ylidene]hydrazino}-2'-hydroxy-phenyl)cyclohexane-1-carboxylic acid; 3-[2-hydroxy-3-(2-{3-methyl-5-oxo-1-[1-(2,2,2-trifluoroethyl)azetidin-3-yl]pyrazol-4-ylidene}hydrazin-1-yl)phenyl]cyclohexane-1-carboxylic acid; 3-(3'-{2-[1-(oxan-4-yl)-3-methyl-5-oxo-4,5-dihydro-1H-pyrazol-4-ylidene]hydrazino}-2'-hydroxy-phenyl)cyclohexane-1-carboxylic acid; 3-(3'-{2-[1-(1-ethylpiperidin-4-yl)-3-methyl-5-oxo-4,5-dihydro-1H-pyrazol-4-ylidene]hydrazino}-2'-hydroxy-phenyl)cyclohexane-1-carboxylic acid; and 3-[3'-(2-{1-[1-(2,2,2-trifluoroethyl)piperidin-4-yl]-3-methyl-5-oxo-4,5-dihydro-1H-pyrazol-4-ylidene}hydrazine)-2'-hydroxy-phenyl]cyclohexane-1-carboxylic acid.

In an additional embodiment, the compound is a member selected from: 3-(3'-{2-[1-(1-acetylpiperidin-4-yl)-3-methyl-5-oxo-4,5-dihydro-1H-pyrazol-4-ylidene]hydrazino}-2'-hydroxy-phenyl)cyclohexane-1-carboxylic acid; 3-(3'-{2-[1-(1-methanesulfonylpiperidin-4-yl)-3-methyl-5-oxo-4,5-dihydro-1H-pyrazol-4-ylidene]hydrazino}-2'-hydroxy-phenyl)cyclohexane-1-carboxylic acid; 3-[3'-(2-{1-[1-(2-methoxyacetyl)piperidin-4-yl]-3-methyl-5-oxo-4,5-dihydro-1H-pyrazol-4-ylidene}hydrazine)-2'-hydroxy-phenyl]cyclohexane-1-carboxylic acid; 3-(3'-{2-[1-(thiophen-2-yl)-3-methyl-5-oxo-4,5-dihydro-1H-pyrazol-4-ylidene]hydrazino}-2'-hydroxy-phenyl)cyclohexane-1-carboxylic acid; 3-(3'-{2-[1-(thiophen-3-yl)-3-methyl-5-oxo-4,5-dihydro-1H-pyrazol-4-ylidene]hydrazino}-2'-hydroxy-phenyl)cyclohexane-1-carboxylic acid; 3-(3'-{2-[1-(4-hydroxycyclohexyl)-3-methyl-5-oxo-4,5-dihydro-1H-pyrazol-4-ylidene]hydrazino}-2'-hydroxy-phenyl)cyclohexane-1-carboxylic acid; 3-(3'-{2-[1-(4-methoxycyclohexyl)-3-methyl-5-oxo-4,5-dihydro-1H-pyrazol-4-ylidene]hydrazino}-2'-hydroxy-phenyl)cyclohexane-1-carboxylic acid; 3-[3'-(2-{1-[1-(1-cyclopropylsulfonyl)piperidin-4-yl]-3-methyl-5-oxo-4,5-dihydro-1H-pyrazol-4-ylidene}hydrazine)-2'-hydroxy-phenyl]cyclohexane-1-carboxylic acid; 3-[3'-(2-{1-[1-(4-dimethylamino)cyclohexyl]-3-methyl-5-oxo-4,5-dihydro-1H-pyrazol-4-ylidene}hydrazine)-2'-hydroxy-phenyl]cyclohexane-1-carboxylic acid; and 3-(3-{2-[1-[3-(difluoromethoxy)phenyl]-3-methyl-5-oxo-4,5-dihydro-1H-pyrazol-4-ylidene]hydrazin-1-yl}-2-hydroxyphenyl)cyclohexane-1-carboxylic acid.

In an additional embodiment, the compound is a member selected from: 3-(2-hydroxy-3-{2-[3-methyl-5-oxo-1-(1-oxo-1-phenyl-1$\lambda^5$-phosphinan-4-yl)-4,5-dihydro-1H-pyrazol-4-ylidene]hydrazin-1-yl}phenyl)cyclohexane-1-carboxylic acid; 3-(3'-{2-[1-(4,4-difluorocyclohexyl)-3-methyl-5-oxo-4,5-dihydro-1H-pyrazol-4-ylidene]hydrazino}-2'-hydroxy-phenyl)cyclohexane-1-carboxylic acid; 3-(3'-{2-[1-(4-hydroxycyclohexyl)-3-methyl-5-oxo-4,5-dihydro-1H-pyrazol-4-ylidene]hydrazino}-2'-hydroxy-phenyl)cyclohexane-1-carboxylic acid; 3-{3'-[2-(1-cyclopentyl-3-methyl-5-oxo-4,5-dihydro-1H-pyrazol-4-ylidene)hydrazino]-2'-hydroxy-phenyl}cyclohexane-1-carboxylic acid; 3-{3'-[2-(1-cycloheptyl-3-methyl-5-oxo-4,5-dihydro-1H-pyrazol-4-ylidene)hydrazino]-2'-hydroxy-phenyl]cyclohexane-1-carboxylic acid; 4-(2-{2-hydroxy-3-[3-(1H-1,2,3,4-tetrazol-5-yl)cyclohexyl]phenyl}hydrazin-1-ylidene)-3-methyl-1-[3-(trifluoromethyl)phenyl]-4,5-dihydro-1H-pyrazol-5-one; 1-(3,4-dichlorophenyl)-4-(2-{2-hydroxy-3-[3-(1H-1,2,3,4-tetrazol-5-yl)cyclohexyl]phenyl}hydrazin-1-ylidene)-3-methyl-4,5-dihydro-1H-pyrazol-5-one; 1-(4-tert-butylphenyl)-4-(2-{2-hydroxy-3-[3-(1H-1,2,3,4-tetrazol-5-yl)cyclohexyl]phenyl}hydrazin-1-ylidene)-3-methyl-4,5-dihydro-1H-pyrazol-5-one; 1-(4-fluoro-3-methylphenyl)-4-(2-{2-hydroxy-3-[3-(1H-1,2,3,4-tetrazol-5-yl)cyclohexyl]phenyl}hydrazin-1-ylidene)-3-methyl-4,5-dihydro-1H-pyrazol-5-one; 1-cyclohexyl-4-(2-{2-hydroxy-3-[3-(1H-1,2, 3,4-tetrazol-5-yl)cyclohexyl]phenyl}hydrazin-1-ylidene)-3-methyl-4,5-dihydro-1H-pyrazol-5-one; and 1-(1-cyclo)-4-(2-{2-hydroxy-3-[3-(1H-1,2,3,4-tetrazol-5-yl)cyclohexyl]phenyl}hydrazin-1-ylidene)-3-methyl-4,5-dihydro-1H-pyrazol-5-one.

In an additional embodiment, the compound is a member selected from: 1-(1-cyclopropylpiperidin-4-yl)-4-(2-{2-hydroxy-3-[3-(1H-1,2,3,4-tetrazol-5-yl)cyclohexyl]phenyl}hydrazin-1-ylidene)-3-methyl-4,5-dihydro-1H-pyrazol-5-one; 1-(1-ethylazetidin-3-yl)-4-(2-{2-hydroxy-3-[3-(1H-1,2,3,4-tetrazol-5-yl)cyclohexyl]phenyl}hydrazin-1-ylidene)-3-methyl-4,5-dihydro-1H-pyrazol-5-one; 4-(2-{2-hydroxy-3-[3-(1H-1,2,3,4-tetrazol-5-yl)cyclohexyl]phenyl}hydrazin-1-ylidene)-3-methyl-1-(1-methyl-1-oxo-1$\lambda^5$-phosphinan-4-yl)-4,5-dihydro-1H-pyrazol-5-one; 2-[4-(2-hydroxy-3-{2-[3-methyl-5-oxo-1-[3-trifluoromethyl)phenyl]-4,5-dihydro-1H-pyrazol-4-ylidene]hydrazin-1-yl}phenyl)piperidin-1-yl]acetic acid; 2-[4-(3-{2-[1-(3,4-dichlorophenyl)-3-methyl-5-oxo-4,5-dihydro-1H-pyrazol-4-ylidene]hydrazin-1-yl}-2-hydroxyphenyl)piperidin-1-yl]acetic acid; 2-[4-(3-{2-[1-(4-tert-butylphenyl)-3-methyl-5-oxo-4,5-dihydro-1H-pyrazol-4-ylidene]hydrazin-1-yl}-2-hydroxyphenyl)piperidin-1-yl]acetic acid; 2-[4-(3-{2-[1-(4-fluoro-3-methylphenyl)-3-methyl-5-oxo-4,5-dihydro-1H-pyrazol-4-ylidene]hydrazin-1-yl}-2-hydroxyphenyl)piperidin-1-yl]acetic acid; and 2-[4-(3-{2-[1-cyclohexyl-3-methyl-5-oxo-4,5-dihydro-1H-pyrazol-4-ylidene]hydrazin-1-yl}-2-hydroxyphenyl)piperidin-1-yl]acetic acid.

In an additional embodiment, the compound is a member selected from: 2-[4-(3-{2-[1-(1-cyclopropylpiperidin-4-yl)-3-methyl-5-oxo-4,5-dihydro-1H-pyrazol-4-ylidene]hydrazin-1-yl}-2-hydroxyphenyl)piperidin-1-yl]acetic acid; 2-[4-(3-{2-[1-(1-ethylazetidin-3-yl)-3-methyl-5-oxo-4,5-dihydro-1H-pyrazol-4-ylidene]hydrazin-1-yl}-2-hydroxyphenyl)piperidin-1-yl]acetic acid; 2-[4-(2-hydroxy-3-{2-[3-methyl-1-(1-methyl-1-oxo-1$\lambda^5$-phosphinan-4-yl)-5-oxo-4,5-dihydro-1H-pyrazol-4-ylidene]hydrazin-1-yl}phenyl)piperidin-1-yl]acetic acid; 3-(3-{2-[5-[(dimethylamino)methyl]-4-methyl-2,6-dioxo-1-[3-(trifluoromethyl)phenyl]-1,2,3,6-tetrahydropyridin-3-ylidene]hydrazin-1-yl}-2-hydroxyphenyl)cyclohexane-1-carboxylic acid; 3-[3-(2-{5-[(dimethylamino)methyl]-4-methyl-2,6-dioxo-1-(3,4-dichlorophenyl)-1,2,3,6-tetrahydropyridin-3-ylidene}hydrazin-1-yl)-2-hydroxyphenyl]cyclohexane-1-carboxylic acid; and 3-[3-(2-{5-[(dimethylamino)methyl]-4-methyl-2,6-dioxo-1-(4-tert-butylphenyl)-1,2,3,6-tetrahydropyridin-3-ylidene}hydrazin-1-yl)-2-hydroxyphenyl]cyclohexane-1-carboxylic acid.

In an additional embodiment, the compound is a member selected from: 3-[3-(2-{5-[(dimethylamino)methyl]-4-methyl-2,6-dioxo-1-(4-fluoro-3-methylphenyl)-1,2,3,6-tetrahydropyridin-3-ylidene}hydrazin-1-yl)-2-hydroxyphenyl]cyclohexane-1-carboxylic acid; 3-[3-(2-{5-[(dimethylamino)methyl]-4-methyl-2,6-dioxo-1-cyclohexyl-1,2,3,6-tetrahydropyridin-3-ylidene}hydrazin-1-yl)-2-hydroxyphenyl]cyclohexane-1-carboxylic acid; 3-[3-(2-{5-[(dimethylamino)methyl]-4-methyl-2,6-dioxo-1-(1-cyclopropylpiperidin-4-yl)-1,2,3,6-tetrahydropyridin-3-ylidene}hydrazin-1-yl)-2-hydroxyphenyl]cyclohexane-1-carboxylic acid; 3-[3-(2-{5-[(dimethylamino)methyl]-4-methyl-1-(1-methyl-1-oxo-1$\lambda^5$-phosphinan-4-yl)-2,6-dioxo-1,2,3,6-tetrahydropyridin-3-ylidene}hydrazin-1-yl)-2-hydroxyphenyl]cyclohexane-1-carboxylic acid; 5-[(dimethylamino)methyl]-3-(2-{2-hydroxy-3-[3-(1H-1,2,3,4-tetrazol-5-yl)cyclohexyl]phenyl}hydrazin-1-ylidene)-4-methyl-1-[3-(trifluoromethyl)phenyl]-1,2,3,6-tetrahydropyridine-2,6-dione; 1-(3,4-dichlorophenyl)-5-[(dimethylamino)methyl]-3-(2-{2-hydroxy-3-[3-(1H-1,2,3,4-tetrazol-5-yl)cyclohexyl]phenyl}hydrazin-1-ylidene)-4-methyl-1,2,3,6-tetrahydropyridine-2,6-dione; 1-(4-tert-butylphenyl)-5-[(dimethylamino)methyl]-3-(2-{2-hydroxy-3-[3-(1H-1,2,3,4-tetrazol-5-yl)cyclohexyl]phenyl}hydrazin-1-ylidene)-4-methyl-1,2,3,6-tetrahydropyridine-2,6-dione; 1-(4-fluoro-3-methylphenyl)-5-[(dimethylamino)methyl]-3-(2-{2-hydroxy-3-[3-(1H-1,2,3,4-tetrazol-5-yl)cyclohexyl]phenyl}hydrazin-1-ylidene)-4-methyl-1,2,3,6-tetrahydropyridine-2,6-dione; 1-cyclohexyl-5-[(dimethylamino)methyl]-3-(2-{2-hydroxy-3-[3-(1H-1,2,3,4-tetrazol-5-yl)cyclohexyl]phenyl}hydrazin-1-ylidene)-4-methyl-1,2,3,6-tetrahydropyridine-2,6-dione; 1-(1-cyclopropylpiperidin-4-yl)-5-[(dimethylamino)methyl]-3-(2-{2-hydroxy-3-[3-(1H-1,2,3,4-tetrazol-5-yl)cyclohexyl]phenyl}hydrazin-1-ylidene)-4-methyl-1,2,3,6-tetrahydropyridine-2,6-dione; and 5-[(dimethylamino)methyl]-3-(2-{2-hydroxy-3-[3-(1H-1,2,3,4-tetrazol-5-yl)cyclohexyl]phenyl}hydrazin-1-ylidene)-4-methyl-1-(1-methyl-1-oxo-1$\lambda^5$-phosphinan-4-yl)-1,2,3,6-tetrahydropyridine-2,6-dione.

In an additional embodiment, the compound is a member selected from: 2-[4-(3-{2-[1-(3,4-dichlorophenyl)-5-[(dimethylamino)methyl]-4-methyl-2,6-dioxo-1,2,3,6-tetrahydropyridin-3-ylidene]hydrazin-1-yl}-2-hydroxyphenyl)piperidin-1-yl]acetic acid; 2-[4-(3-{2-[1-(4-tert-butylphenyl)-5-[(dimethylamino)methyl]-4-methyl-2,6-dioxo-1,2,3,6-tetrahydropyridin-3-ylidene]hydrazin-1-yl}-2-hydroxyphenyl)piperidin-1-yl]acetic acid; 2-[4-(3-{2-[1-(4-fluoro-3-methylphenyl)-5-[(dimethylamino)methyl]-4-methyl-2,6-dioxo-1,2,3,6-tetrahydropyridin-3-ylidene]hydrazin-1-yl}-2-hydroxyphenyl)piperidin-1-yl]acetic acid; 2-{4-[3-(2-{5-[(dimethylamino)methyl]-4-methyl-2,6-dioxo-1-[3-(trifluoromethyl)phenyl]-1,2,3,6-tetrahydropyridin-3-ylidene}hydrazin-1-yl)-2-hydroxyphenyl]piperidin-1-yl}acetic acid; 2-[4-(3-{2-[1-cyclohexyl-5-[(dimethylamino)methyl]-4-methyl-2,6-dioxo-1,2,3,6-tetrahydropyridin-3-ylidene]hydrazin-1-yl}-2-hydroxyphenyl)piperidin-1-yl]acetic acid; 2-[4-(3-{2-[1-(1-cyclopropylpiperidin-4-yl)-5-[(dimethylamino)methyl]-4-methyl-2,6-dioxo-1,2,3,6-tetrahydropyridin-3-ylidene]hydrazin-1-yl}-2-hydroxyphenyl)piperidin-1-yl]acetic acid; and 2-{4-[3-(2-{5-[(dimethylamino)methyl]-4-methyl-1-(1-methyl-1-oxo-1$\lambda^5$-phosphinan-4-yl)-2,6-dioxo-1,2,3,6-tetrahydropyridin-3-ylidene}hydrazin-1-yl)-2-hydroxyphenyl]piperidin-1-yl}acetic acid.

In an additional embodiment, the compound is a member selected from: 3-[3-(2-{5-[(diethylamino)methyl]-1-(3,4-dimethylphenyl)-4-methyl-2,6-dioxo-1,2,3,6-tetrahydropyridin-3-ylidene}hydrazin-1-yl)-2-hydroxyphenyl]cyclohexane-1-carboxylic acid; 3-(3-{2-[5-{[cyclopropyl(ethyl)amino]methyl}-1-(3,4-dimethylphenyl)-4-methyl-2,6-dioxo-1,2,3,6-tetrahydropyridin-3-ylidene]hydrazin-1-yl}-2-hydroxyphenyl)cyclohexane-1-carboxylic acid; 3-(3-{2-[1-(3,4-dimethylphenyl)-4-methyl-2,6-dioxo-5-{[(2,2,2-trifluoroethyl)amino]methyl}-1,2,3,6-tetrahydropyridin-3-ylidene]hydrazin-1-yl}-2-hydroxyphenyl)cyclohexane-1-carboxylic acid; 3-(3-{2-[1-(3,4-dimethylphenyl)-4-methyl-2,6-dioxo-5-(pyrrolidin-1-ylmethyl)-1,2,3,6-tetrahydropyridin-3-ylidene]hydrazin-1-yl}-2-hydroxyphenyl)cyclohexane-1-carboxylic acid; 3-(3-{2-[1-(3,4-dimethylphenyl)-4-methyl-2,6-dioxo-1,2,3,6-tetrahydropyridin-3-ylidene]hydrazin-1-yl}-2-hydroxyphenyl)cyclohexane-1-carboxylic acid; 3-(3-{2-[5-cyano-1-(3,4-dimethylphenyl)-4-methyl-2,6-dioxo-1,2,3,6-tetrahydropyridin-3-ylidene]hydrazin-1-yl}-2-hydroxyphenyl)cyclohexane-1-carboxylic acid; 5-[(diethylamino)methyl]-1-(3,4-dimethylphenyl)-3-(2-{2- hydroxy-3-[3-(1H-1,2,3,4-tetrazol-5-yl)cyclohexyl]phenyl}hydrazin-1-ylidene)-4-methyl-1,2,3,6-tetrahydropyridine-2,6-dione; and 5-{[cyclopropyl(ethyl)amino]methyl}-1-(3,4-dimethylphenyl)-3-(2-{2-hydroxy-3-[3-(1H-1,2,3,4-tetrazol-5-yl)cyclohexyl]phenyl}hydrazin-1-ylidene)-4-methyl-1,2,3,6-tetrahydropyridine-2,6-dione.

In an additional embodiment, the compound is a member selected from: 1-(3,4-dimethylphenyl)-3-(2-{2-hydroxy-3-[3-(1H-1,2,3,4-tetrazol-5-yl)cyclohexyl]phenyl}hydrazin-1-ylidene)-4-methyl-5-{[(2,2,2-trifluoroethyl)amino]methyl}-1,2,3,6-tetrahydropyridine-2,6-dione; 1-(3,4-dimethylphenyl)-3-(2-{2-hydroxy-3-[3-(1H-1,2,3,4-tetrazol-5-yl)cyclohexyl]phenyl}hydrazin-1-ylidene)-4-methyl-5-(pyrrolidin-1-ylmethyl)-1,2,3,6-tetrahydropyridine-2,6-dione; 1-(3,4-dimethylphenyl)-5-(2-{2-hydroxy-3-[3-(1H-1,2,3,4-tetrazol-5-yl)cyclohexyl]phenyl}hydrazin-1-ylidene)-4-methyl-2,6-dioxo-1,2,5,6-tetrahydropyridine-3-carbonitrile; 1-(3,4-dimethylphenyl)-3-(2-{2-hydroxy-3-[3-(1H-1,2,3,4-tetrazol-5-yl)cyclohexyl]phenyl}hydrazin-1-ylidene)-4-methyl-1,2,3,6-tetrahydropyridine-2,6-dione; 2-{4-[3-(2-{5-[(diethylamino)methyl]-1-(3,4-dimethylphenyl)-4-methyl-2,6-dioxo-1,2,3,6-tetrahydropyridin-3-ylidene}hydrazin-1-yl)-2-hydroxyphenyl]piperidin-1-yl}acetic acid; 2-[4-(3-{2-[5-{[cyclopropyl(ethyl)amino]methyl}-1-(3,4-dimethylphenyl)-4-methyl-2,6-dioxo-1,2,3,6-tetrahydropyridin-3-ylidene]hydrazin-1-yl}-2-hydroxyphenyl)piperidin-1-yl]acetic acid; 2-[4-(3-{2-[1-(3,4-dimethylphenyl)-4-methyl-2,6-dioxo-5-{[(2,2,2-trifluoroethyl)amino]methyl}-1,2,3,6-tetrahydropyridin-3-ylidene]hydrazin-1-yl}-2-hydroxyphenyl)piperidin-1-yl]acetic acid; 2-[4-(3-{2-[(3Z)-1-(3,4-dimethylphenyl)-4-methyl-2,6-dioxo-5-(pyrrolidin-1-ylmethyl)-1,2,3,6-tetrahydropyridin-3-ylidene]hydrazin-1-yl}-2-hydroxyphenyl)piperidin-1-yl]acetic acid; 2-[4-(3-{2-[5-cyano-1-(3,4-dimethylphenyl)-4-methyl-2,6-dioxo-1,2,3,6-tetrahydropyridin-3-ylidene]hydrazin-1-yl}-2-hydroxyphenyl)piperidin-1-yl]acetic acid; and 2-[4-(3-{2-[1-(3,4-dimethylphenyl)-4-methyl-2,6-dioxo-1,2,3,6-tetrahydropyridin-3-ylidene]hydrazin-1-yl}-2-hydroxyphenyl)piperidin-1-yl]acetic acid.

In an additional embodiment, the compound is a member selected from: 2-[4-(3-{2-[5-(chloromethyl)-1-(3,4-dimethylphenyl)-4-methyl-2,6-dioxo-1,2,3,6-tetrahydropyridin-3-ylidene]hydrazin-1-yl}-2-hydroxyphenyl)piperidin-1-yl]acetic acid; 3-(3-{2-[1-(3,4-dimethylphenyl)-2-(2-methoxyethyl)-5-oxo-4,5-dihydro-1H-imidazol-4-ylidene]hydrazin-1-yl}-2-hydroxyphenyl)cyclohexane-1-carboxylic acid; 3-(3-{2-[1-(3,4-dimethylphenyl)-2-ethyl-5-oxo-4,5-dihydro-1H-imidazol-4-ylidene]hydrazin-1-yl}-2-hydroxyphenyl)cyclohexane-1-carboxylic acid; 3-(3-{2-[1-(3,4-dimethylphenyl)-2-(dimethylaminomethyl)-5-oxo-4,5-dihydro-1H-imidazol-4-ylidene]hydrazin-1-yl}-2-hydroxyphenyl)cyclohexane-1-carboxylic acid; 3-(3-{2-[1-(3,4-dimethylphenyl)-2-(1-ethylazetidin-3-yl)-5-oxo-4,5-dihydro-1H-imidazol-4-ylidene]hydrazin-1-yl}-2-hydroxyphenyl)cyclohexane-1-carboxylic acid; 3-(3-{2-[1-(3,4-dimethylphenyl)-5-oxo-4,5-dihydro-1H-imidazol-4-ylidene]hydrazin-1-yl}-2-hydroxyphenyl)cyclohexane-1-carboxylic acid; 1-(3,4-dimethylphenyl)-4-(2-{2-hydroxy-3-[3-(1H-1,2,3,4-tetrazol-5-yl)cyclohexyl]phenyl}hydrazin-1-ylidene)-2-(2-methoxyethyl)-4,5-dihydro-1H-imidazol-5-one; 1-(3,4-dimethylphenyl)-4-(2-{2-hydroxy-3-[3-(1H-1,2,3,4-tetrazol-5-yl)cyclohexyl]phenyl}hydrazin-1-ylidene)-2-ethyl-4,5-dihydro-1H-imidazol-5-one; and 1-(3,4-dimethylphenyl)-4-(2-{2-hydroxy-3-[3-(1H-1,2,3,4-tetrazol-5-yl)cyclohexyl]phenyl}hydrazin-1-ylidene)-2-dimethylaminomethyl)-4,5-dihydro-1H-imidazol-5-one.

In an additional embodiment, the compound is a member selected from: 1-(3,4-dimethylphenyl)-4-(2-{2-hydroxy-3-[3-(1H-1,2,3,4-tetrazol-5-yl)cyclohexyl]phenyl}hydrazin-1-ylidene)-2-(1-ethylazetidin-3-yl)-4,5-dihydro-1H-imidazol-5-one; 1-(3,4-dimethylphenyl)-4-(2-{2-hydroxy-3-[3-(1H-1,2,3,4-tetrazol-5-yl)cyclohexyl]phenyl}hydrazin-1-ylidene)-4,5-dihydro-1H-imidazol-5-one; 2-[4-(3-{2-[1-(3,4-dimethylphenyl)-2-(2-methoxyethyl)-5-oxo-4,5-dihydro-1H-imidazol-4-ylidene]hydrazin-1-yl]-2-hydroxyphenyl)piperidin-1-yl]acetic acid; 2-[4-(3-{2-[1-(3,4-dimethylphenyl)-2-ethyl-5-oxo-4,5-dihydro-1H-imidazol-4-ylidene]hydrazin-1-yl}-2-hydroxyphenyl)piperidin-1-yl]acetic acid; 2-[4-(3-{2-[1-(3,4-dimethylphenyl)-2-(dimethylaminomethyl)-5-oxo-4,5-dihydro-1H-imidazol-4-ylidene]hydrazin-1-yl}-2-hydroxyphenyl)piperidin-1-yl]acetic acid; 2-[4-(3-{2-[1-(3,4-dimethylphenyl)-2-(1-ethylazetidin-3-yl)-5-oxo-4,5-dihydro-1H-imidazol-4-ylidene]hydrazin-1-yl}-2-hydroxyphenyl)piperidin-1-yl]acetic acid; 2-[4-(3-{2-[1-(3,4-dimethylphenyl)-5-oxo-4,5-dihydro-1H-imidazol-4-ylidene]hydrazin-1-yl}-2-hydroxyphenyl)piperidin-1-yl]acetic acid; and 2-[4-(3-{2-[1-(3,4-dimethylphenyl)-2-(2,2,2-trifluoroethyl)-5-oxo-4,5-dihydro-1H-imidazol-4-ylidene]hydrazin-1-yl}-2-hydroxyphenyl)piperidin-1-yl]acetic acid.

In an additional embodiment, the compound is a member selected from: 3-(3-{2-[5-(3,4-dimethylphenyl)-1-methyl-2,4-dioxopyrrolidin-3-ylidene]hydrazin-1-yl}-2-hydroxyphenyl)cyclohexane-1-carboxylic acid; 3-(3-{2-[5-(3,4-dimethylphenyl)-2,4-dioxopyrrolidin-3-ylidene]hydrazin-1-yl}-2-hydroxyphenyl)cyclohexane-1-carboxylic acid; 3-(3-{2-[5-(3,4-dimethylphenyl)-1-(2-methoxyethyl)-2,4-dioxopyrrolidin-3-ylidene]hydrazin-1-yl}-2-hydroxyphenyl)cyclohexane-1-carboxylic acid; 3-(3-{2-[1-[2-(dimethylamino)ethyl]-5-(3,4-dimethylphenyl)-2,4-dioxopyrrolidin-3-ylidene]hydrazin-1-yl}-2-hydroxyphenyl)cyclohexane-1-carboxylic acid; 5-(3,4-dimethylphenyl)-3-(2-{2-hydroxy-3-[3-(1H-1,2,3,4-tetrazol-5-yl)cyclohexyl]phenyl}hydrazin-1-ylidene)-1-methylpyrrolidine-2,4-dione; 5-(3,4-dimethylphenyl)-3-(2-{2-hydroxy-[3-[3-(1H-1,2,3,4-tetrazol-5-yl)cyclohexyl]phenyl}hydrazin-1-ylidene)-pyrrolidine-2,4-dione; 1-[2-(dimethylamino)ethyl]-5-(3,4-dimethylphenyl)-3-(2-{2-hydroxy-3-[3-(1H-1,2,3,4-tetrazol-5-yl)cyclohexyl]phenyl}hydrazin-1-ylidene)pyrrolidine-2,4-dione; 5-(3,4-dimethylphenyl)-3-(2-{2-hydroxy-3-[3-(1H-1,2,3,4-tetrazol-5-yl)cyclohexyl]phenyl}hydrazin-1-ylidene)-1-(2-methoxyethyl)pyrrolidine-2,4-dione; 2-[4-(3-{2-[1-[2-(dimethylamino)ethyl]-5-(3,4-dimethylphenyl)-2,4-dioxopyrrolidin-3-ylidene]hydrazin-1-yl}-2-hydroxyphenyl)piperidin-1-yl]acetic acid.

In an additional embodiment, the compound is a member selected from: 2-[4-(3-{2-[5-(3,4-dimethylphenyl)-1-(2-methoxyethyl)-2,4-dioxopyrrolidin-3-ylidene]hydrazin-1-yl}-2-hydroxyphenyl)piperidin-1-yl]acetic acid; 2-[4-(3-{2-[5-(3,4-dimethylphenyl)-1-methyl-2,4-dioxopyrrolidin-3-ylidene]hydrazin-1-yl}-2-hydroxyphenyl)piperidin-1-yl]acetic acid; 2-[4-(3-{2-[5-(3,4-dimethylphenyl)-2,4-dioxopyrrolidin-3-ylidene]hydrazin-1-yl}-2-hydroxyphenyl)piperidin-1-yl]acetic acid; 3-[3-({1-[1-(3,4-dimethylphenyl)-5-hydroxy-3-methyl-1H-pyrazol-4-yl]-2,2,2-trifluoroethyl}amino)-2-hydroxyphenyl]cyclohexane-1-carboxylic acid; 3-[3-({1-[1-(3,4-dimethylphenyl)-5-hydroxy-3-methyl-1H-pyrazol-4-yl]-2,2-difluoropropyl}amino)-2-hydroxyphenyl]cyclohexane-1-carboxylic acid; 3-[3-({1-[1-(3,4-dimethylphenyl)-5- hydroxy-3-methyl-1H-pyrazol-4-yl]-2,2,3,3,3-pentafluoropropyl}amino)-2-hydroxyphenyl]cyclohexane-1-carboxylic acid; 3-[3-({1-[1-(3,4-dimethylphenyl)-5-hydroxy-3-methyl-1H-pyrazol-4-yl]-2,2,2-trifluoroethyl}amino)-2-hydroxyphenyl]cyclohexane-1-carboxylic acid ethyl ester; 3-[3-({1-[1-(3,4-dimethylphenyl)-5-hydroxy-3-methyl-1H-pyrazol-4-yl]-2,2-difluoropropyl}amino)-2-hydroxyphenyl]cyclohexane-1-carboxylic acid ethyl ester.

In an additional embodiment, the compound is a member selected from: 3-[3-({1-[1-(3,4-dimethylphenyl)-5-hydroxy-3-methyl-1H-pyrazol-4-yl]-2,2,3,3,3-pentafluoropropyl}amino)-2-hydroxyphenyl]cyclohexane-1-carboxylic acid ethyl ester; 1-(3,4-dimethylphenyl)-3-methyl-4-(2,2,2-trifluoro-1-({2-hydroxy-3-[3-(1H-1,2,3,4-tetrazol-5-yl)cyclohexyl]phenyl}amino)ethyl]-1H-pyrazol-5-ol; 4-[2,2-difluoro-1-({2-hydroxy-3-[3-(1H-1,2,3,4-tetrazol-5-yl)cyclohexyl]phenyl}amino)propyl]-1-(3,4-dimethylphenyl)-3-methyl-1H-pyrazol-5-ol; 1-(3,4-dimethylphenyl)-3-methyl-4-[2,2,3,3,3-pentafluoro-1-({2-hydroxy-3-[3-(1H-1,2,3,4-tetrazol-5-yl)cyclohexyl]phenyl}amino)propyl]-1H-pyrazol-5-ol; 1-(3,4-dimethylphenyl)-3-methyl-4-[(2,2,3,3,3-pentafluoro-1-{2-hydroxy-3-[3-(1H-1,2,3,4-tetrazol-5-yl)cyclohexyl]phenyl}propyl)amino]-1H-pyrazol-5-ol; 4-[(2,2-difluoro-1-{2-hydroxy-3-[3-(1H-1,2,3,4-tetrazol-5-yl)cyclohexyl]phenyl}propyl)amino]-1-(3,4-dimethylphenyl)-3-methyl-1H-pyrazol-5-ol; 1-(3,4-dimethylphenyl)-3-methyl-4-[(2,2,2-trifluoro-1-{2-hydroxy-3-[3-(1H-1,2,3,4-tetrazol-5-yl)cyclohexyl]phenyl}ethyl)amino]-1H-pyrazol-5-ol.

In an additional embodiment, the compound is a member selected from: 3-[3-(1-{[1-(3,4-dimethylphenyl)-5-hydroxy-3-methyl-1H-pyrazol-4-yl]amino}-2,2,2-trifluoroethyl)-2-hydroxyphenyl]cyclohexane-1-carboxylic acid; 3-[3-(1-{[1-(3,4-dimethylphenyl)-5-hydroxy-3-methyl-1H-pyrazol-4-yl]amino}-2,2-difluoropropyl)-2-hydroxyphenyl]cyclohexane-1-carboxylic acid; 3-[3-(1-{[1-(3,4-dimethylphenyl)-5-hydroxy-3-methyl-1H-pyrazol-4-yl]amino}-2,2,3,3,3-pentafluoropropyl)-2-hydroxyphenyl]cyclohexane-1-carboxylic acid; 3-[3-(1-{[1-(3,4-dimethylphenyl)-5-hydroxy-3-methyl-1H-pyrazol-4-yl]amino}-2,2,2-trifluoroethyl)-2-hydroxyphenyl]cyclohexane-1-carboxylic acid ethyl ester; 3-[3-(1-{[1-(3,4-dimethylphenyl)-5-hydroxy-3-methyl-1H-pyrazol-4-yl]amino}-2,2-difluoropropyl)-2-hydroxyphenyl]cyclohexane-1-carboxylic acid ethyl ester; 3-[3-(1-{[1-(3,4-dimethylphenyl)-5-hydroxy-3-methyl-1H-pyrazol-4-yl]amino}-2,2,3,3,3-pentafluoropropyl)-2-hydroxyphenyl]cyclohexane-1-carboxylic acid ethyl ester.

In another embodiment, the compound is a member selected from: 3-(3'-{2-[1-(3,4-dimethylphenyl)-3-methyl-5-oxo-4,5-dihydro-1H-pyrazol-4-ylidene]hydrazino}-2'-hydroxy-phenyl)cyclohexane-1-carboxylic acid; 3-(3'-{2-[1-(3,4-dimethylphenyl)-3-methyl-5-oxo-4,5-dihydro-1H-pyrazol-4-ylidene]hydrazino}-2'-hydroxy-phenyl)-1-(1H-tetrazol-5-yl)cyclohexane; 4-3'-{2-[1-(3,4-dimethylphenyl)-3-methyl-5-oxo-4,5-dihydro-1H-pyrazol-4-ylidene]hydrazino}-2'-hydroxy-phenyl)piperidin-1-yl-acetic acid; 1-methyl-1-oxo-4-(3'-{2-[1-(3,4-dimethylphenyl)-3-methyl-5-oxo-4,5-dihydro-1H-pyrazol-4-ylidene]hydrazino}-2'-hydroxy-phenyl)-1$\lambda^5$-phosphinane; 3-(3'-{2-[1-(1-methyl-1-oxo-1$\lambda^5$-phosphinan-4-yl)-3-methyl-5-oxo-4,5-dihydro-1H-pyrazol-4-ylidene]hydrazino}-2'-hydroxy-phenyl)cyclohexane-1-carboxylic acid; 3-(3'-{2-[1-(1-cyclopropylpiperidin-4-yl)-3-methyl-5-oxo-4,5-dihydro-1H-pyrazol-4-ylidene]hydrazino}-2'-hydroxy-phenyl)-1-(1H-tetrazol-5-yl)cyclohexane; 3-(3'-{2-[1-(3,4-dichlorophenyl)-3-(N,N-dimethylaminomethyl)-4-methyl-2,6-(1H,5H)-pyridinedion-4-ylidene]hydrazino}-2'-hydroxy-phenyl)cyclohexane-1-carboxylic acid; 3-(3'-{2-[1-(3,4-dimethylphenyl)-2-(N,N-dimethylaminomethyl)-5-oxo-4,5-dihydro-1H-imidazol-4-ylidene]hydrazino}-2'-hydroxy-phenyl)cyclohexane-1-carboxylic acid; 3-(3'-{2-[5-(3,4-dimethylphenyl)-1-methyl-2,4-pyrrolidinedion-4-ylidene]hydrazino}-2'-hydroxy-phenyl)cyclohexane-1-carboxylic acid; and 3-(3'-N-{1-[1-(3,4-dimethylphenyl)-3-methyl-5-oxo-4,5-dihydro-1H-pyrazol-4-yl]-2,2,2-trifluoroethylamino}-2'-hydroxy-phenyl)cyclohexane-1-carboxylic acid.

In an additional embodiment, the compound is 3-(3'-{2-[1-(3,4-dimethylphenyl)-3-methyl-5-oxo-4,5-dihydro-1H-pyrazol-4-ylidene]hydrazino}-2'-hydroxy-phenyl)cyclohexane-1-carboxylic acid.

In still an additional embodiment, the present invention is directed to a method of treating a disease (or disorder or condition) in an animal in need of such treatment, wherein the physiological disorder, symptom, or disease is thrombocytopenia resulting from causative factors selected from the group consisting of immune thrombocytopenic purpura, cancer chemotherapy, treatment with other drugs causing thrombocytopenia, surgery, liver transplantation, bone marrow or stem cell transplantation, radiation treatment or injury, severe bacterial infection, chronic viral infection, systemic lupus erythematosus, rheumatoid arthritis, hepatitis C viral infection, human immunodeficiency virus infection, myelodysplastic syndrome, and blood loss or withdrawal. Preferably, the disease is thrombocytopenia resulting from immune thrombocytopenic purpura.

In still an additional embodiment, the present invention is directed to a method of treating a disease (or disorder or condition) in an animal in need of such treatment, wherein the physiological disorder, symptom, or disease is thrombocytopenia resulting from causative factors selected from the group consisting of immune thrombocytopenic purpura, cancer chemotherapy, treatment with other drugs causing thrombocytopenia, surgery, liver transplantation, bone marrow or stem cell transplantation, radiation treatment or injury, severe bacterial infection, chronic viral infection, systemic lupus erythematosus, rheumatoid arthritis, hepatitis C viral infection, human immunodeficiency virus infection, myelodysplastic syndrome, and blood loss or withdrawal, which method comprises administering to said animal a therapeutically effective amount of a compound and/or pharmaceutical composition described herein, in combination with one or more compound(s) independently selected from the group consisting of other TPO mimetics, corticosteroids, intravenous immunoglobulin, hematopoietic growth factors, cell-cycle initiators, and chemotherapeutic agents. In an exemplary embodiment, the compound has a structure according to a formula described herein. In an exemplary embodiment, the compound is according to Formula (I), a pharmaceutically acceptable salt, solvate, and/or ester thereof, and a pharmaceutically acceptable excipient. Preferably, the corticosteroid is prednisone, and the hematopoietic growth factor is IL-11.

In still an additional embodiment, the present invention is directed to a method of treating thrombocytopenia by administering a pharmaceutical composition comprising a therapeutically effective amount of a compound and/or pharmaceutical composition described herein in combination with other treatments such as radiation. In an exemplary embodiment, the compound has a structure according to a formula described herein. In an exemplary embodiment, the compound is according to Formula (I), a pharmaceutically acceptable salt, solvate, and/or ester thereof, and a pharmaceutically acceptable excipient.

In still an additional embodiment, the present invention is directed to a method of treating thrombocytopenia by administering a pharmaceutical composition comprising a pharmaceutically acceptable excipient and a therapeutically effective amount of a compound described herein or a pharmaceutically acceptable salt, solvate and/or ester thereof, in combination with procedures such as splenectomy or platelet transfusion. In an exemplary embodiment, the compound has a structure according to a formula described herein. In an exemplary embodiment, the compound is according to Formula (I), a pharmaceutically acceptable salt, solvate, and/or ester thereof, and a pharmaceutically acceptable excipient.

In still an additional embodiment, the present invention is directed to a method of treating thrombocytopenia resulting from cancer chemotherapy, which method comprises administering to said animal a pharmaceutical composition comprising a pharmaceutically acceptable excipient and a therapeutically effective amount of a compound described herein, a pharmaceutically acceptable salt, solvate and/or ester thereof, in combination with one or more compound(s) independently selected from the group consisting of: tubulin modulators, cytotoxic agents, antineoplastic agents, immunosuppressive agents, estrogen receptor modulators, and the like. In an exemplary embodiment, the compound has a structure according to a formula described herein. In an exemplary embodiment, the compound is according to Formula (I), a pharmaceutically acceptable salt, solvate, and/or ester thereof, and a pharmaceutically acceptable excipient.

In still an additional embodiment, the present invention is directed to a method of treating thrombocytopenia resulting from hepatitis C viral infection, which method comprises administering to said animal a pharmaceutical composition comprising a therapeutically effective amount of a compound described herein, a pharmaceutically acceptable salt, solvate and/or ester thereof, and a pharmaceutically acceptable excipient in combination with one or more compound(s) independently selected from the group consisting of: hepatitis C viral protease inhibitors, nucleoside analogue with antiviral activity (e.g., ribavirin) and cytokines (e.g., interferon-alpha). In an exemplary embodiment, the compound has a structure according to a formula described herein. In an exemplary embodiment, the compound is according to Formula (I), a pharmaceutically acceptable salt, solvate, and/or ester thereof, and a pharmaceutically acceptable excipient.

In still an additional embodiment, the present invention is directed to a method of treating thrombocytopenia resulting from human immunodeficiency viral infection, which method comprises administering to said animal a pharmaceutical composition comprising a therapeutically effective amount of a compound described herein, a pharmaceutically acceptable salt, solvate and/or ester thereof, and a pharmaceutically acceptable excipient in combination with one or more compound(s) independently selected from the group consisting of: viral protease inhibitors, highly active antiretroviral therapy, nucleoside reverse transcriptase inhibitors, nonnucleoside reverse transcriptase inhibitors, cytokines (e.g., interferon-alpha), and the like. In an exemplary embodiment, the compound has a structure according to a formula described herein. In an exemplary embodiment, the compound is according to Formula (I), a pharmaceutically acceptable salt, solvate, and/or ester thereof, and a pharmaceutically acceptable excipient.

In still an additional embodiment, this invention is directed to a method of treating a disease (or disorder or condition) in an animal in need of such treatment, wherein the physiological disorder, symptom, or disease is granulocytopenia, anemia, thrombocytopenia, lymphopenia, or combination thereof (pancytopenia) resulting from causative factors selected from the group consisting of immune thrombocytopenic purpura, cancer chemotherapy, surgery, bone marrow or stem cell transplantation, radiation injury or treatment, severe bacterial infections, chronic viral infection, systemic lupus erythematosus, rheumatoid arthritis, and treatment with other drugs causing pancytopenias, which method comprises administering to said animal a pharmaceutical composition comprising a therapeutically effective amount of a compound described herein, a pharmaceutically acceptable salt, solvate and/or ester thereof, and a pharmaceutically acceptable excipient. In an exemplary embodiment, the compound has a structure according to a formula described herein. In an exemplary embodiment, the compound is according to Formula (I), a pharmaceutically acceptable salt, solvate, and/or ester thereof, and a pharmaceutically acceptable excipient.

In still an additional embodiment, the present invention is directed to a method of treating a disease (or disorder or condition) in an animal in need of such treatment, wherein the physiological disorder, symptom, or disease is thrombocytopenia resulting from causative factors selected from the group consisting of immune thrombocytopenic purpura, cancer chemotherapy, treatment with other drugs causing thrombocytopenia, surgery, liver transplantation, bone marrow or stem cell transplantation, radiation treatment or injury, severe bacterial infection, chronic viral infection, systemic lupus erythematosus, rheumatoid arthritis, hepatitis C viral infection, human immunodeficiency virus infection, myelodysplastic syndrome, and blood loss or withdrawal, which method comprises administering to said animal a therapeutically effective amount of a compound and/or pharmaceutical composition described herein, wherein the effective amount of said compound and/or pharmaceutical composition results in an expansion in the numbers of platelets through the growth of hematopoietic progenitor cells in said animal in need of such treatment. In an exemplary embodiment, the compound has a structure according to a formula described herein. In an exemplary embodiment, the compound is according to Formula (I), a pharmaceutically acceptable salt, solvate, and/or ester thereof, and a pharmaceutically acceptable excipient.

In still an additional embodiment, this invention is directed to a method of expanding stem cells and hematopoietic progenitor cells by subjecting stem cells and hematopoietic progenitor cells to effective amount of a compound and/or pharmaceutical composition described herein in culture or in an animal, to thereby induce the growth of the stem cells and hematopoietic progenitor cells in culture or in an animal in need of such stem cells or hematopoietic progenitor cells. In an exemplary embodiment, the compound has a structure according to a formula described herein. In an exemplary embodiment, the compound is according to Formula (I), a pharmaceutically acceptable salt, solvate, and/or ester thereof, and a pharmaceutically acceptable excipient.

All publications, including but not limited to patents and patent applications, cited in this specification are herein incorporated by reference as though fully set forth.

Reference to the embodiments set forth above is meant to include all combinations of particular and preferred groups unless otherwise stated. A person of ordinary skill in the art would recognize that certain groups listed above in the preferred embodiments can exist as geometric or stereoisomers.

The present invention includes individual stereoisomers and geometric isomers and mixtures thereof.

Methods of Making the Compounds

Compounds of this invention can be made by the synthetic procedures described below.

The starting materials and reagents used in preparing these compounds are either available from commercial suppliers such as Aldrich Chemical Co. (Milwaukee, Wis.), or Bachem (Torrance, Calif.), or are prepared by methods known to those skilled in the art following procedures set forth in references such as *Fieser and Fieser's Reagents for Organic Synthesis*, Volumes 1-17 (John Wiley and Sons, 1991); *Rodd's Chemistry of Carbon Compounds*, Volumes 1-5 and Supplementals (Elsevier Science Publishers, 1989); *Organic Reactions*, Volumes 1-40 (John Wiley and Sons, 1991), March's *Advanced Organic Chemistry*, (John Wiley and Sons, 4$^{th}$ Edition) and Larock's *Comprehensive Organic Transformations* (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C. Unless otherwise stated (as in the case of an hydrogenation), all reactions are performed under an atmosphere of nitrogen.

Compounds and/or compounds of formulas described herein that may be prepared through the syntheses described herein may exist as a single isomer or a mixture of isomers.

Compounds and/or compounds of formulas described herein (ie Formula I) where each A, B, $R^1$ and $R^2$ are as defined in the Summary of the Invention, can be prepared by reacting a compound of Formula VI:

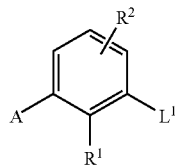

VI where $L^1$ is a substituent that consists of a reactive functional group, e.g., —NH$_2$, or —C(O)R$^{13}$, with an intermediate that contains a complementary reactive group, e.g., an enolizable carbon atom of the ring Q, —C(O)R$^{13}$, or —NH$_2$, respectively, to form the group L. Preferably $L^1$ is a reactive functional group selected from the group consisting of amino and trifluoromethyl ketone. The reactive group can be made to react under the conditions known to those skilled in the art with a complementary reactive group.

For example, compounds and/or compounds of formulas described herein (such as Formula I) in which L is an azo bond, Q is pyrazolone, and $R^1$, $R^2$, A and B are as defined in the Summary of the Invention, can be prepared according to procedures known to those skilled in the art and described by references contained in *Color Chemistry: Syntheses, Properties, and Applications of Organic Dyes and Pigments*, 3$^{rd}$ Edition, (Wiley-VCH, 2003). For example, compounds of Formula II(a) can be prepared by diazotizing an amine such as compounds of formula 1 in the presence of sodium nitrite followed by coupling the diazonium intermediate with the corresponding pyrazolone of formula 2, as in the following reaction scheme:

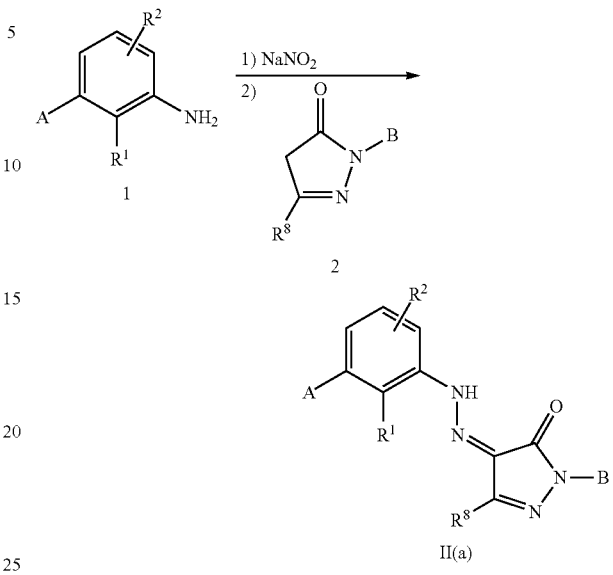

The reaction can be carried out first in the presence of the sodium nitrite and an acid such as aqueous HCl in a suitable reaction solvent such as water or aqueous ethanol, followed by the pyrazolone of formula 2 and a suitable base such as sodium hydrogen carbonate to arrive at a pH in the range of 7-8 to provide II(a). The substituent $R^8$ is as defined in the Detailed Description of the Invention.

Similarly, for example, compounds and/or compounds of formulas described herein (such as Formula I) in which L is an azo bond, Q is hydroxypyridone, and $R^1$, $R^2$, A and B are as defined in the Summary of the Invention, can be prepared in an analogous procedure by coupling a similar diazonium intermediate with a hydroxypyridone such as compounds of formula 3, as in the following reaction scheme:

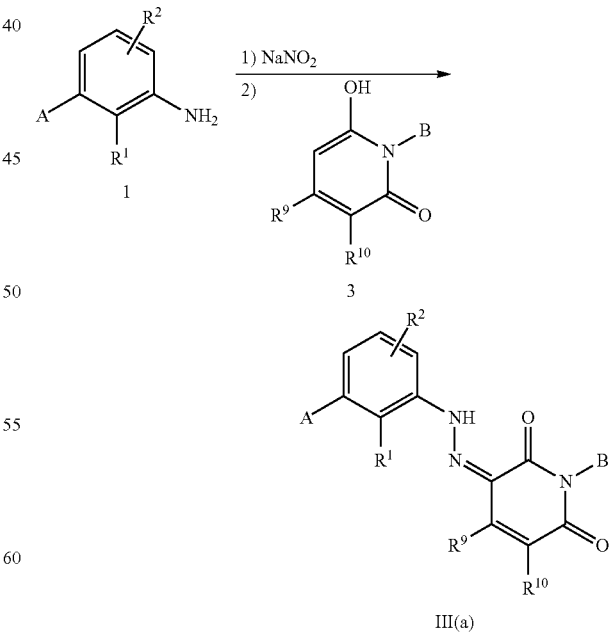

The substituents $R^9$ and $R^{10}$ are as defined in the Detailed Description of the Invention.

Similarly, for example, compounds and/or compounds of formulas described herein (such as Formula I) in which L is an azo bond, Q is imidazolinone, and $R^1$, $R^2$, A and B are as defined in the Summary of the Invention, can be prepared in an analogous procedure by coupling a similar diazonium intermediate with imidazolinone such as compounds of formula 4, as in the following reaction scheme:

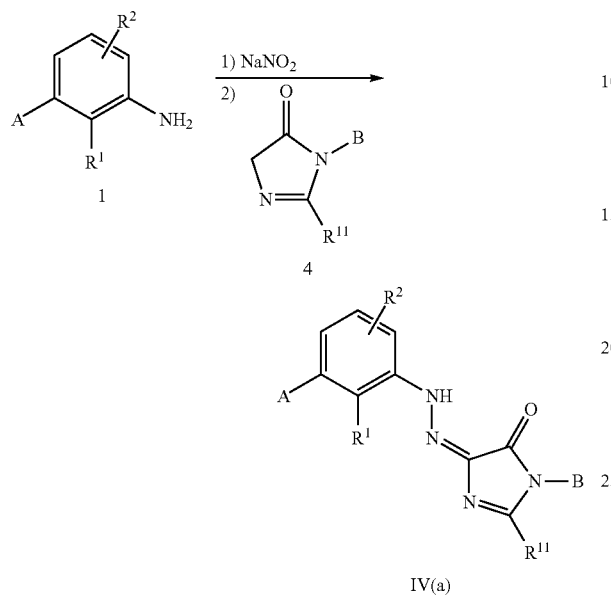

The substituent $R^{11}$ is as defined in the Detailed Description of the Invention.

Similarly, for example, compounds and/or compounds of formulas described herein (such as Formula I) in which L is an azo bond, Q is pyrrolidinedione, and $R^1$, $R^2$, A and B are as defined in the Summary of the Invention, can be prepared in an analogous procedure by coupling a similar diazonium intermediate with pyrrolidinedione, such as compounds of formula 5, as in the following reaction scheme:

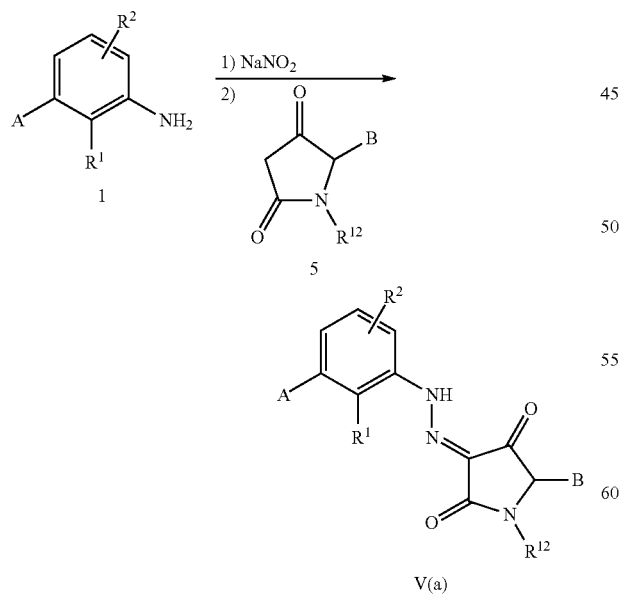

The substituent $R^{12}$ is as defined in the Detailed Description of the Invention.

Compounds and/or compounds of formulas described herein (such as Formula I) where L is haloalkyleneamine, preferably trifluoromethylamino, Q is pyrazolone, and $R^1$, $R^2$, A, and B are as defined in the Summary of the Invention, can be prepared by reductive amination, proceeding as in the following reaction scheme:

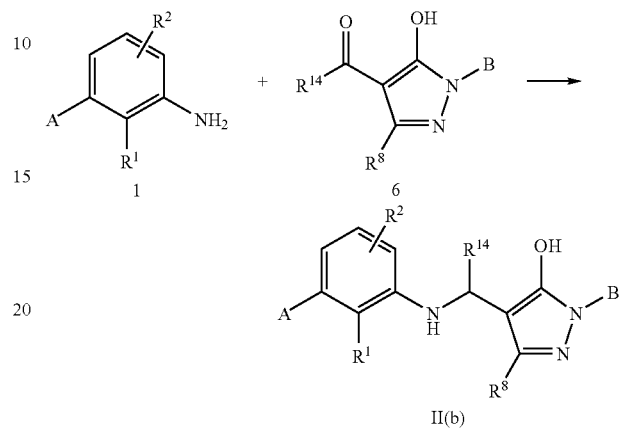

Reaction of an amine of formula 1 where A and $R^1$ are as defined in the Summary of the Invention with a ketone of formula 6 where $R^{14}$ is a haloalkyl (preferably trifluoromethyl) and $R^8$ is as defined in the Detailed Description of the Invention under reductive amination reaction conditions can provide a compound described herein (such as formula II(b)). The reaction is carried out in the presence of a suitable dehydrating agent such as $TiCl_4$, magnesium sulfate, isopropyl trifluoroacetate, in the presence of a base such as diisopropylethylamine, pyridine, and the like and in a suitable organic solvent such as methylene chloride to give an imine. The imine is reduced with a suitable reducing agent such as sodium borohydride, sodium cyanoborohydride, and the like in a suitable organic solvent such as methanol, tetrahydrofuran and the like.

Compounds of formula 6 such as 1-(3,4-dimethylphenyl)-5-hydroxy-3-methyl-4-trifluoroacetyl-1H-pyrazole, for example, can be prepared by acylation reaction conditions well known in the art from a corresponding pyrazolone with no 4-position substituent, such as compounds of the formula 2, as illustrated in the reference: B. S. Jensen, Acta Chim. Scand. 1959, 13, 1669. Alternatively, compounds of formula 6 can be prepared by reacting compounds of formula 2 with a carboxylic acid, such as acetic acid, in the presence of a suitable coupling agent, e.g., dicyclohexylcarbodiimide, in a suitable solvent such as tetrahydrofuran, ethyl acetate, and the like. The reaction is typically carried out with warming at 50 to 100° C., preferably 50° C.

Alternatively, compounds of formula II(b) can be prepared as illustrated in the reaction scheme below:

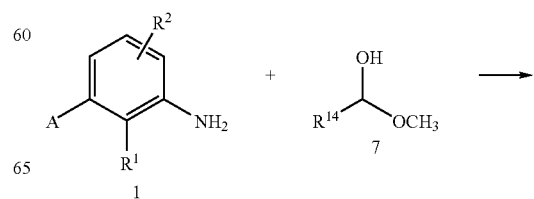

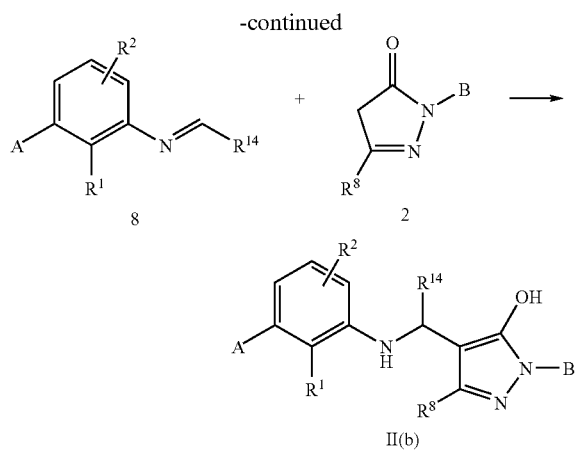

II(b)

Reaction of a compound of formula 1 where A, $R^1$ and $R^2$ are as defined in the Summary of the Invention (preferably $R^1$ and any substituents in A are protected with a suitable protecting group) with a hemiacetal of formula 7 where $R^{14}$ is haloalkyl, preferably trifluoromethyl, provides an imino compound of formula 8. Reaction of compound of formula 8 with a pyrazolone of formula 2 in the presence of a suitable base, e.g., diisopropylethylamine, pyridine, sodium ethoxide, and the like, in a suitable reaction solvent, e.g., ethanol, provides compound II(b). Suitable amino and alcohol protecting groups and reaction conditions for putting them on and removing them can be found in Greene, T. W., and Wuts, P. G. M. *Protecting Groups in Organic Synthesis*, John Wiley & Sons, Inc. 1999. Other examples of preparing compounds of formula II(b) by analogous procedures are described in the PCT Application Publication No. WO 2005/028429 and references therein.

Intermediates of a formula described herein (such as Formula 1) where each A, $R^1$, and $R^2$ are as defined in the Summary of the Invention can be prepared as in the following reaction scheme:

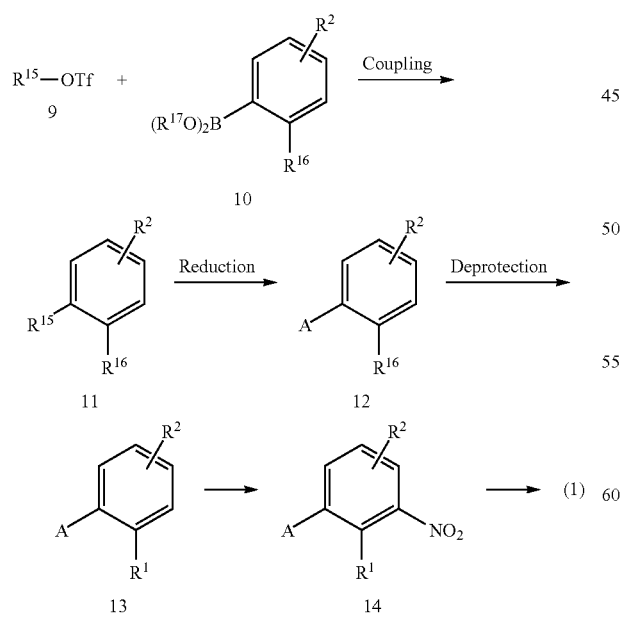

The compound of formula 9 is a vinyl triflate, consisting of a substituted trifluoromethylsulfonyloxy-cycloalken-1-yl or a substituted or unsubstituted trifluoromethylsulfonyloxy-heterocycloalken-1-yl where substituents in $R^{15}$ or attached to heteroatoms contained in $R^{15}$ are protected with a suitable protecting group, as described in Greene, T. W., and Wuts, P. G. M. *Protecting Groups in Organic Synthesis*, John Wiley & Sons, Inc. 1999. Preferably, a compound of formula 9 is 1-(trifluoromethylsulfonyloxy)-4-ethoxycarbonylcyclohexene, or 2-(1,2,5,6-tetrahydro-4-trifluoromethylsulfonyloxy-pyridin-1-yl)acetic acid ethyl ester. In some cases, $R^{16}$ is the same as $R^1$, and in some cases, $R^{16}$ is a protected intermediate form of $R^1$, e.g., alkoxy, aralkyloxy, or alkoxyalkoxyalkyloxy, preferably methoxy, benzyloxy, or methoxyethoxymethyloxy where such protecting groups can be removed by methods well known in the art.

The compound of formula 9 can be reacted with a boronic acid or ester of formula 10, where $R^{17}$ is hydrogen or alkyl, preferably hydrogen, under coupling conditions in the presence of a suitable catalyst, e.g., palladium(II) acetate, or tris(dibenzylideneacetone)dipalladium(0), with a suitable ligand, e.g., tricyclohexylphosphine, tri-tert-butylphosphine, or triphenylphosphine, to provide a compound of formula 11. A suitable reaction solvent is tetrahydrofuran or 1-methyl-2-pyrrolidinone, and the like, and a suitable base is potassium fluoride, potassium hydrogen phosphate, and the like. Typical procedures for the transformation are described, for example, in Little, A. F., et al., *J. Am. Chem. Soc.* 2000, 122, 4020. Boronic acids of formula 10 can be prepared by methods known in the art, or are commercially available, e.g., 2-methoxyphenyl boronic acid. The resulting olefin of formula 11 is treated under reducing conditions by methods well known in the art, with a suitable catalyst, e.g., palladium on charcoal, and is then treated under deprotecting conditions with a suitable deprotecting agent, e.g., aqueous hydrobromic acid, HBr in acetic acid, aqueous hydrochloric acid, and the like, to provide a corresponding compound of formula 13. Nitration can be carried out in the presence of a suitable nitrating agent, e.g., nitric acid in sulfuric acid or sodium nitrite in trifluoroacetic acid, to provide a compound of formula 14, which can then be allowed to reduce to the desired amine of Formula 1 using standard reducing conditions well know in the art, e.g., using a reducing metal catalyst, e.g., iron, tin chloride, palladium on charcoal, and the like, in a solvent such as ethanol under a hydrogen gas atmosphere.

Alternatively, intermediates of formulas described herein (such as Formula I) can be prepared by proceeding with methods analogous to those described in the reference, González-Bobes, F. and Fu, G. C. *J. Am. Chem. Soc.* 2006, 128, 5360 and illustrated in the following reaction scheme:

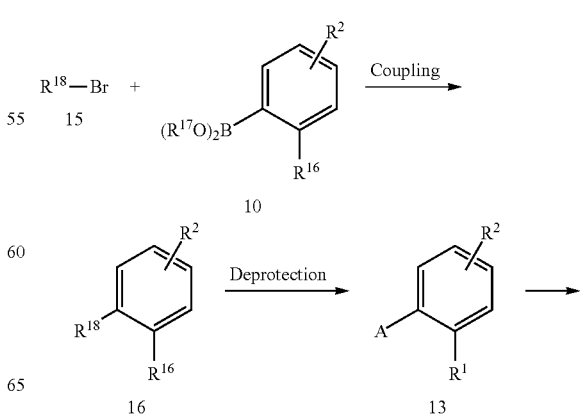

-continued

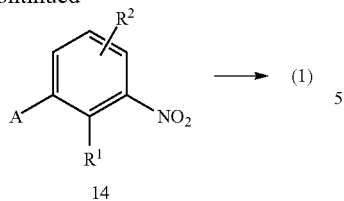

14

A boronic acid or ester of formula 10 can be coupled with a substituted halocycloalkyl or a substituted or unsubstituted halo heterocycloalkyl of formula 15 under suitable coupling conditions, preferably where the halo is chlorine or bromine, preferably bromine, and where substituents in $R^{18}$ or attached to heteroatoms contained in $R^{18}$ are protected with a suitable protecting group, as described in Greene, T. W., and Wuts, P. G. M. *Protecting Groups in Organic Synthesis*, John Wiley & Sons, Inc. 1999. Preferably, a compound of formula 15 is 3-bromocyclohexanecarboxylic acid ethyl ester, which can be prepared from the carboxylic acid as described in the reference Siegel, S., et al., J. Am. Chem. Soc. 1953, 75, 3857, or 4-bromo-1-(2,2,2-trifluoroethyl)piperidine. $R^{16}$ is as described herein.

The compound of formula 15 can be coupled with a boronic acid or ester of formula 10, where $R^{17}$ is as described herein, in the presence of a suitable active catalyst, e.g., $NiI_2$/trans-2-aminocyclohexanol, to provide a coupled compound of formula 16. A suitable reaction solvent is isopropanol, and a suitable base is sodium bis(trimethylsilylamide), for example. Compounds of formula 16 then can be treated under deprotecting conditions with a suitable deprotecting agent, e.g., aqueous hydrobromic acid, HBr in acetic acid, aqueous hydrochloric acid, and the like, to provide a corresponding compound of formula 13. These compounds of formula 13 then can be nitrated and reduced to provide amino compounds of Formula 1 as described herein.

Alternatively, intermediates of a formula described herein (such as Formula I) can be prepared by proceeding with methods analogous to those described in the references Itooka, R et al., J. Org. Chem. 2003, 68, 6000 and Sakai, M, et al., Organometallics, 1997, 16, 4229 and illustrated in the following reaction scheme:

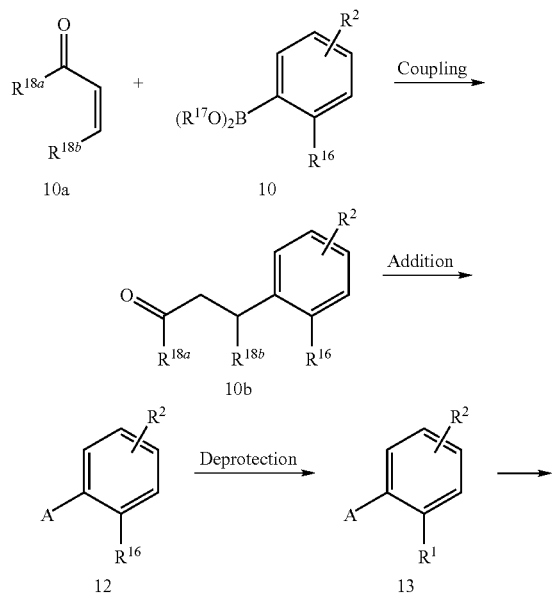

-continued

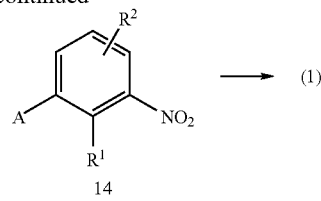

14

A boronic acid or ester of formula 10 can be coupled with a substituted or unsubstituted, acyclic or cyclic enone of formula 10a under suitable coupling conditions, preferably where R18a and R18b taken together with the carbons to which they are attached form a 3 to 8 membered a,b-unsaturated cyclic carbonyl compound. Preferably a compound of formula 10a is 2-cyclohexen-1-one. R2 and R16 are as described herein. A compound of formula 10a can be coupled with a boronic acid or ester of formula 10, where R17 is as described herein, in the presence of a suitable active catalyst, e.g., $Rh(acac)(CO)2$ or $[RhCl(cod)]2$, to provide a coupled compound of formula 10b. A suitable reaction solvent is aqueous N,N-dimethylformamide, methanol, 1,2-dimethoxyethane, or dioxane, preferably 6:1 dioxane-water, and a suitable base is sodium bicarbonate or potassium hydroxide, for example.

The carbonyl group in compounds of formula 10b can then be converted into other functional groups under conditions to which ketones are generally reactive to provide a compound of formula 12. For example, using standard reducing conditions well known in the art, e.g., palladium on charcoal, sodium borohydride or lithium aluminum hydride, a hydroxyl substituent can be prepared. By heating the ketone in hydrazine and a base, e.g., sodium hydroxide, reduction of the carbonyl to methylene can be achieved. An amino group can be produced through reductive amination by treating the carbonyl with an alkylamine, e.g., methylamine or benzylamine, in the presence of a reducing agent such as sodium cyanoborohydride, in a suitable solvent such as methanol. Preferably, the carbonyl group can be homologated under conditions analogous to those that are described in the references Badham, N. F. et al., J. Org. Chem. 2002, 67, 5440 and Oldenziel, O. H. et al., J. Org. Chem. 1977, 42, 3114, in which the compound of formula 10b is treated with a suitable nucleophile, e.g., chloroacetonitrile or tosylmethyl isocyanide, in the presence of a base such as potassium tert-butoxide, in a suitable solvent, e.g., tert-butanol or 1,2-dimethoxyethane. The resulting addition product from treatment with chloroacetonitrile can be further allowed to react in the presence of lithium bromide and water to afford a carboxylic acid compound of formula 12. In some cases, the carboxylic acid can exist as a mixture of stereoisomers. The coupling reaction of compounds of formula 10 and 10a can be carried out in the presence of a chiral ligand, e.g., R- or S-2,2'-bis(diphenylphosphino)-1,1'-binaphthyl (BINAP), under conditions analogous to those described in the reference Hayashi, T. et al., Org. Syn. Coll. Vol. 10, p. 609 (2004), to provide a chiral 1,4-addition product of formula 12.

Compounds of formula 12 then can be treated under deprotecting conditions with a suitable deprotecting agent, e.g., HBr in acetic acid, aqueous hydrochloric acid, and the like, to provide a corresponding compound of formula 13. These compounds of formula 13 then can be nitrated and reduced to provide amino compounds of Formula 1 as described herein.

Alternatively, intermediates of Formula 1 can be prepared by proceeding with methods analogous to those described in the reference, Phukan, P. et al., J. Chem. Soc. Perkin Trans. 1, 1999, 3015, and illustrated in the following reaction scheme:

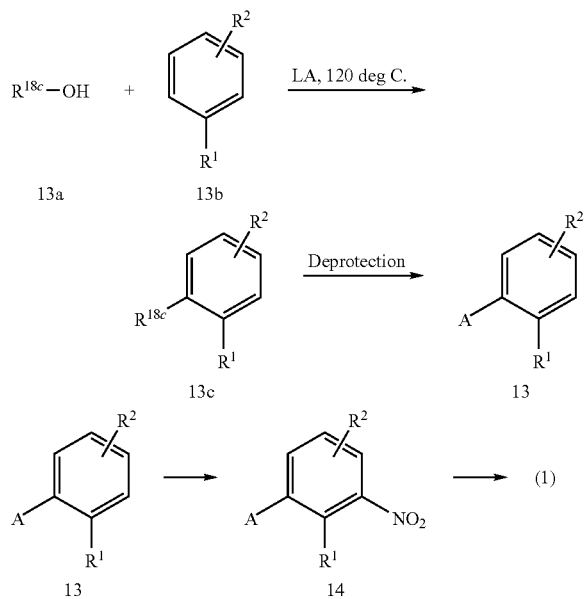

A phenyl compound of formula 13b, e.g., R1 is hydroxyl, can be coupled neat with a substituted or unsubstituted hydroxycycloalkyl or substituted or unsubstituted hydroxyheterocycloalkyl of formula 13a in the presence of a Lewis acid catalyst such as montmorillonite K10 clay and with heating between 50 and 150 deg C., preferably 120 deg C, to provide a substituted phenyl compound of formula 13c. Alternatively, a compound of formula 13b can be coupled with a substituted or unsubstituted halocycloalkyl or a substituted or unsubstituted halo heterocycloalkyl under suitable coupling conditions, preferably where the halo is chlorine, the formula is R18c-Cl, and the Lewis acid is aluminum chloride. Preferably, substituents in R18c or attached to heteroatoms contained in R18c are protected with a suitable protecting group, as described in Greene, T. W., and Wuts, P. G. M. Protecting Groups in Organic Synthesis, John Wiley & Sons, Inc. 1999. Compounds of formula 13c can then be treated under deprotecting conditions with a suitable deprotecting agent, as described in the Greene and Wuts reference, to provide a corresponding compound of formula 13. These compounds of formula 13 then can be nitrated and reduced to provide amino compounds of Formula 1 as described herein.

Substituted heterocyclic intermediate compounds of formula 2, 3, 4, and 5 as described herein, each comprising the groups Q-B of compounds for Formula I, can be prepared by methods known in the art.

For example, when Q is a pyrazolone moiety, an intermediate compound of formula 2 can be prepared by proceeding as in the reaction scheme below:

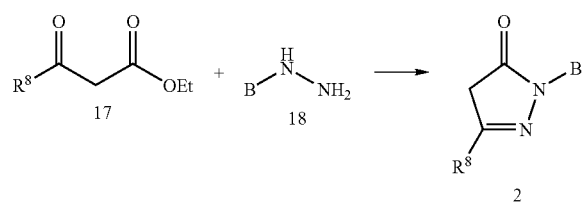

A β-keto ester compound of formula 17, where $R^8$ is as described in the Detailed Description of the Invention, can be reacted with a hydrazine of formula 18 or its hydrochloride salt in a suitable reaction solvent, e.g., acetic acid, to provide a pyrazolone compound of formula 2. The reaction can be carried out at 80° C. to 120° C., preferably 100° C. Where B is aryl as defined in the Summary of the Invention, compounds of formula 18 are commercially available, and methods for reacting them with compounds of formula 17 are described, for example, in PCT Application Publication No. WO 2001/089457. Where B is cycloalkyl as defined in the Summary of the Invention, compounds of formula 18 are commercially available, and methods for reacting them with compounds of formula 17 are described, for example, in PCT Application Publication No. WO 2003/103686. Where B is heterocycloalkyl and heteroatoms within B are protected with a suitable protecting group, methods for reacting them with compounds of formula 18 are analogous to those described in PCT Application Publication No. WO 2003/103686, for example.

Alternatively, where B is heterocycloalkyl and contains phosphorous, intermediates of formula 2 can be prepared by proceeding with methods analogous to those described in PCT Application Publication No. WO2007/087068, herein incorporated by reference in its entirety, and illustrated in the reaction scheme below:

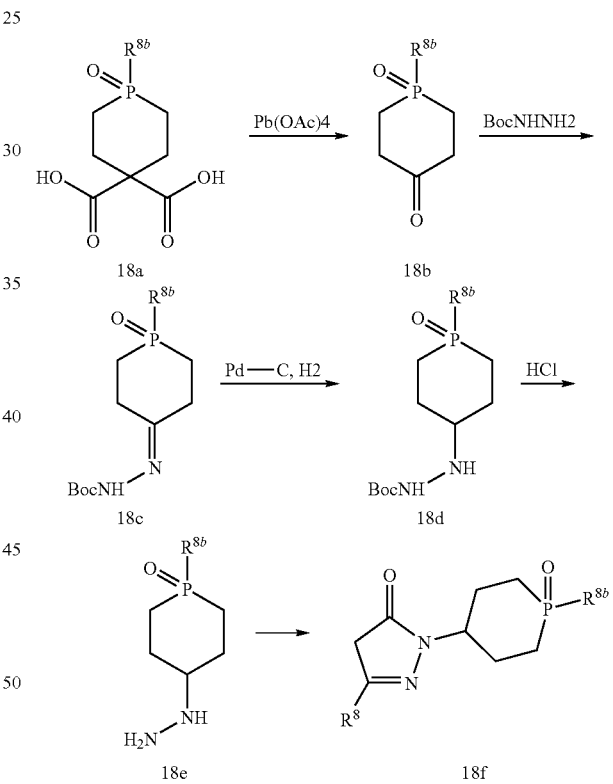

Compounds of formula 18a with alkyl, cycloalkyl, aryl, heteroaryl, heterocycloalkyl substituents R8b and the like can be prepared by methods as described in WO2007/087068 from divinyl phosphine oxides, and can be oxidatively decarboxylated to form ketones of formula 18b in the presence of an oxidizing agent such as lead (IV) tetraacetate in a suitable solvent such as methylene chloride. Hydrazones of formula 18c can be prepared by reacting compounds of formula 18b in the presence of nucleophiles such as tert-butylcarbazate in a suitable solvent such as ethyl acetate or methylene chloride. The resulting hydrazone of formula 18c can be treated under reducing conditions, e.g., palladium on charcoal, in a solvent, such as ethanol, to provide protected a hydrazine of formula 18d. Deprotection of the hydrazine under suitable deprotection conditions, e.g., hydrochloric acid or trifluoroacetic acid in a solvent such as methylene chloride, can provide hydrazines of formula 18e, and the reaction of hydrazines with ketones of formula 17 such as ethyl acetoacetate in a solvent such as acetic acid can provide pyrazolones of formula 18f as described herein.

Similarly, when Q is a hydroxypyridone moiety, for example, an intermediate compound of formula 3 can be prepared by proceeding as in the reaction scheme below:

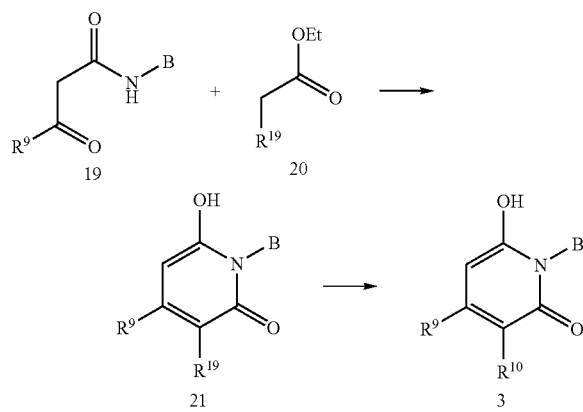

where $R^9$ is as defined in the Detailed Description of the Invention, preferably alkyl, preferably methyl, B is as defined in the Summary of the Invention, and $R^{19}$ is an electron withdrawing group, for example, cyano, alkoxycarbonyl, aminocarbonyl, and the like, preferably ethoxycarbonyl. General methods for preparing and reacting analogous hydroxypyridone moieties are known in the art and represented in such example references as U.S. Pat. Nos. 4,359,418 and 3,956,265 and British Patent Specification No. 1,296,857. A compound of formula 19, which is commercially available or can be prepared from a commercially available keto-ester and an amine, can be reacted with a compound of formula 20 in a suitable reaction solvent such methanol, ethanol, and the like, or in the absence of solvent, at a reaction temperature of 50° C. to 200° C., preferably 100-150° C. The resulting compound of formula 21 can be used directly, where $R^{19}$ is the same as $R^{10}$, or it may be reacted further, for example, through removal of a protecting group in suitable deprotection conditions. For example, a group of $R^{19}$ such as ethoxycarbonyl can be thermally decarboxylated in the presence of an acid such as aqueous HCl, and the resulting intermediate can be reacted further with paraformaldehyde and dialkylamines to provide a compound of formula 3 where $R^{10}$ is dialkylaminoalkyl. Other suitable reactions to provide compounds of formula 3 are contemplated herein.

Similarly, when Q is an imidazolinone moiety, for example, an intermediate compound of formula 4 can be prepared by proceeding as in the reaction scheme below:

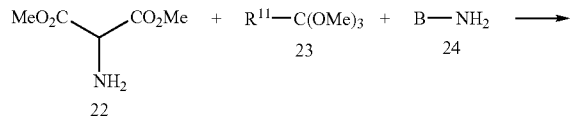

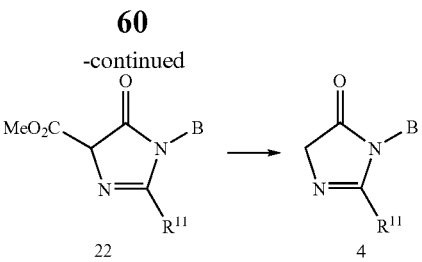

where B and $R^{11}$ are as defined in the Detailed Description of the Invention. An amino compound of formula 22 can be reacted with orthoesters of formula 23 under acid catalysis, e.g., trifluoroacetic acid, and amines of formula 24, in a suitable reaction solvent, e.g., methanol, isopropanol and the like, to provide imidazolinones of formula 22. Compounds of formula 22 contain carbonyl moieties which can be removed under thermal decarboxylation conditions, e.g., aqueous acids such as HCl, at 50-100° C., and can provide compounds of formula 4 following such treatment. Procedures for analogous reactions to prepare imidazolinones are described in *J. Org. Chem.* 1985, 50, 5111.

Similarly, when Q is a pyrrolidinedione moiety, for example, an intermediate compound of formula 5 can be prepared by proceeding as in the reaction scheme below:

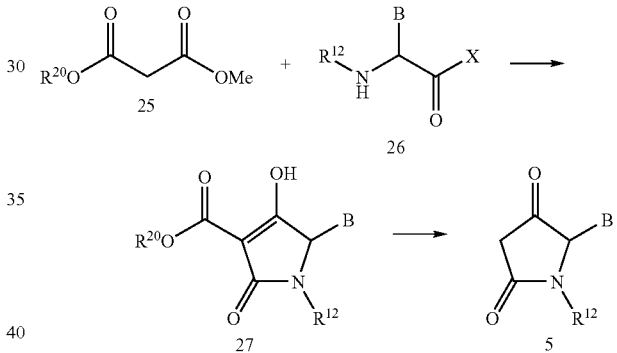

where B and $R^{12}$ are as defined in the Detailed Description of the Invention, $R^{20}$ is a alkyl or aryl, preferably alkyl, preferably methyl or ethyl. Compounds of formula 25 are either commercially available or can be prepared by methods well known in the art. For example, dimethyl malonate and diethyl malonate are commercially available. Compounds of formula 26 are either commercially available or can be prepared by methods well known in the art. Where X is OH, for example, phenylglycine, sarcosine, N-methylphenylglycine, and cyclohexylalanine are commercially available. Compound of formula 26 can then be converted to an activated acid where X is a leaving group, e.g., chloride, fluoride, p-nitrophenol, N-hydroxysuccinimidyl, and the like, which upon reaction with compound 25 in the presence of a suitable reaction base, e.g., sodium hydride, potassium tert-butoxide, and the like, can provide a compound of formula 27. Analogous methods for the preparation of 2,4-pyrrolidinediones are as described in the references, provided as examples, Detsi, A et al., *J. Chem. Soc., Perkin Trans* 11998, 2443-2449; and Poschenrieder, H, et al., *Arch. Pharm. Pharm. Med. Chem.* 1998, 331, 389-394. When $R^{20}$ is methyl or ethyl, compounds of formula 27 can be treated with water at 50° C. to 150° C., preferably 75° C., to provide the decarboxylated compounds of formula 5, which are then useful as intermediates in the preparation of other compounds as described herein.

A compound of a formula described herein (such as Formula (I)) can be converted to other compounds of a formula described herein (such as Formula (I)). For example:

A compound of a formula described herein (such as Formula (I)) where A and B are aromatic rings substituted with halo can be reacted with appropriate boronic acids under palladium catalyzed Suzuki coupling reaction conditions to provide correspond compounds of Formula (I) where A and B are further substituted with an aryl or heteroaryl ring. A compound of a formula described herein (such as Formula (I)) containing a hydroxy group may be prepared by dealkylation/benzylation of an alkoxy/benzyloxy substituent; those containing an acid group, by hydrolysis of an ester group; and those containing a cyano, by displacement of a bromine atom on the corresponding compounds of a formula described herein (such as Formula (I)). A compound of a formula described herein (such as Formula (I)) containing a halo group such as chloro can be converted to a corresponding compound of a compound of a formula described herein (such as Formula (I)) containing an methylthio by treating it with sodium thiomethoxide. The methylthio group can be oxidized to methylsulfonyl using a suitable oxidizing agent such as OXONE®. A compound of a formula described herein (such as Formula (I)) containing a cyano group can be converted to a corresponding carboxy containing compound by hydrolysis of the cyano group. The carboxy group, in turn, can be converted to an ester group.

A compound of a formula described herein (such as Formula (I)) can be prepared as a pharmaceutically acceptable acid addition salt by reacting the free base form of the compound with a pharmaceutically acceptable inorganic or organic acid. Alternatively, a pharmaceutically acceptable base addition salt of a compound of a formula described herein (such as Formula (I)) can be prepared by reacting the free acid form of the compound with a pharmaceutically acceptable inorganic or organic base. Inorganic and organic acids and bases suitable for the preparation of the pharmaceutically acceptable salts of a compound of a formula described herein (such as Formula (I)) are set forth in the definitions section of this Application. Alternatively, the salt forms of the compound of a formula described herein (such as Formula (I)) can be prepared using salts of the starting materials or intermediates.

The free acid or free base forms of a compound of a formula described herein (such as Formula (I)) can be prepared from the corresponding base addition salt or acid addition salt form. For example, a compound of a formula described herein (such as Formula (I)) in an acid addition salt form can be converted to the corresponding free base by treating with a suitable base (e.g., ammonium hydroxide solution, sodium hydroxide, and the like). A compound of a formula described herein (such as Formula (I)) in a base addition salt form can be converted to the corresponding free acid by treating with a suitable acid (e.g., hydrochloric acid, etc). The N-oxides of compound of a formula described herein (such as Formula (I)) can be prepared by methods known to those of ordinary skill in the art. For example, N-oxides can be prepared by treating an unoxidized form of the compound of a formula described herein (such as Formula (I)) with an oxidizing agent (e.g., trifluoroperacetic acid, pennaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compound of a formula described herein (such as Formula (I)) can be prepared from the N-oxide of an appropriate starting material. Compounds of a formula described herein (such as Formula (I)) in unoxidized form can be prepared from N-oxides of a compound of a formula described herein (such as Formula (I)) by treating with a reducing agent (e.g., sulfur, sulfur dioxide, triphenylphosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds of a formula described herein (such as Formula (I)) can be prepared by methods known to those of ordinary skill in the art (e.g., for further details see Saulnier et al., (1994), *Bioorganic and Medicinal Chemistry Letters*, Vol. 4, p. 1985). For example, appropriate prodrugs can be prepared by reacting a non-derivatized compound of a formula described herein (such as Formula (I)) with a suitable carbamoylating agent (e.g., 1,1-acyloxyalkylcarbono-chloridate, para-nitrophenylcarbonate, or the like).

Protected derivatives of the compounds described herein can be made by means known to those of ordinary skill in the art. A detailed description of the techniques applicable to the creation of protecting groups and their removal can be found in Greene, T. W., and Wuts, P. G. M. *Protecting Groups in Organic Synthesis*, John Wiley & Sons, Inc. 1999.

Compounds of the present invention may be conveniently prepared or formed during the process of the invention, as solvates (e.g. hydrates). Hydrates of compounds of the present invention may be conveniently prepared by recrystallization from an aqueous/organic solvent mixture, using organic solvents such as dioxin, tetrahydrofuran or methanol.

Compounds of a formula described herein (such as Formula (I)) can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of a compound of a formula described herein (such as Formula (I)), dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, *Enantiomers, Racemates and Resolutions*, John Wiley & Sons, Inc. (1981).

Administration and Pharmaceutical Compositions

The treatment of thrombocytopenia or pancytopenia as described herein is accomplished by increasing the levels of platelets.

In general, a compound of a formula described herein (such as Formula (I)) will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. For example, therapeutically effective amounts of a compound of Formula (I) may range from about 1 microgram per kilogram body weight (µg/kg) per day to about 100 milligram per kilogram body weight (mg/kg) per day, typically from about 100 µg/kg/day to about 10 mg/kg/day. Therefore, a therapeutically effective amount for an 80 kg human patient may range from about 0.1 mg/day to about 8 g/day, typically from about 1 mg/day to about 800 mg/day. In general, one of ordinary skill in the art, acting in reliance upon personal knowledge and the disclosure of this Application, will be able to ascertain a therapeutically effective amount of a compound of Formula (I) for treating a given disease.

For intravenous formulations of the TPO mimetic of a formula described herein, the compound may be stored in the form of a solid (e.g., powder), optionally in combination with one or more other agents (e.g., corticosteroids such as prednisone and dexamethasone, cytotoxic agents such as cyclophosphamide and vincristine, and biologicals such as IV immunoglobulin, erythropoietin, granulocyte-colony stimulating factor, granulocyte/macrophage-colony stimulating factor or rh-IL-11), then reconstituted by the addition of a suitable liquid. Alternatively, the compound described herein may be stored as a solution or suspension (e.g., in a single use vial, a multiuse vial, or in a ready-to-use vial), optionally in combination with one or more other agents described herein. Alternatively, the solution or suspension of the compound described herein may be mixed, prior to administration, with the optional other agents, or the solution or suspension of the compound described herein may be administered separately from the solution or suspension of the other optional agents.

Oral formulations of the TPO mimetic described herein may be in the form of a pill or capsule. If combined with one or more agents (e.g., e.g., corticosteroids such as prednisone and dexamethasone, and cytotoxic agents such as cyclophosphamide and vincristine), the compound described herein and the one or more agents may be mixed together with pharmaceutically acceptable excipients, or may be combined in a layered structure (e.g., bilayer pill) to segregate the various active ingredients. Alternatively, the compound described herein and the optional other agents may be administered separately.

Pharmaceutical compositions may contain from about 0.1 to about 99.9 weight percent, or from about 5 to about 95 weight percent, or from about 20 to about 80 weight percent of active ingredient (compound described herein). For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: *The Science and Practice of Pharmacy*, 20th Edition, (2000), Lippincott Williams & Wilkins, Baltimore, Md., herein incorporated by reference.

Liquid form preparations include solutions, suspensions and emulsions, for example, water or water-propylene glycol solutions for parenteral injection or addition of sweeteners and opacifiers for oral solutions, suspensions, and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparations subdivided into suitably sized unit doses containing appropriate quantities of the active component, e.g., an effective amount to achieve the desired purpose.

For convenience, the total daily dosage may be divided and administered in portions during the day as required. The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.1 mg/day to about 2000 mg/day, in two to four divided doses.

The pharmaceutical compositions of the invention may be administered from about 1 to about 5 times per day, or alternatively, as a continuous infusion. Such administration can be used as a chronic or acute therapy.

The TPO mimetic can be administered in combination with further active ingredients known to treat thrombocytopenia, including thrombocytopenia associated with immune thrombocytopenic purpura, chemotherapy, chronic viral infection and its treatments, bone marrow transplantation, liver transplantation, and other conditions with lowered platelet production. The term "further active ingredients" as used herein includes any compounds or therapeutic agents that can demonstrate advantageous properties when administered with TPO or a TPO mimetic. Examples of a further active ingredient or ingredients for use in combination with the compounds of this Application include but are not limited to: corticosteroids, intravenous immunoglobulin IVIg and anti-D, hematopoietic growth factors, cell-cycle initiators, and chemotherapeutic agents.

Further active ingredients as defined herein for treatment of thrombocytopenias, as described in W. Stevens, et al., *Neth. J. Med.*, 2006, 64, 356, include: corticosteroids (e.g., prednisone and dexamethasone), immunoglobulins (e.g., IVIg and Anti-D), platelet clearance inhibitors such as danazol, tubulin modulators (e.g., vincristine and vinblastine), platinum anticancer agents (e.g., cisplatin and oxaliplatin), immunosuppressives (e.g., cyclophosphamide, cyclosporine, and azathioprine), the anti-CD20 antibody Rituximab, dapsone, and mycophenolate mofetil. Other non-limiting examples of such agents include therapeutically useful combinations of anticancer agents, such as CHOPP (cyclophosphamide, vincristine, prednisone, and procarbazine), CEP (cyclophosphamide, vincristine, and etoposide), and CVP (cyclophosphamide, vincristine, and prednisone). Other non-limiting examples of such agents include hematopoietic growth factors (Deutsch, V. R., et al., *Br. J. Haematol.* 2006, 134, 453) such as thrombopoietin, erythropoietin, granulocyte-colony stimulating factor, granulocyte macrophage-colony stimulating factor, interleukin-1, interleukin-3, interleukin-6, interleukin-11, stem cell factor, FLT ligand, fibroblast growth factor, stromal-derived factor-1, GATA-1, nuclear factor erythroid-2, and AMG-531, or a biologically active derivative of the aforementioned agents. Preferably, the compound of Formula (I) and the pharmaceutically acceptable excipient is administered in combination with one or more compound(s) independently selected from prednisone, intravenous immunoglobulin, anti-D, and IL-11.

As stated previously, the compound described herein can be administered in combination with cancer chemotherapy to provide relief from thrombocytopenia resulting from such chemotherapy. As described in Kuter, D. J., Begley, C. G., *Blood*, 2002, 100, 3457 and Sekhon, S. S., Roy, V. *South. Med. J.* 2006, 99, 491, certain non-limiting examples of such cancer chemotherapies include: vincristine, vinblastine, doxorubicin, ifosfamide, cyclophosphamide, paclitaxel, carboplatin, cisplatin, oxaliplatin, etoposide, adriamycin, gemcitabine, tamoxifen, sulindac, and the like.

As stated previously, hepatitis C viral infection is a causative factor associated with thrombocytopenia, and the compound described herein can also be administered in combination with one or more therapies used to treat hepatitis C viral infection, including interferon alpha and a viral protease inhibitor, ribavirin.

As stated previously, human immunodeficiency viral infection is a causative factor associated with thrombocytopenia, and the compound described herein can also be administered in combination with one or more therapies used to treat human immunodeficiency viral infection. Non-limiting examples of human immunodeficiency virus protease inhibitors include abacavir, CGP-73547, CGP-61755, DMP-450, indinavir, nelfinavir, tipranavir, ritonavir, saquinavir, ABT-378, AG 1776, and BMS-232,632. Examples of reverse transcriptase inhibitors include delaviridine, efavirenz, GS-840, HB Y097, lamivudine, nevirapine, AZT, 3TC, ddC, and ddI.

The quantity of TPO mimetic in combination with a corticosteroid, e.g., prednisone, in a unit dose of preparation may be from about 10 to about 300 mg of TPO mimetic combined with from about 10 to about 300 mg of corticosteroid. In another combination, the quantity of TPO mimetic in combination with a corticosteroid in a unit dose of preparation may be from about 50 to about 300 mg of TPO mimetic combined with from about 10 to about 100 mg of corticosteroid.

The TPO mimetic can also be administered in combination with certain procedures such as splenectomy and platelet transfusion, which are well known treatments for thrombocytopenia.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required. Upon improvement of a patient's condition, a maintenance dose of a compound, composition or combination of the invention may be administered, if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

Specific dosage and treatment regimens for any particular patient may be varied and will depend upon a variety of factors, including the activity of the specific compound employed, the age, body weight, general health status, sex and diet of the patient, the time of administration, the rate of excretion, the specific drug combination, the severity and course of the symptoms being treated, the patient's disposition to the condition being treated and the judgment of the treating physician. Determination of the proper dosage regimen for a particular situation is within the skill of the art.

Utility

The compounds of this invention are useful in the treatment of any disease or condition, such as thrombocytopenia, resulting in the decrease of blood platelets below what is considered to be normal for a healthy individual. There are several causative factors, e.g., autoimmunity, such as immune thrombocytopenic purpura, rheumatoid arthritis or systemic lupus erythematosus; radiation injury or treatment; surgical procedures, such as liver or bone marrow transplantation; stem cell transplantation and therapy; severe bacterial infections; chronic viral infection, such as hepatitis C and human immunodeficiency virus; myelodysplastic syndrome; thrombopoietin receptor deficiency; cancer chemotherapy; and treatment with other medications causing thrombocytopenia, such as interferon-alpha. Compounds of this invention are also useful in prophylaxis when the production of platelets is required, for example for platelet apheresis donors or patients scheduled to undergo chemotherapy.

Testing

The ability of the compounds of this invention to act as TPO mimetics can be determined using the in vitro assays described as examples below:

Luciferase Assay

The compounds of this invention can be assayed for their ability to stimulate luciferase activity in cultured TPO-responsive cells. For example, suitable cells and assay conditions for this procedure are as described in Nakamura, T. et al., *Blood*, 2006, 107, 4300 and Duffy, K. et al. *J. Med. Chem.* 2001, 44, 3730.

Proliferation Assay

The compounds of this invention can be assayed for their ability to stimulate the proliferation of cultured cells which are sensitive to TPO and TPO mimetics. For example, suitable cells for this assay are UT7/TPO which are TPO-dependent human megakaryocytic cells (Komatsu, N. et al., *Blood*, 1996, 87, 4552) and BaF/hTPOR which are transfected murine BaF cells expressing hTPO receptor (Park, H. and Hong, H. *Mol. Cells.* 1997, 7, 699.) Assays of compounds can be performed as described in U.S. Patent Application Publication No. 2003/0195231; Nakamura, T. et al., *Blood*, 2006, 107, 4300; Sakai, R., et al., *Bioorg. Med. Chem.* 2005, 13, 6388; Duffy, K. et al. *J. Med. Chem.* 2001, 44, 3730; and Cwirla, S. E. et al., *Science*, 1997, 276, 1696.

The activity of the mimetics can also be measured by using TPO receptor expressing human cell lines, such as Mole, using published methods (Yang et al., *Blood*, 1989, 74, 1880-4; Page et al., *Cytokine*, 1996, 8, 66-9). Moreover, bone marrow-derived progenitor cells are responsive to TPO and TPO mimetics. More specifically, CD34+ human progenitor cells can be used to assess the potencies of TPO and TPO mimetic compounds by measuring the growth of the cells cultured in the presence of increasing concentrations of the compounds (Ramsfjell et al., *J. Immunol.*, 1997, 158, 5169).

Differentiation Assay

The compounds of this invention can be assayed for their activity in inducing the differentiation of human megakaryocytes from human CD34+ hematopoietic precursor cells. Assays of compounds can be performed as described in Nakamura, T. et al., *Blood*, 2006, 107, 4300 and Duffy, K. et al. *J. Med. Chem.* 2001, 44, 3730.

EXAMPLES

The invention disclosed herein is exemplified by the following preparations and examples, which should not be construed to limit the scope of the disclosure. Alternative mechanistic pathways and analogous structures may be apparent to those skilled in the art.

Example 1

Preparation of 4-[2-(3-cyclohexyl-2-hydroxyphenyl)hydrazin-1-ylidene]-1-(3,4-dimethylphenyl)-3-methyl-4,5-dihydro-1H-pyrazol-5-one Step 1:

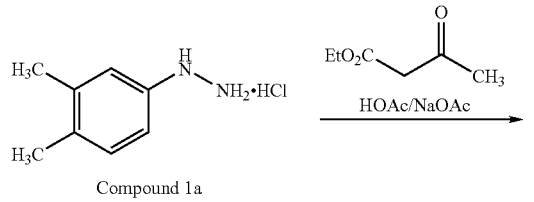

Compound 1a

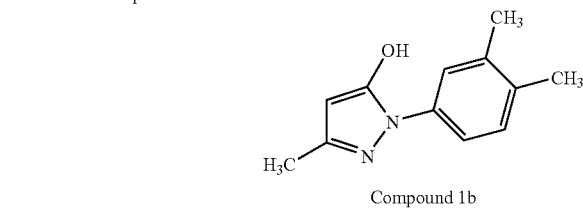

Compound 1b

Compound 1a (3,4-dimethylphenylhydrazine hydrochloride, Acros Catalog Number 408510250) (0.50 g, 2.9 mmol), ethyl acetoacetate (0.38 g, 2.9 mmol), and sodium acetate (0.24 g, 2.9 mmol) were heated in acetic acid (8 mL) to reflux at an oil bath temperature of 155 deg C. for 12 hours. The dark brown solution was allowed to cool, and the solvent was removed under reduced pressure. The brown residue was dissolved in ethyl ether (100 mL), washed sequentially with saturated sodium bicarbonate (3×10 mL), and saturated sodium chloride (3×10 mL) and dried over sodium sulfate. The solvent was removed under reduced pressure. The mixture was purified by silica gel chromatography with 40% ethyl acetate-hexanes as eluant to afford Compound 1b as a brown oil which solidified upon standing (0.43 g, 73%) (i.e., compound (v) in U.S. Pat. No. 7,160,870 B2 herein incorporated by reference in its entirety). $^1$H NMR (400 MHz, DMSO-d6) δ 11.24 (1H, s), 7.46 (1H, s), 7.39 (1H, dd, J=8.0, 2.0 Hz), 7.15 (1H, d, J=8.0 Hz), 5.34 (1H, s), 2.24 (3H, s), 2.21 (3H, s), 2.09 (3H, s).

Step 2:

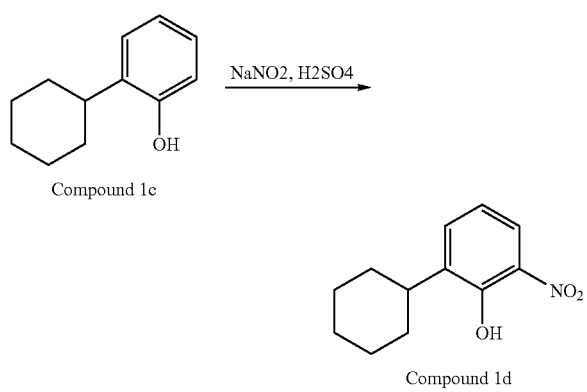

Compound 1c (2-cyclohexylphenol, TCI America Catalog Number C0732) (0.50 g, 2.8 mmol) was dissolved in ethyl ether (8 mL) and cooled to 0 deg C. Sodium nitrite (0.59 g, 8.6 mmol) and water (4 mL) were added and 2.4 N sulfuric acid (12 mL, 28.8 mmol) was added dropwise over 20 minutes with a bright yellow color formation. The mixture was allowed to stir 1 hr at 0 deg C. and 2 hr at 20 deg C., and then diluted with 125 mL of hexanes. The organics were washed with water (3×10 mL) and saturated sodium chloride (3×20 mL) and dried over sodium sulfate. The solvent was removed under reduced pressure and the mixture of isomers was separated using silica gel chromatography with a gradient of 5 to 15% ethyl acetate-hexanes as eluant. The ortho isomer Compound 1d was collected as a yellow oil (0.26 g, 40%) which matches the description in literature (i.e., compound 2.2.2.2 in publication D. R. Clifford, et al., Pest. Sci. 1972, 3, 575-584 herein incorporated by reference in its entirety). 1H NMR (400 MHz, DMSO-d6) δ 10.53 (1H, s), 7.85 (1H, dd, J=8.4, 1.6 Hz), 7.57 (1H, dd, J=7.6, 1.6 Hz), 7.01 (1H, t, J=7.6 Hz), 2.99 (1H, m), 1.81-1.70 (5H, m), 1.41-1.22 (5H, m).

Step 3:

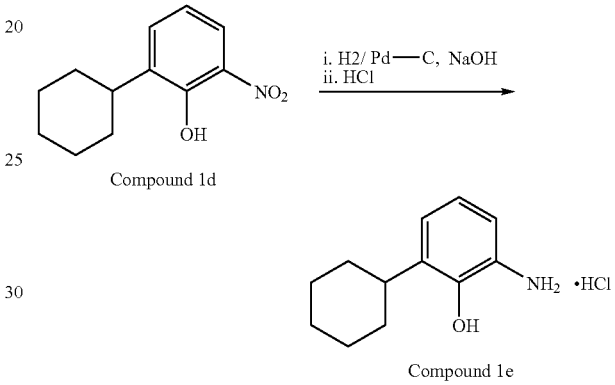

To compound 1d (0.25 g, 1.1 mmol) and 10% palladium on carbon (0.05 g) were added ethanol (6 mL), water (1 mL), and 3 N sodium hydroxide (0.75 mL, 2.2 mmol). The mixture was degassed briefly under reduced pressure and allowed to stir under hydrogen at 1 atm at 20 deg C. for 3 hr. The catalyst was removed by filtration. The red solution was treated with 1 mL of 1 M HCl, and the solvent removed under reduced pressure. The resulting red powder, Compound 1e (0.36 g), contained some salts and was used directly without further purification.

Step 4:

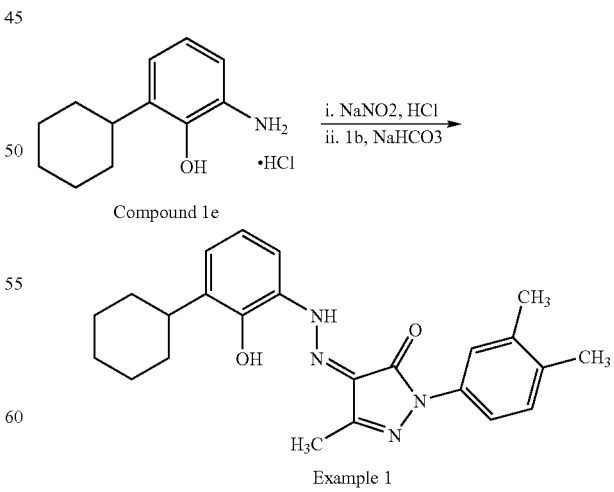

A red solution of Compound 1e (0.18 g of the crude powder, 0.56 mmol), 1 M HCl (1.6 mL, 1.6 mmol), and ethanol (2 mL) was cooled to 0 deg C. under nitrogen. A solution of 0.065 g of sodium nitrite in 1 mL of water was prepared separately and 0.63 mL (0.59 mmol of sodium nitrite) was added dropwise to the solution containing compound 1e with formation of a dark red-yellow color. The diazotization was monitored using TLC with 10% ethyl acetate-hexanes. Compound 1b was added after 0.5 h followed by sodium bicarbonate (0.24 g, 2.9 mmol) and additional ethanol (1 mL). The mixture was allowed to warm to 20 deg C., treated with additional sodium bicarbonate (0.084 g, 1.0 mmol) to adjust the pH to 7-8, and allowed to stir for 12 h. The mixture was diluted with ethyl acetate (100 mL), washed with saturated sodium chloride (2×20 mL), and dried over sodium sulfate. The solvent was removed under reduced pressure and the residue purified by silica gel chromatography (10% ethyl acetate-hexanes) to afford Example 1 (0.17 g, 74%). Electrospray MS [M+H]+ 405.3.

Example 2

Preparation of 4-[2-(3-cyclohexyl-2-hydroxyphenyl)hydrazin-1-ylidene]-1-(4-tert-butylphenyl)-3-methyl-4,5-dihydro-1H-pyrazol-5-one Step 1:

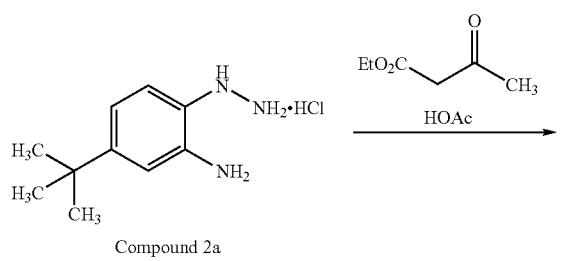

Compound 2a

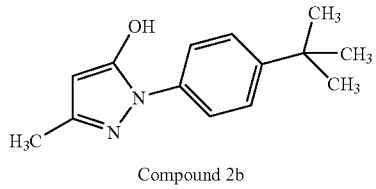

Compound 2b

Compound 2a (1-[4-(tert-butyl)phenyl]hydrazine hydrochloride, Maybridge Catalog Number BTB08670EA) (2.0 g, 10.0 mmol) and ethyl acetoacetate (1.95 g, 15.0 mmol) were heated in acetic acid (20 mL) to reflux at an oil bath temperature of 110 deg C. for 6 hours. The amber solution was allowed to cool, and the solvent was removed under reduced pressure. The residue was suspended in 40% ethyl acetate-hexanes (25 mL) and allowed to stir for 1 h. The resulting precipitate was filtered and washed with 40% ethyl acetate-hexanes to afford Compound 2b as a white powder (1.58 g, 69%) (i.e., Example compound 4(a) in PCT International Patent Publication No. WO2001/089457 A2, herein incorporated by reference in its entirety).

Step 2:

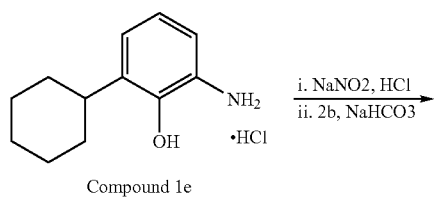

Compound 1e

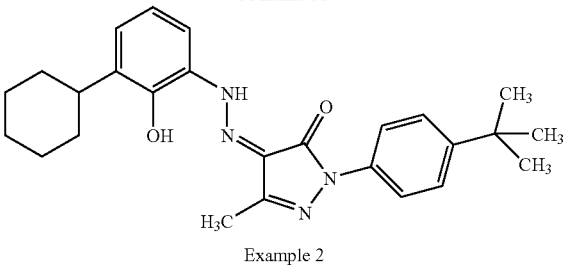

Example 2

A red solution of Compound 1e (0.18 g of the crude powder, 0.56 mmol), 1 M HCl (2 mL, 2.0 mmol) and ethanol (1.6 mL) was cooled to 0 deg C. under nitrogen. A solution of 0.066 g of sodium nitrite in 1 mL of water was prepared separately and 0.62 mL (0.59 mmol of sodium nitrite) was added dropwise to the solution containing compound 1e with formation of a dark red-yellow color. The diazotization was monitored using TLC with 10% ethyl acetate-hexanes. Compound 2b (0.13 g, 0.56 mmol) was added after 45 min followed by sodium bicarbonate (0.24 g, 2.9 mmol) and additional ethanol (1 mL). The mixture was allowed to warm to 20 deg C., treated with additional sodium bicarbonate (0.20 g, 2.4 mmol) to adjust the pH to 7-8, and allowed to stir for 12 h. The mixture was diluted with ethyl acetate (100 mL), washed with saturated sodium chloride (2×20 mL), and dried over sodium sulfate. The solvent was removed under reduced pressure and the residue purified by silica gel chromatography (10% ethyl acetate-hexanes) to afford Example 2 (0.16 g, 67%). Electrospray MS [M]– 431.2.

Example 3

Preparation of 3-(3'-{2-[1-(3,4-dimethylphenyl)-3-methyl-5-oxo-4,5-dihydro-1H-pyrazol-4-ylidene]hydrazino}-2'-hydroxy-phenyl)cyclohexane-1-carboxylic Acid Step 1:

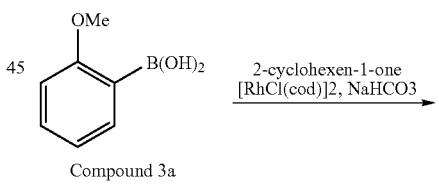

Compound 3a

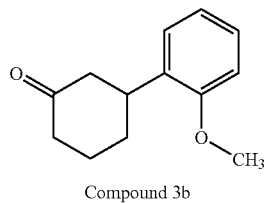

Compound 3b

Compound 3a (2-methoxybenzeneboronic acid, Acros catalog number 34466-0010) (2.36 g, 16.0 mmol), 1,5-cyclooctadienerhodium(I) chloride dimer (0.15 g, 0.31 mmol), and sodium bicarbonate (0.087 g, 1.0 mmol) were placed under argon, dissolved in dioxane-water 6:1 (35 mL), and allowed to stir for 10 min. 2-Cyclohexen-1-one (1.0 mL, 10.0 mmol) was added, and the mixture allowed to stir for 12 h. The solvents were removed under reduced pressure. The residue was diluted with ethyl acetate (150 mL), washed with 0.1

M HCl (2×20 mL), water (1×20 mL), and saturated sodium chloride (1×20 mL), and dried over sodium sulfate. The solvent was removed under reduced pressure and the residue purified by silica gel chromatography (gradient of 5 to 15% ethyl acetate-hexanes) to afford Compound 3b as a clear colorless oil (1.96 g, 62%). $^1$H NMR (400 MHz, DMSO-d6) δ 7.23 (1H, dd, J=7.6, 1.6 Hz), 7.20 (1H, dt, J=7.2, 2.0 Hz), 6.97 (1H, dd, J=8.0, 1.2 Hz), 6.93 dt, J=7.2, 1.2 Hz), 3.78 (3H, s), 3.29 (1H, m), 2.61-2.54 (1H, m), 2.47-2.38 (1H, m), 2.30-2.23 (2H, m), 2.05-1.99 (1H, m), 1.87-1.82 (2H, m), 1.69-1.64 (1H, m).

Step 2:

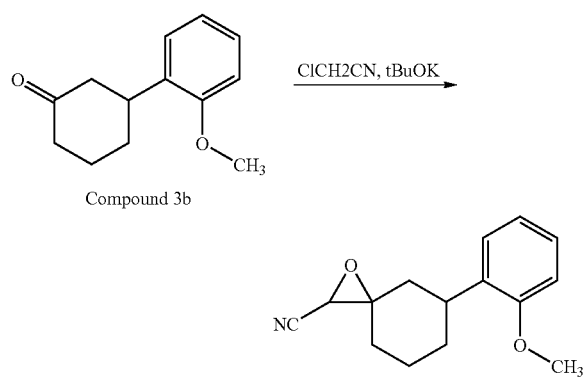

Compound 3b (0.22 g, 1.1 mmol), chloroacetonitrile (0.07 mL, 1.1 mmol), and 1 M potassium tert-butoxide in tert-butanol (1.1 mL, 1.1 mmol) were combined under nitrogen and allowed to stir 12 h. The brown residue was diluted with diethyl ether (10 mL) and filtered through a pad of silica gel, washing with an additional 75 mL of ether. The ether was removed under reduced pressure and the residue purified by silica gel chromatography (10% ethyl acetate-hexanes) to afford compound 3c as a clear oil (0.23 g, 88%) as a mixture of isomers. $^1$H NMR (400 MHz, DMSO-d6) δ 7.22-7.18 (2H, m), 6.98-6.90 (2H, m), 3.96-3.92 (1H, 2s), 3.78-3.76 (3H, m), 3.20-3.10 (1H, m), 2.26-1.75 (4H, m), 1.65-1.26 (4H, m).

Step 3:

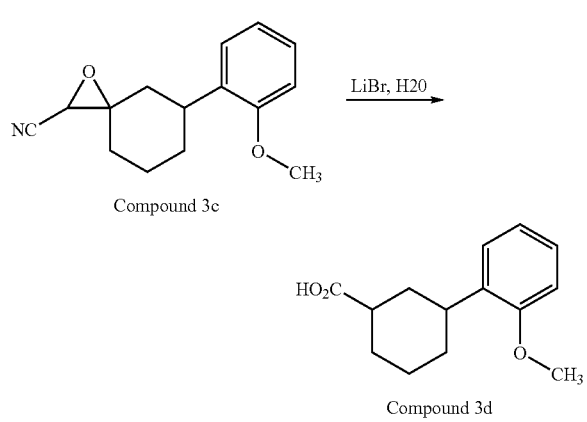

Compound 3c (0.23 g, 0.95 mmol) was then combined with lithium bromide (0.13 g, 1.45 mmol) and dissolved in acetonitrile (1 mL) and N,N-dimethylformamide (1 mL). Water (0.034 mL, 1.9 mmol) was added and the mixture was warmed to 90-91 deg C. for 24 h. The mixture was diluted with ethyl acetate (100 mL) and water (20 mL). The aqueous layer was acidified with 1 M HCl and extracted with diethyl ether (2×20 mL). The combined organics were washed with 0.1 M HCl (10 mL), saturated sodium chloride (3×10 mL), and dried over sodium sulfate. The solvents were removed under reduced pressure to afford Compound 3d as an amber oil which was used directly without further purification.

Step 4:

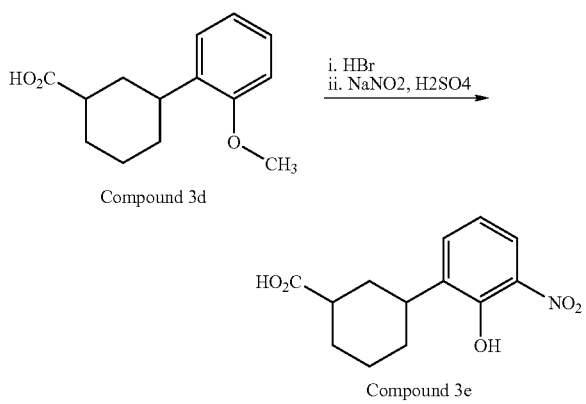

Compound 3d was dissolved in glacial acetic acid (1 mL) and 48% hydrobromic acid (1 mL) and heated to reflux for 3.5 h. The mixture was allowed to cool, and the bulk of solvents were removed under reduced pressure. The residue was dissolved in diethyl ether (100 mL), washed with water (1×10 mL) and saturated sodium chloride (2×10 mL) and dried over sodium sulfate. The mixture was concentrated under reduced pressure and filtered over a plug of silica gel using additional diethyl ether (50 mL) to wash the plug. The solvent was removed under reduced pressure. $^1$HNMR (400 MHz, DMSO-d6) δ 12.02 (1H, s), 9.24 (1H, br s), 7.07 (1H, dd, J=7.6, 1.6 Hz), 6.96 (1H, dd, J=7.2, 1.6 Hz), 6.78-6.71 (2H, m), 2.88 (1H, m), 2.35-2.31 (1H, m), 1.95-1.69 (4H, m), 1.45-1.28 (4H, m).

The product was then dissolved in diethyl ether (3 mL) and cooled to 0 deg C. Sodium nitrite (0.20 g, 2.9 mmol) and water (1 mL) were added and 2.4 N sulfuric acid (4 mL, 9.5 mmol) was added dropwise over 10 minutes with a bright yellow color formation. The mixture was allowed to stir 30 min at 0 deg C. and 1 hr at 20 deg C., and then diluted with 75 mL of ethyl acetate-hexanes 1:1. The organics were washed with saturated sodium chloride (3×10 mL) and dried over sodium sulfate. The solvent was removed under reduced pressure and the mixture of isomers was separated using silica gel chromatography with a gradient of 30 to 40% ethyl acetate-hexanes as eluant. The ortho isomer Compound 3e was collected as a yellow oil (0.057 g, 23% yield over two steps). $^1$H NMR (400 MHz, DMSO-d6) δ 12.08 (1H, br s), 10.55 (1H, s), 7.86 (1H, dd, J=8.4, 1.6 Hz), 7.60 (1H, dd, J=7.6, 1.6 Hz), 7.01 (1H, t, J=7.6 Hz), 3.05 (1H, m), 2.39 (1H, m), 1.99-1.77 (4H, m), 1.48-1.32 (4H, m).

Step 5:

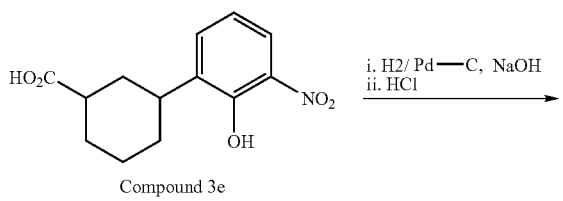

-continued

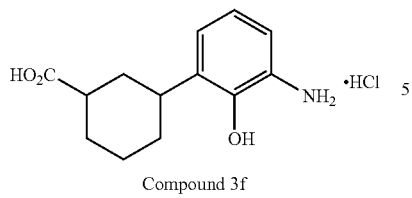

Compound 3f

To compound 3e (0.054 g, 0.20 mmol) and 10% palladium on carbon (0.03 g) were added ethanol (2 mL), water (1 mL), and 3 N sodium hydroxide (0.14 mL, 0.42 mmol). The mixture was degassed briefly under reduced pressure and allowed to stir under hydrogen at 1 atm at 20 deg C. for 1.5 hr. The catalyst was removed by filtration. The red solution was treated with 1 mL of 1 M HCl, and the solvent removed under reduced pressure. The resulting red powder, Compound 3f, was used directly without further purification.

Step 6:

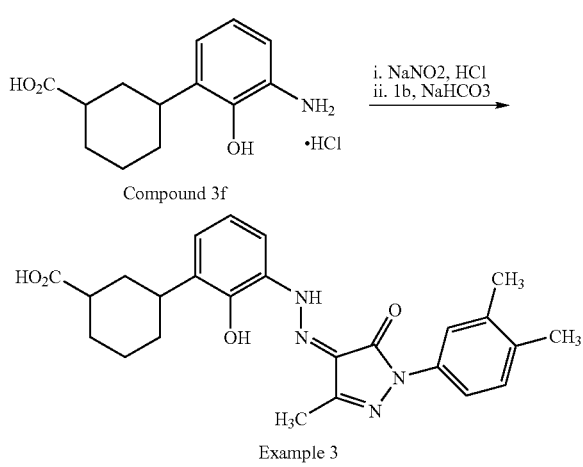

Example 3

A red solution of Compound 3f, 1 M HCl (0.75 mL, 0.75 mmol) and ethanol (1.5 mL) was cooled to 0 deg C. under nitrogen. A solution of 0.060 g of sodium nitrite in 1 mL of water was prepared separately and 0.25 mL (0.22 mmol of sodium nitrite) was added dropwise to the solution containing compound 3f with formation of a dark red-yellow color. The diazotization was monitored using TLC with 75% ethyl acetate-hexanes. Compound 1b (0.042 g, 0.21 mmol) was added after 30 min followed by sodium bicarbonate (0.086 g, 1.0 mmol) and additional ethanol (0.3 mL). The mixture was allowed to warm to 20 deg C., treated with additional sodium bicarbonate (0.073 g, 0.87 mmol) to adjust the pH to 7-8, and allowed to stir for 12 h. The mixture was diluted with ethyl acetate (100 mL) and 0.1 M HCl (5 mL). The aqueous layer was separated and extracted with 20 mL of ethyl acetate. The combined organics were washed with saturated sodium chloride (2×20 mL), and dried over sodium sulfate. The solvent was removed under reduced pressure and the residue purified by silica gel chromatography (40% ethyl acetate-hexanes) to afford Example 3 (0.0256 g, 29% yield over 2 steps). Electrospray MS [M]− 447.2. Example 3 was found to have solubility in water of 140 micromolar as the parent compound without salt formation or use of specialized excipients.

Example 4

Preparation of 3-(3'-{2-[1-(4-tert-butylphenyl)-3-methyl-5-oxo-4,5-dihydro-1H-pyrazol-4-ylidene]hydrazino}-2'-hydroxy-phenyl)cyclohexane-1-carboxylic Acid Step 1:

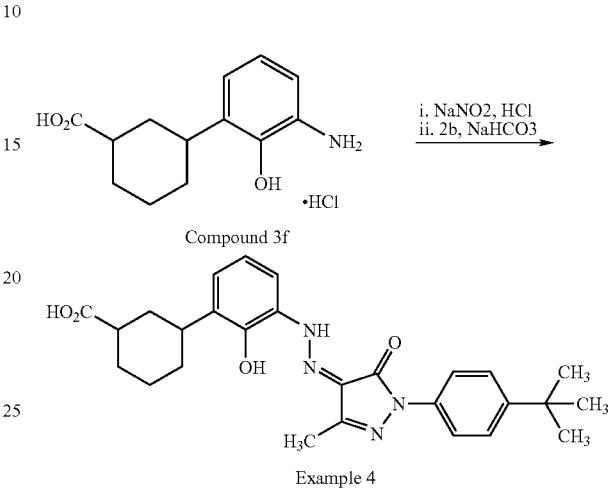

Example 4

Example 4 was prepared using a procedure similar to the procedure of Example 3, except that Compound 2b was used in place of Compound 1b in Step 6 (37% yield). Electrospray MS [M+H]+ 477.3.

Example 5

Preparation of 3-(3'-{2-[1-(3,4-dimethylphenyl)-3-methyl-5-oxo-4,5-dihydro-1H-pyrazol-4-ylidene]hydrazino}-2'-hydroxy-phenyl)cyclohexane-1-carboxylic Acid ethyl ester Step 1:

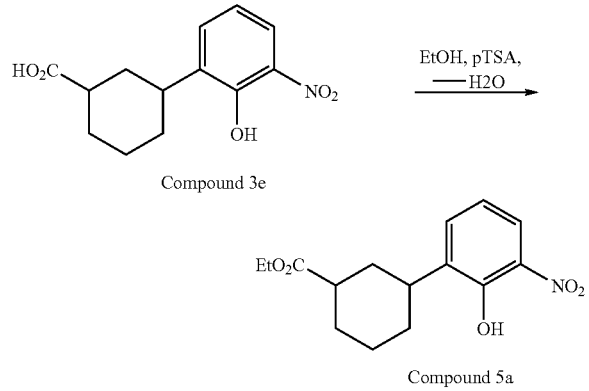

Compound 5a

A solution of Compound 3e (0.15 g, 0.57 mmol), ethanol (0.1 mL, 1.7 mmol), and p-toluenesulfonic acid (0.001 g, 0.0057 mmol) in toluene (15 mL) was heated to reflux with azeotropic removal of water using a Dean-Stark apparatus. After 1 h, 10 mL of toluene and 0.5 mL of ethanol (8.6 mmol)

were added and the heating continued for 3 h. The mixture was cooled, diluted with diethyl ether (100 mL), washed with saturated sodium chloride (3×10 mL), and dried over sodium sulfate. The solvent was removed under reduced pressure and purified by silica gel chromatography (10% ethyl acetate-hexanes) to afford Compound 5a as a yellow oil (0.10 g, 62%). $^1$H NMR (400 MHz, DMSO-d6) δ 10.55 (1H, s), 7.86 (1H, dd, J=8.4, 1.6 Hz), 7.60 (1H, dd, J=8.0, 2.0 Hz), 7.01 (1H, t, J=7.66 Hz), 4.04 (2H, q, J=7.2 Hz), 3.10-3.04 (1H, m), 2.00-1.74 (5H, m), 1.51-1.33 (4H, m).

Step 2:

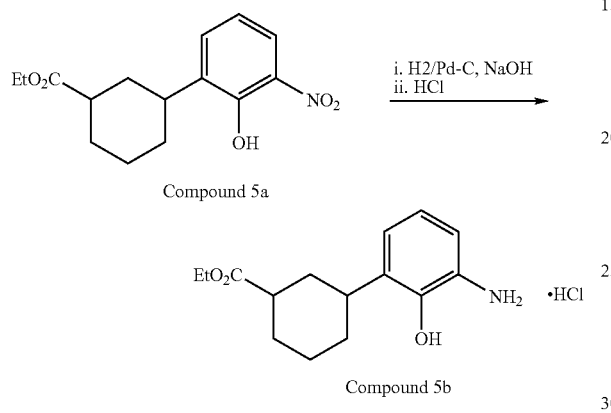

A mixture of compound 5a (0.10 g, 0.34 mmol) and 10% palladium on carbon (0.05 g) was purged with nitrogen and ethanol (4 mL) was added. The mixture was degassed briefly under reduced pressure and allowed to stir under hydrogen at 1 atm at 20 deg C. for 1.5 hr. The catalyst was removed by filtration. The light red solution was treated with 0.5 mL of 1 M HCl, and the solvent removed under reduced pressure. The resulting light red oil, Compound 5b (0.1 g, 100% yield), was used directly without further purification.

Step 3:

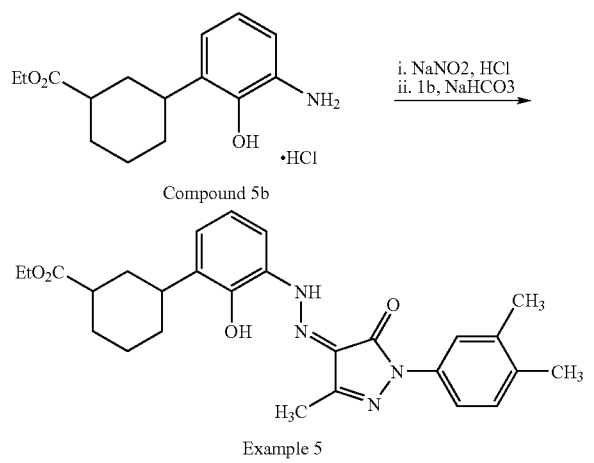

Example 5 was prepared using a procedure similar to the procedure of Example 3, except that Compound 5b was used in place of Compound 3f in Step 6 (77% yield). Electrospray MS [M+H]+ 477.3.

Example 6

Preparation of 1-(3,4-dimethylphenyl)-4-{2-[2-hydroxy-3-(1-methylpiperidin-4-yl)phenyl]hydrazin-1-ylidene}-3-methyl-4,5-dihydro-1H-pyrazol-5-one Step 1:

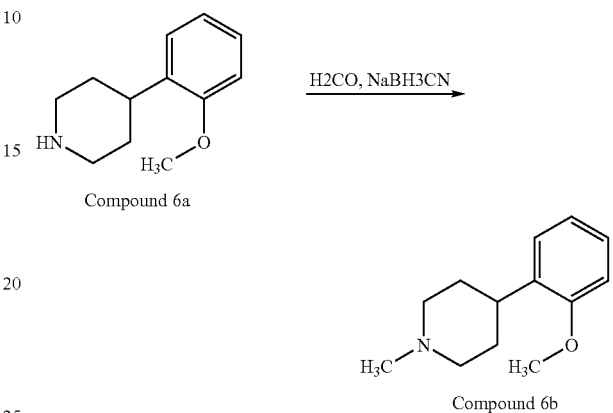

Compound 6a (4-(2-methoxyphenyl)piperidine, Maybridge catalog number BTB13447) (0.30 g, 1.6 mmol) and glacial acetic acid (0.45 mL, 7.9 mmol) were dissolved in methanol (8 mL) and cooled to 0 deg C. Sodium cyanoborohydride (0.20 g, 3.1 mmol) was added and then 38% aqueous formaldehyde (0.34 mL, 4.7 mmol). The mixture was allowed to stir for 15 min at 0 deg C. and 12 h at 20 deg C. The solvent was removed under reduced pressure, diethyl ether was added (100 mL) and saturated sodium bicarbonate (10 mL). The bicarbonate was washed with 20 mL of ether and the combined organics were washed with saturated sodium chloride (3×10 mL) and dried over sodium sulfate. The solvent was removed under reduced pressure to afford Compound 6b as a colorless oil (0.28 g, 88% yield). $^1$H NMR (400 MHz, DMSO-d6) δ 7.18-7.14 (2H, m), 6.95-6.87 (2H, m), 3.77 (3H, s), 2.85-2.80 (3H, m), 2.17 (3H, s), 1.97-1.90 (2H, m), 1.65-1.59 (4H, m).

Step 2:

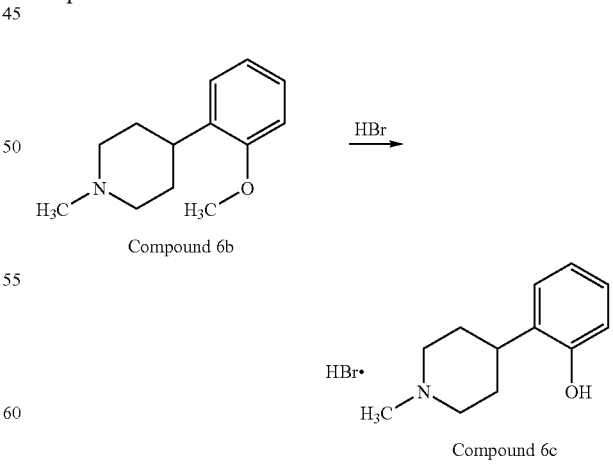

Compound 6b (0.28 g, 1.4 mmol) was dissolved in glacial acetic acid (2.5 mL) and 48% hydrobromic acid (2.5 mL) and heated to reflux for 7.5 h. The mixture was allowed to cool, and the bulk of solvents were removed under reduced pressure. The product compound 6c was used directly without further purification. ¹H NMR (400 MHz, DMSO-d6) δ 9.50 (1H, s), 9.33 (1H, br s), 7.06-7.02 (2H, m), 6.83-6.75 (2H, m), 3.50-3.48 (3H, m), 3.13-3.02 (2H, m), 2.89-2.79 (3H, m), 1.92-1.87 (4H, m).

Step 3:

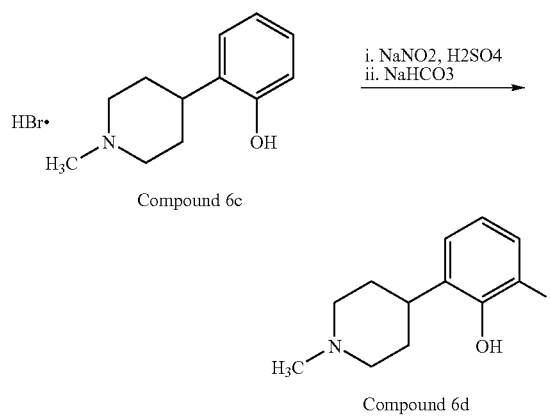

Compound 6c was dissolved in glacial acetic acid (6 mL) and 98% sulfuric acid (1.37 g). The solution was cooled to 5 deg C. in an ice bath and sodium nitrite (0.19 g, 2.7 mmol) was added in four portions over 10 min. The mixture was allowed to stir 15 min at 5 deg C. and 2 h at 20 deg C. The mixture was then concentrated under reduced pressure. Diethyl ether (3×10 mL) was added, the mixture stirred, and then decanted, resulting in a viscous residue. The mixture was dissolved in water (15 mL), cooled to 0 deg C., and then treated with saturated sodium bicarbonate dropwise to adjust the pH to 7-8. The precipitate was removed by filtration, and the solvent was removed under reduced pressure. Anhydrous ethanol (20 mL) was added to the residue and the precipitate of salts was removed by filtration. The solvent was removed under reduced pressure to afford compound 6d as an oily residue (0.2 g, 62% yield).

Step 4:

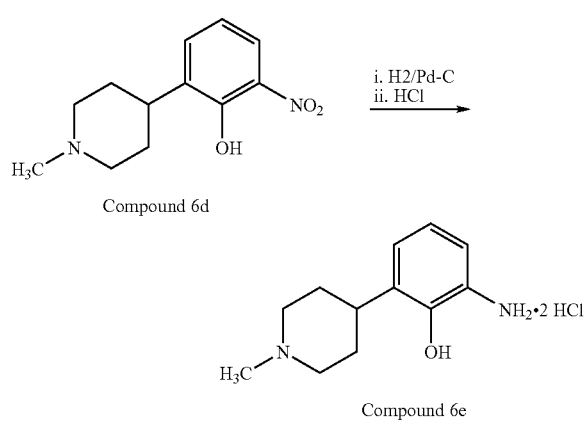

A mixture of compound 6d (0.20 g, 0.85 mmol) and 10% palladium on carbon (0.05 g) was purged with nitrogen and ethanol (4 mL) and water (0.5 mL) were added. The mixture was degassed briefly under reduced pressure and allowed to stir under hydrogen at 1 atm at 20 deg C. for 1.5 hr. The catalyst was removed by filtration. The light red solution was treated with 0.5 mL of 1 M HCl, and the solvent removed under reduced pressure. The resulting residue, Compound 6e was used directly without further purification.

Step 5:

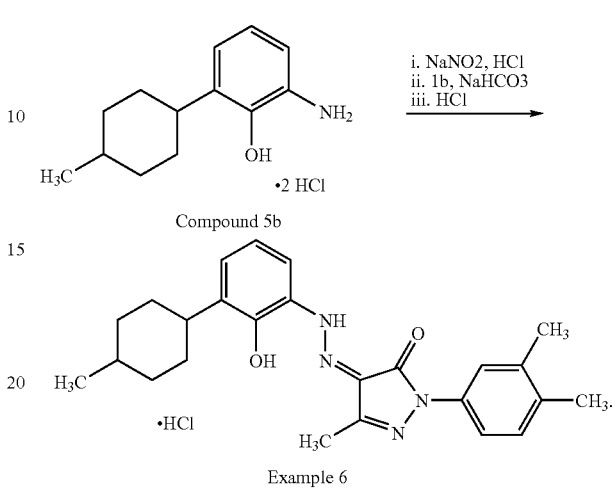

A solution of Compound 6e, 1 M HCl (1.2 mL, 1.2 mmol) and ethanol (0.5 mL) was cooled to 0 deg C. under nitrogen. A solution of 0.026 g of sodium nitrite in 1 mL of water was prepared separately and 0.27 mL (0.38 mmol of sodium nitrite) was added dropwise to the solution containing compound 3f. The diazotization was monitored using TLC (chloroform-methanol-acetic acid 6:3:1). Compound 1b (0.071 g, 0.35 mmol) was added after 30 min followed by sodium bicarbonate (0.15 g, 1.8 mmol). The mixture was allowed to warm to 20 deg C., treated with additional sodium bicarbonate (0.13 g, 1.6 mmol) to adjust the pH to 7-8, and allowed to stir for 12 h. The mixture was diluted with ethyl acetate (100 mL) and washed with water (2×10 mL) and saturated sodium chloride (2×20 mL), and dried over sodium sulfate. The solvent was removed under reduced pressure and the residue purified by silica gel chromatography (a gradient of 10 to 20% ethanol-methylene chloride) to afford Example 6 (0.025 g, 6% yield over 2 steps). Electrospray MS [M+H]+ 420.3.

Example 7

Proliferation Assay

Some of the compounds of the invention were active in an in vitro proliferation assay using highly purified primary CD34+ progenitor cells isolated from human bone marrow (Stem Cell Technologies; Catalog #ABM016F). The purity of the CD34+ cells was greater than 90% by flow cytometric analysis (Stem Cell Technologies). CD34+ cells were cultured in flat-bottomed 96-well plates (CELLSTAR, Greiner Bio-One, catalog #655083) at the density of 1000 cells/well in the presence or absence of TPO mimetics. The plates were incubated in a humidified atmosphere at 37° C., 5% CO2, in a volume of 100 uL per well in StemSpan® SFEM medium (Stem Cell Technologies; Cat #09600) supplemented with 100 U/ml of penicillin and 100 ug/ml of streptomycin (Sigma, Catalog #P0781). After an incubation period of 10 days, 100 ul of CellTiter-Glo® reagent solution (Promega, Madison, Wis.) was added to the wells followed by delicate shaking for two minutes, and the plates were then allowed to stand in RT for an additional 20 min. Total volume of the cultures after addition of CellTiter-Glo® reagent solution was 200 ul.

Luminescence was read using a Victor3 (Perkin Elmer, Waltham, Mass.) multilabel plate reader in RT. The compounds of Examples 3 and 4 in this invention had proliferative activity at less than or equal to 1 micromolar concentration in the CD34+ assay with a stimulation index of higher than 15 at a concentration of 0.625 micromolar.

Example 8

Pharmaceutical Composition Examples

The following are representative pharmaceutical formulations containing a compound of Formula I.

Tablet Formulation

The following ingredients are mixed intimately and pressed into single scored tablets:

| Ingredient | Quantity per tablet (mg) |
| --- | --- |
| Compound described herein | 400 |
| Cornstarch | 50 |
| Croscarmellose sodium | 25 |
| Lactose | 120 |
| Magnesium stearate | 5 |

Capsule Formulation

The following ingredients are mixed intimately and loaded into a hard-shell gelatin capsule:

| Ingredient | Quantity per tablet (mg) |
| --- | --- |
| Compound described herein | 200 |
| Lactose | 148 |
| Spray-dried magnesium stearate | 2 |

Suspension Formulation

The following ingredients are mixed to form a suspension for oral administration:

| Ingredient | Amount |
| --- | --- |
| Compound described herein | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

Injectable Formulation

The following ingredients are mixed to form an injectable formulation:

| Ingredient | Amount |
| --- | --- |
| Compound described herein | 1.2 g |
| Sodium acetate buffer solution | 2.0 mL of 0.4 M |
| HCl (1 N) or NaOH (1 M) | q.s. to suitable pH |
| Water (distilled, sterile) | q.s. to 20 mL |

All of the above ingredients, except water, are combined and heated to 60-70° C. with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Quantity per tablet (mg) |
| --- | --- |
| Compound described herein | 500 |
| Witepsol ® H-15 | balance |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

What is claimed is:

1. A compound having a structure according to the following formula

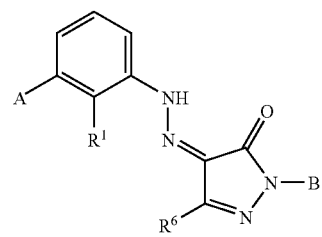

wherein
A is substituted or unsubstituted cycloalkyl or substituted or unsubstituted heterocycloalkyl, wherein said cycloalkyl is monocyclic
$R^1$ is a member selected from hydroxy, alkoxy, and carboxy,
$R^6$ is hydrogen or substituted or unsubstituted alkyl, and
B is a member selected from substituted or unsubstituted cycloalkyl, substituted or unsubstituted heterocycloalkyl, substituted or unsubstituted aryl, and substituted or unsubstituted heteroaryl.

2. The compound according to claim 1, wherein $R^1$ is OH or $OR^{1a}$, wherein $R^{1a}$ is a negative charge or a salt counterion.

3. The compound according to claim 1, wherein $R^6$ is a member selected from substituted or unsubstituted alkyl.

4. The compound according to claim 1, wherein $R^6$ is a member selected from substituted or unsubstituted methyl, substituted or unsubstituted ethyl, substituted or unsubstituted propyl, substituted or unsubstituted butyl, and substituted or unsubstituted pentyl.

5. The compound according to claim 1, wherein A is a member selected from substituted or unsubstituted cyclopropyl, substituted or unsubstituted cyclobutyl, substituted or unsubstituted cyclopentyl, substituted or unsubstituted cyclohexyl, substituted or unsubstituted piperidinyl, substituted or unsubstituted 1,2,3,6-tetrahydropyridinyl, substituted or unsubstituted pyrrolidinyl, substituted or unsubstituted 1-oxo-phosphinanyl, and substituted or unsubstituted 1,1 dioxo-tetrahydrothiopyranyl.

6. The compound according to claim 1, wherein A is a member selected from substituted cyclopentyl, substituted cyclohexyl, substituted piperidinyl, substituted 1,2,3,6-tetrahydropyridinyl, substituted pyrrolidinyl, substituted 1-oxo-phosphinanyl, and substituted 1,1 dioxotetrahydrothiopyranyl.

7. The compound according to claim 6, wherein A is substituted with a moiety which is a member selected from hydroxyl, substituted or unsubstituted cyclopropyl, substituted or unsubstituted alkyl,

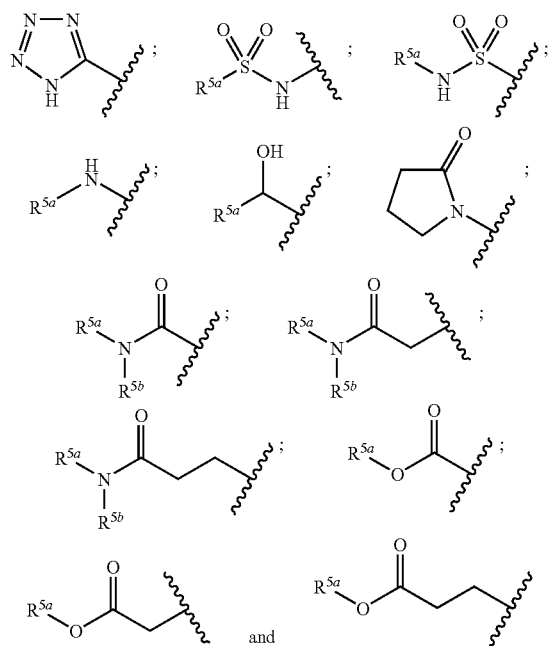

wherein each $R^{5a}$ and $R^{5b}$ is a member independently selected from H, substituted or unsubstituted alkyl and substituted or unsubstituted heteroalkyl, or $R^{5a}$ and $R^{5b}$ together with the nitrogen atom to which they are attached are heterocycloalkyl.

8. The compound according to claim 6, wherein A is substituted with a moiety which is a member selected from hydroxyl, unsubstituted cyclopropyl, substituted or unsubstituted alkyl,

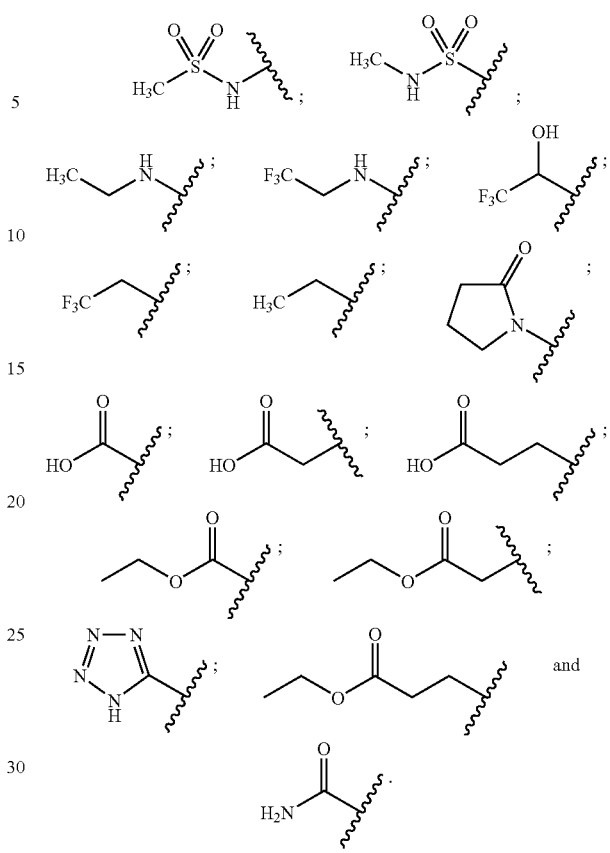

9. The compound according to claim 1, wherein A is cyclohexyl or cyclopentyl which is substituted with one to three groups selected from the group consisting of: alkyl, alkenyl, alkynyl, alkoxy, acyl, alkylcarbonylamino, carboxy, carboxyalkyl, alkoxycarbonyl, alkoxycarbonylalkyl, cyano, nitro, alkylthio, halo, haloalkyl, haloalkoxy, amino, alkylamino, dialkylamino, aminocarbonyl, alkylaminocarbonyl, dialkylaminocarbonyl, hydroxy, hydroxyalkyl, hydroxyalkyloxy, hydroxyalkyloxyalkyl, alkoxyalkyloxyalkyl, aryl, heteroaryl, cycloalkyl, cycloalkyloxy, heteroaralkyloxy, aminoalkyl, aminoalkyloxy, alkoxyalkyl, alkoxyalkyloxy, haloalkoxyalkyl, aryloxyalkyl, heteroaryloxyalkyl, heterocycloalkyloxyalkyl, heterocycloalkylalkyl, heterocycloalkylalkyloxy, heterocycloalkyloxy, -alkylene-S(O)$_n$—R$_m$ (where n is 0 to 2 and R$_m$ is alkyl, haloalkyl, hydroxyalkyl, alkoxyalkyl, aryl, heteroaryl, or heteroaralkyl), -alkylene-NHSO$_2$—R$_w$ (where R$_w$ is alkyl, haloalkyl, aryl, heteroaryl, or heteroaralkyl), -alkylene-NHC(O)—R$_q$ (where R$_q$ is alkyl, halo alkyl, aryl, heteroaryl, or heteroaralkyl), and -(methylene)$_{n1}$-C(O)NR$_f$R$_g$ (where n1 is 0 or 1, R$_f$ is hydrogen, alkyl, or hydroxyalkyl and R$_g$ is hydrogen, alkyl, hydroxyalkyl, alkoxyalkyl, aryl, heteroaryl, heteroaralkyl, or heterocycloalkylalkyl, or R$_f$ and R$_g$ together with the nitrogen atom to which they are attached from heterocycloalkyl), and -(alkylene)$_{1-3}$-SiR$_{1-3}$ (where R is alkyl).

10. The compound according to claim 1, wherein A is cyclohexyl substituted with carboxy, ethoxycarbonyl, trifluoroethanol, tetrazole, or alkylsulfonamide.

11. The compound according to claim 1, wherein A is cyclohexyl substituted with carboxy.

12. The compound according to claim 1, wherein A is heterocycloalkyl which is substituted with one to three, preferably one, group(s) selected from the group consisting of: alkyl, alkenyl, alkynyl, alkoxy, acyl, alkylcarbonylamino, carboxy, carboxyalkyl, alkoxycarbonyl, alkoxycarbonylalkyl, cyano, nitro, alkylthio, halo, haloalkyl, haloalkoxy, amino, alkylamino, dialkylamino, aminocarbonyl, alkylaminocarbonyl, dialkylaminocarbonyl, hydroxy, oxo, hydroxyalkyl, hydroxyalkyloxy, hydroxyalkyloxyalkyl, alkoxyalkyloxyalkyl, aryl, heteroaryl, cycloalkyl, cycloalkyloxy, heteroaralkyloxy, aminoalkyl, aminoalkyloxy, alkoxyalkyl, alkoxyalkyloxy, haloalkoxyalkyl, aryloxyalkyl, heteroaryloxyalkyl, heterocycloalkyloxyalkyl, heterocycloalkylalkyl, heterocycloalkylalkyloxy, heterocycloalkyloxy, -alkylene-S$(O)_n$—$R_m$ (where n is 0 to 2 and $R_m$ is alkyl, haloalkyl, hydroxyalkyl, alkoxyalkyl, aryl, heteroaryl, or heteroaralkyl), -alkylene-$NHSO_2$—$R_w$ (where $R_w$ is alkyl, haloalkyl, aryl, heteroaryl, or heteroaralkyl), -alkylene-NHC(O)—$R_q$ (where $R_q$ is alkyl, halo alkyl, aryl, heteroaryl, or heteroaralkyl), and -(methylene)$_{n1}$-C(O)$NR_fR_g$ (where nl is 0 or 1, $R_f$ is hydrogen, alkyl, or hydroxyalkyl and $R_g$ is hydrogen, alkyl, hydroxyalkyl, alkoxyalkyl, aryl, heteroaryl, heteroaralkyl, or heterocycloalkylalkyl, or $R_f$ and $R_g$ together with the nitrogen atom to which they are attached from heterocycloalkyl), and -(alkylene)$_{1-3}$-$SiR_{1-3}$ (where R is alkyl).

13. The compound according to claim 1, wherein A is piperidino substituted with carboxymethyl, ethoxycarbonylmethyl, cyclopropyl, or 2,2,2-trifluoroethyl.

14. The compound according to claim 1, wherein A is piperidino substituted with carboxymethyl.

15. The compound according to claim 1, wherein B is a member selected from substituted or unsubstituted aryl, substituted or unsubstituted heteroaryl, substituted or unsubstituted cycloalkyl, and substituted or unsubstituted heterocycloalkyl.

16. The compound according to claim 15, wherein B is a member selected from substituted or unsubstituted phenyl, substituted or unsubstituted cyclohexyl, substituted or unsubstituted pyridinyl, substituted or unsubstituted azetidinyl, substituted or unsubstituted piperidinyl, substituted or unsubstituted 1,2,3,6-tetrahydropyridinyl, substituted or unsubstituted pyrrolidinyl, substituted or unsubstituted 1-oxo-phosphinanyl, substituted or unsubstituted 1,1-dioxotetrahydrothiopyranyl, substituted or unsubstituted tetrahydropyranyl, substituted or unsubstituted thiophenyl, substituted or unsubstituted cyclopentyl, substituted or unsubstituted cycloheptenyl, and substituted or unsubstituted cycloheptyl.

17. The compound according to claim 15, wherein B is a member selected from unsubstituted 2-thiophenyl, unsubstituted 3-thiophenyl, unsubstituted pyridinyl, unsubstituted pyranyl, unsubstituted cyclopentyl, unsubstituted cyclohexyl, and unsubstituted cycloheptyl.

18. The compound according to claim 15, wherein B is member selected from substituted phenyl, substituted pyridinyl, substituted azetidinyl, substituted piperidinyl, substituted 1,2,3,6-tetrahydropyridinyl, substituted pyrrolidinyl, substituted 1-oxo-phosphinanyl, substituted 1,1-dioxotetrahydrothiopyranyl, substituted tetrahydropyranyl, substituted cyclopentyl, substituted cyclohexyl, and substituted cycloheptyl.

19. The compound according to claim 1, wherein B is monosubstituted with a moiety which is a member selected from hydroxyl, substituted or unsubstituted alkyl, substituted or unsubstituted dialkylamino, halogen, substituted or unsubstituted cycloalkyl, and substituted or unsubstituted alkyloxy,

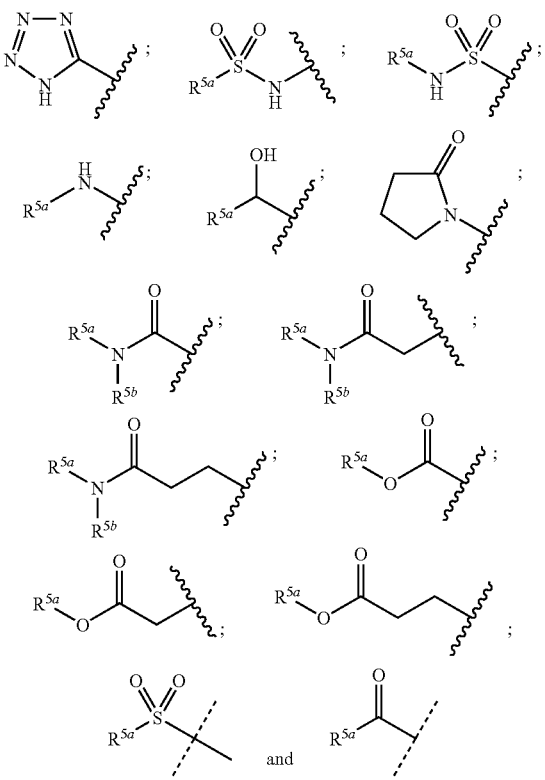

wherein each $R^{5a}$ and $R^{5b}$ is a member independently selected from H, substituted or unsubstituted alkyl, substituted or unsubstituted cycloalkyl, and substituted or unsubstituted heteroalkyl, or $R^{5a}$ and $R^{5b}$ together with the nitrogen atom to which they are attached from heterocycloalkyl.

20. The compound according to claim 1, wherein B is disubstituted with moieties which are members independently selected from hydroxyl, substituted or unsubstituted alkyl, substituted or unsubstituted dialkylamino, halogen, substituted or unsubstituted cycloalkyl, substituted or unsubstituted alkyloxy,

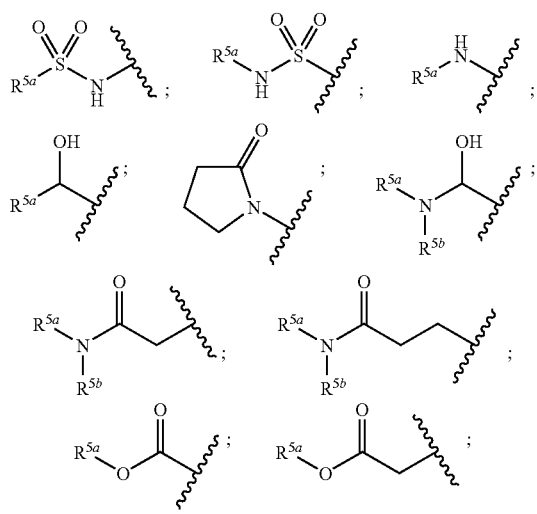

-continued

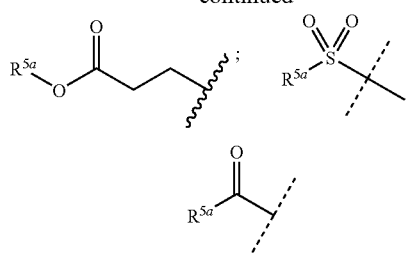

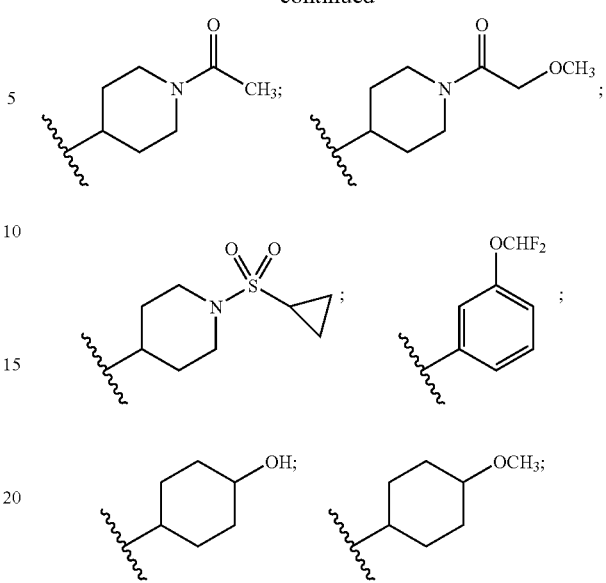

wherein each $R^{5a}$ and $R^{5b}$ is a member independently selected from H, substituted or unsubstituted alkyl and substituted or unsubstituted heteroalkyl, or $R^{5a}$ and $R^{5b}$ together with the nitrogen atom to which they are attached are heterocycloalkyl.

21. The compound according to claim 1, wherein B is a phenyl which is disubstituted with moieties which are members independently selected from substituted or unsubstituted alkyl and halogen.

22. The compound according to claim 1, wherein B is a member selected from

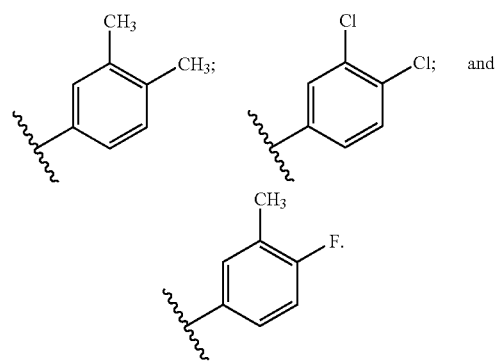

23. The compound according to claim 1, wherein B is a member selected from

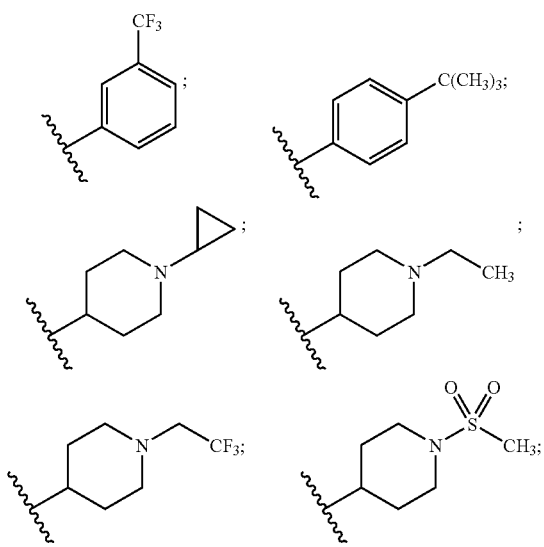

24. The compound according to claim 1, having a structure according to the formula:

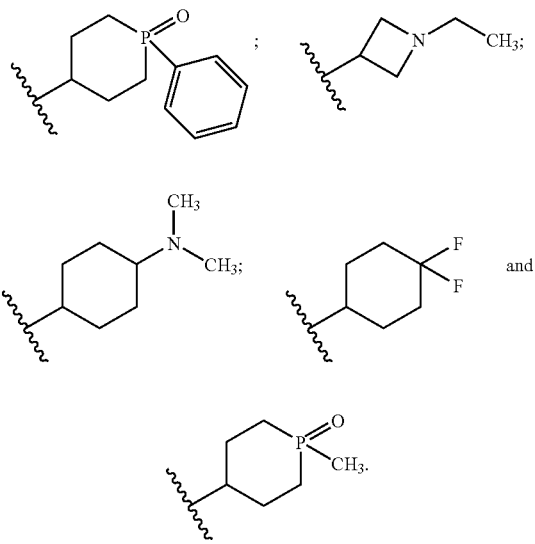

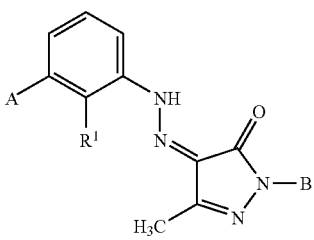

wherein

A is substituted or unsubstituted cycloalkyl or substituted or unsubstituted heterocycloalkyl; and $R^1$ is OH or $OR^{1a}$, wherein $R^{1a}$ is a negative charge or a salt counterion.

25. The compound according to claim 24, wherein A is a member selected from unsubstituted cyclohexyl,

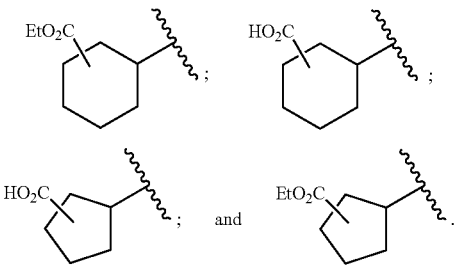

26. The compound according to claim 24, wherein A is a member selected from

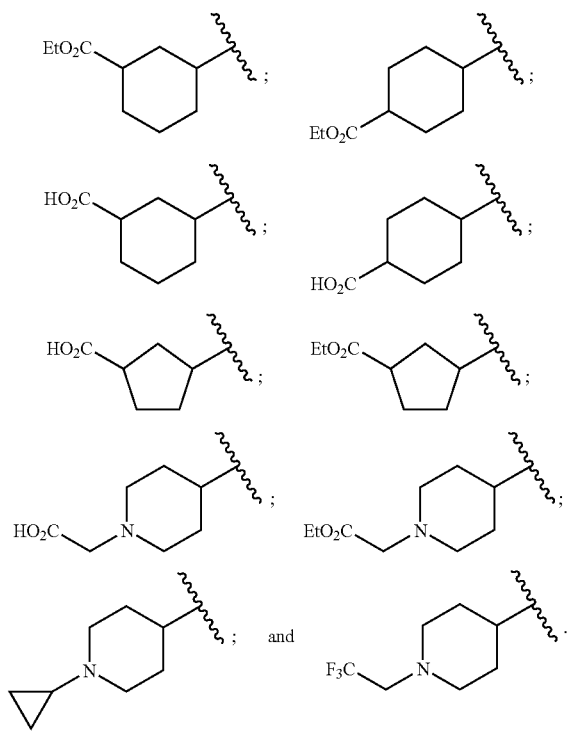

27. The compound according to claim 24, wherein B is a member selected from substituted and unsubstituted phenyl.

28. The compound according to claim 24, wherein B is a substituted phenyl.

29. The compound according to claim 24, wherein B is a member selected from

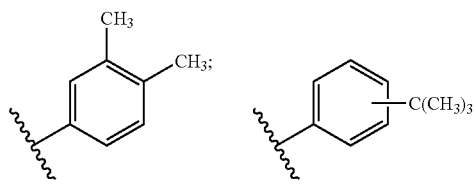

-continued

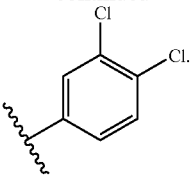

30. A pharmaceutical composition comprising: at least one compound of claim 1, and at least one pharmaceutically acceptable excipient.

31. A pharmaceutical composition comprising: at least one compound of claim 1, at least one corticosteroid, and at least one pharmaceutically acceptable excipient.

32. A pharmaceutical composition comprising: at least one compound of claim 1, at least one hematopoietic growth factor, and at least one pharmaceutically acceptable excipient.

33. A method of treating a physiological disorder, syndrome, or disease responsive to a TPO mimetic comprising:
administering to an animal in need thereof an effective amount of a least one compound of claim 1 or a pharmaceutically acceptable salt and/or solvate thereof,
wherein the physiological disorder, symptom, or disease is thrombocytopenia resulting from causative factors selected from the group consisting of immune thrombocytopenic purpura, cancer chemotherapy, surgery, rheumatoid arthritis, systemic lupus erythematosus, severe bacterial infections, liver transplantation, bone marrow transplantation, stem cell transplantation, medication causing thrombocytopenia, radiation injury or treatment, hepatitis C
viral infection, human immunodeficiency virus infection, and blood loss or withdrawal.

34. The compound, or pharmaceutically acceptable salts, solvates and/or esters thereof, selected from the group consisting of:
2-(3'-{2-[1-(3,4-dimethylphenyl)-3-methyl-5-oxo-4,5-dihydro-1H-pyrazol-4-ylidene]hydrazino}-2'-hydroxyphenyl)cyclohexane-1-carboxylic acid;
4-(3'-{2-[1-(3,4-dimethylphenyl)-3-methyl-5-oxo-4,5-dihydro-1H-pyrazol-4-ylidene]hydrazino}-2'-hydroxyphenyl)cyclohexane-1-carboxylic acid;
2-(3'-{2-[1-(3,4-dimethylphenyl)-3-methyl-5-oxo-4,5-dihydro-1H-pyrazol-4-ylidene]hydrazino}-2'-hydroxyphenyl)cyclopentane-1-carboxylic acid;
3-(3'-{2-[1-(3,4-dimethylphenyl)-3-methyl-5-oxo-4,5-dihydro-1H-pyrazol-4-ylidene]hydrazino}-2'-hydroxyphenyl)cyclopentane-1-carboxylic acid;
3-(3'-{2-[1-(3,4-dimethylphenyl)-3-methyl-5-oxo-4,5-dihydro-1H-pyrazol-4-ylidene]hydrazino}-2'-hydroxyphenyl)cycloheptane-1-carboxylic acid;
1-(3,4-dimethylphenyl)-4-(2-{2-hydroxy-3-[3-(2,2,2-trifluoro-1-hydroxyethyl)cyclohexyl]phenyl}hydrazin-1-ylidene)-3-methyl-4,5-dihydro-1H-pyrazol-5-one;
N-[4-(3-{2-[1-(3,4-dimethylphenyl)-3-methyl-5-oxo-4,5-dihydro-1H-pyrazol-4-ylidene]hydrazin-1-yl}-2-hydroxyphenyl)cyclohexyl]methanesulfonamide;
4-(3-{2-[1-(3,4-dimethylphenyl)-3-methyl-5-oxo-4,5-dihydro-1H-pyrazol-4-ylidene]hydrazin-1-yl}-2-hydroxyphenyl)-N-methylcyclohexane-1-sulfonamide;
1-(3,4-dimethylphenyl)-4-[2-(2-hydroxy-3-{3-[(2,2,2-trifluoroethyl)amino]cyclohexyl}phenyl)hydrazin-1-ylidene]-3-methyl-4,5-dihydro-1H-pyrazol-5-one; and 4-{2-[3-(1-cyclopropylpiperidin-4-yl)-2-hydroxyphenyl]hydrazin-1-ylidene}-1-(3,4-dimethylphenyl)-3-methyl-4,5-dihydro-1H-pyrazol-5-one.

35. A pharmaceutical composition comprising: at least one compound of claim 34, and at least one pharmaceutically acceptable excipient.

36. A pharmaceutical composition comprising: at least one compound of claim 34, at least one corticosteroid, and at least one pharmaceutically acceptable excipient.

37. A pharmaceutical composition comprising: at least one compound of claim 34, at least one hematopoietic growth factor, and at least one pharmaceutically acceptable excipient.

38. A method of treating a physiological disorder, syndrome, or disease responsive to a TPO mimetic comprising:
    administering to an animal in need thereof an effective amount of a least one compound of claim 34 or a pharmaceutically acceptable salt and/or solvate thereof,
    wherein the physiological disorder, symptom, or disease is thrombocytopenia resulting from causative factors selected from the group consisting of immune thrombocytopenic purpura, cancer chemotherapy, surgery, rheumatoid arthritis, systemic lupus erythematosus, severe bacterial infections, liver transplantation, bone marrow transplantation, stem cell transplantation, medication causing thrombocytopenia, radiation injury or treatment, hepatitis C viral infection, human immunodeficiency virus infection, myelodysplastic syndrome, and blood loss or withdrawal.

39. The compound according to claim 1, wherein A is heterocycloalkyl which is substituted with one group selected from the group consisting of:
    alkyl, alkenyl, alkynyl, alkoxy, acyl, alkylcarbonylamino, carboxy, carboxyalkyl, alkoxycarbonyl, alkoxycarbonylalkyl, cyano, nitro, alkylthio, halo, haloalkyl, haloalkoxy, amino, alkylamino, dialkylamino, aminocarbonyl, alkylaminocarbonyl, dialkylaminocarbonyl, hydroxy, oxo, hydroxyalkyl, hydroxyalkyloxy, hydroxyalkyloxyalkyl, alkoxyalkyloxyalkyl, aryl, heteroaryl, cycloalkyl, cycloalkyloxy, heteroaralkyloxy, aminoalkyl, aminoalkyloxy, alkoxyalkyl, alkoxyalkyloxy, haloalkoxyalkyl, aryloxyalkyl, heteroaryloxyalkyl, heterocycloalkyloxyalkyl, heterocycloalkylalkyl, heterocycloalkylalkyloxy, heterocycloalkyloxy, -alkylene-S(O)$_n$-R$_m$ (where n is 0 to 2 and R$_m$ is alkyl, haloalkyl, hydroxyalkyl, alkoxyalkyl, aryl, heteroaryl, or heteroaralkyl), -alkylene-NHSO$_2$-R$_w$ (where R$_w$ is alkyl, haloalkyl, aryl, heteroaryl, or heteroaralkyl), -alkylene-NHC(O)-R$_q$ (where R$_q$ is alkyl, halo alkyl, aryl, heteroaryl, or heteroaralkyl), and -(methylene)$_{n1}$-C(O)NR$_f$R$_g$ (where n1 is 0 or 1, R$_f$ is hydrogen, alkyl, or hydroxyalkyl and R$_g$ is hydrogen, alkyl, hydroxyalkyl, alkoxyalkyl, aryl, heteroaryl, heteroaralkyl, or heterocycloalkylalkyl, or R$_f$ and R$_g$ together with the nitrogen atom to which they are attached from heterocycloalkyl), and -(alkylene)$_{1-3}$-SiR$_{1-3}$ (where R is alkyl).

40. The compound according to claim 1, wherein A is piperidino or 1-methyl-1-oxo-1$\lambda^5$-phosphinane.

41. A method of expanding stem cells and hematopoietic progenitor cells, said method comprising:
    subjecting stem cells and hematopoietic progenitor cells in vitro to an effective amount of a compound of claim 1 or a pharmaceutically acceptable salt and/or solvate thereof.

42. A method of expanding stem cells and hematopoietic progenitor cells, said method comprising:
    subjecting stem cells and hematopoietic progenitor cells in vitro to an effective amount of a compound of claim 34 or a pharmaceutically acceptable salt and/or solvate thereof.

43. A method of expanding stem cells, said method comprising:
    subjecting stem cells in vitro to an effective amount of a compound of claim 1 or a pharmaceutically acceptable salt and/or solvate thereof.

44. A method of expanding stem cells, said method comprising:
    subjecting stem cells in vitro to an effective amount of a compound of claim 34 or a pharmaceutically acceptable salt and/or solvate thereof.

45. A method of expanding hematopoietic progenitor cells, said method comprising:
    subjecting hematopoietic progenitor cells in vitro to an effective amount of a compound of claim 1 or a pharmaceutically acceptable salt and/or solvate thereof.

46. A method of expanding hematopoietic progenitor cells, said method comprising:
    subjecting hematopoietic progenitor cells in vitro to an effective amount of a compound of claim 34 or a pharmaceutically acceptable salt and/or solvate thereof.

* * * * *